(12) United States Patent
Wilkinson et al.

(10) Patent No.: US 7,344,885 B2
(45) Date of Patent: Mar. 18, 2008

(54) RECOMBINANT EXPRESSION CASSETTES WITH A FUNGAL 3' TERMINATION SEQUENCE THAT FUNCTION IN PLANTS

(75) Inventors: Jack Q. Wilkinson, Cary, NC (US); Kevin McBride, Davis, CA (US); Sean Bertain, Piedmont, CA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 488 days.

(21) Appl. No.: 10/600,230

(22) Filed: Jun. 20, 2003

(65) Prior Publication Data

US 2004/0092020 A1   May 13, 2004

Related U.S. Application Data

(60) Provisional application No. 60/390,529, filed on Jun. 20, 2002.

(51) Int. Cl.
*C12N 15/82* (2006.01)

(52) U.S. Cl. ..................... 435/419; 435/320.1

(58) Field of Classification Search ............. 435/320.1
See application file for complete search history.

(56) References Cited

OTHER PUBLICATIONS

Rothnie H.M et al. The contribution of AAUAAA and the upstream element UUUGUA to the efficiency of mRNA 3'-end formation in plants. EMBO J. May 1, 1994;13(9):2200-10.*

* cited by examiner

*Primary Examiner*—Cynthia Collins
(74) *Attorney, Agent, or Firm*—Morgan & Finnegan, LLP

(57) ABSTRACT

The present invention provides recombinant expression cassettes comprising a fungal 3' termination sequence which is functional in a plant. The recombinant expression cassettes comprise a plant promoter operably linked to a coding sequence having a stop codon, and the fungal 3' termination sequence. The fungal 3' termination sequence is heterologous to the coding sequence. The fungal 3' termination sequence comprises structural features including a cleavage site, a positioning element, and an upstream element. The present invention also comprises methods for construction of the plant expression cassettes and introducing the cassettes into plant cells.

6 Claims, 4 Drawing Sheets

RECOMBINANT EXPRESSION CASSETTES WITH A FUNGAL 3' TERMINATION SEQUENCE THAT FUNCTION IN PLANTS

CROSS-REFERENCE TO RELATED APPLICATIONS

This application claims the benefit under 35 U.S.C. § 119(e) of U.S. Ser. No. 60/390,529, filed Jun. 20, 2002, which is incorporated herein in its entirety.

COPYRIGHT NOTIFICATION

A portion of the disclosure of this patent document contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention relates to heterologous genetic constructs comprising non-plant 3' termination sequences and plant expression cassettes incorporating the heterologous genetic constructs. The present invention also comprises methods for construction of the plant expression cassettes and introducing the cassettes into plant cells.

BACKGROUND OF THE INVENTION

Processing of messenger RNA 3' termination sequences resulting in polyadenylation is a universal feature of gene expression in eukaryotic organisms (See for example, Nevins, J. R.: "The pathway of eukaryotic mRNA formation", *Ann. Rev. Biochem.*, 52:441-466 (1983)). This type of processing also has profound effects on gene expression, including total cessation of mRNA translation, as both mRNA stability and translatability are linked to polyadenylation. (Wickens, M., et al., "Life and Death in the Cytoplasm: Messages from the 3' termination sequence", *Curr. Opin. Genet. Dev.*, 7:220-232 (1997)). Evidence is accumulating that such alterations in 3' termination sequence processing represents a form of expressional control which is directed by the interaction of trans-factors with cis-elements found in the precursor mRNA 3' termination sequences.

Understanding the role of 3' termination sequence processing in gene expression becomes critical when considering methods of expressing heterologous genes comprising "foreign" 3' termination sequences. This is especially true in the case of plants where the introduction of foreign genes makes dramatic improvements in crop plants feasible through otherwise straightforward gene transfer technology. However, despite extensive research, attempts to express foreign genes with non-plant 3' termination sequences in plants has thus far met with failure. For example, plant cells have been reported to be unable to recognize 3' termination sequences in *Saccharomyces cerevisiae* genes (see e.g.; Barton, K. A., et al., *Cell*, 32:1033-1043 (1983) and Irniger, s., et al., "Different Sequence Elements are required for function of Califlower Mosaic Virus Polyadenylation Site in *Saccharomyces cerevisiae* Compared with in Plants", *Mol. and Cell. Biol.*, 2322-2330 (1992)), as well as many other sources (See e.g., Koncz, c. et al., "A simple method to transfer, integrate and study expression of foreign genes, such as chicken ovalbumin and α-actin in plant tumors", *EMBO J.*, 3:(5), 1029-1037 (1984)).

This apparent lack of functionality of foreign 3' termination sequences in plants has lead to a scarcity of 3' termination sequences suitable for use in plant expression vectors for heterologous genes. In effect, only plant and plant viral 3' termination sequences can currently be considered for use in such vectors and, of the possible functional 3' termination sequences, only a few have been developed due to the difficulties in operably linking heterologous sequences to form a functional gene. Still other plant 3' termination sequences are unsuitable as they lead to undesirable recombination events with native sequences or trigger "gene silencing" through various mechanisms such as the formation of anti-sense RNA species. This set of circumstances increases the complexity of expressing foreign genes in plant cells and severely limits a primary method of controlling genetic expression in response to tissue type, environmental stimuli, and other factors. Identification of non-plant 3' termination sequences which are functional in plants, 3' cis regulatory elements necessary for expression in plants, and methods for constructing novel 3' termination sequences capable of functioning in plants would therefore be a significant advance in the expression of foreign genes in plant species.

SUMMARY OF THE INVENTION

The present invention provides recombinant expression cassettes comprising a plant promoter operably linked to a coding sequence having a stop codon and a non-plant 3' termination sequence. The non-plant 3' termination sequence is heterologous to the coding sequence. The non-plant 3' termination sequence also comprises a cleavage site, a positioning element, and an upstream element and has at least 60% identity to a native fungal or native animal 3' termination sequence and less than 90% identity to a native plant 3' termination sequence. Alternatively, the non-plant 3' termination sequence is unable to selectively bind to any known plant sequence under stringent conditions, as defined herein. The cleavage site of the non-plant 3' termination sequence comprises the sequence YA, defining the position of endonucleolytic cleavage and subsequent 3' polyadenylation. The positioning element is 6 bases long, with at least 4 out of 6 bases being adenine, and located between 10 bases and 40 bases 5' of the cleavage site. The upstream element is located between 1 base and 250 bases 5' of the positioning element; and, comprises the sequence TAYRTA or two or more repeats of TA, TG, or TA and TG where the repeats are separated by 0 to 10 bases.

In one aspect of the present invention is a plant cell comprising the expression cassette described in the previous paragraph.

Another aspect of the present invention provides a recombinant expression cassette with a cleavage site flanked by a pair thymidine-rich regions. Each of the thymidine-rich regions comprises at least 6 base pairs of at least 80% thymidine; and is within about 50 bases of the cleavage site.

In another aspect of the invention, the recombinant expression cassette has a viral promoter.

In another aspect, the 3' termination sequence of the recombinant expression cassette has at least 70% sequence identity to SEQ ID NO:1, SEQ ID NO:2, SEQ ID NO:3, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, or SEQ ID NO:31.

A further embodiment of the present invention is an isolated 3' termination sequence that is functional in plants and can be PCR-amplified by primers selectively hybridizing under stringent conditions to the same sequence as either primer pair SEQ ID NOs: 4 and 5, SEQ ID NOs: 6 and 7, SEQ ID NOs: 8 and 9, SEQ ID NOs: 10 and 11, SEQ ID NOs: 32 and 33, SEQ ID NOs: 34 and 35, SEQ ID NOs: 36 and 37, SEQ ID NOs: 38 and 39, SEQ ID NOs: 40 and 41, SEQ ID NOs: 42 and 43, SEQ ID NOs: 44 and 45, SEQ ID NOs: 46 and 47, SEQ ID NOs: 48 and 49, SEQ ID NOs: 50 and 51, SEQ ID NOs: 52 and 53, SEQ ID NOs: 54 and 55, SEQ ID NOs: 56 and 57, SEQ ID NOs: 58 and 59, or SEQ ID NOs: 60 and 61. In addition, the isolated 3' termination sequence is a nucleotide sequence having at least 60% identity to a native fungal or native animal 3' termination sequence and less than 90% identity to a native plant 3' termination sequence.

Another embodiment of the present invention is a method for isolating a recombinant protein. The method involves obtaining a nucleic acid encoding the recombinant protein, using this nucleic acid in constructing a recombinant expression cassette comprising the nucleic acid and a stop codon, operably linked with a non-plant 3' termination sequence. The non-plant 3' termination sequence used in constructing the expression cassette is heterologous to the coding sequence and comprises a cleavage site, a positioning element, and an upstream element and has at least 60% identity, sometimes at least 70% identity, occasionally at least 80% identity, or possibly at least 90% identity to a native fungal or native animal 3' termination sequence and less than 90% identity to a native plant 3' termination sequence. The cleavage site of the non-plant 3' termination sequence comprises the sequence YA, defining the position of endonucleolytic cleavage and subsequent 3' polyadenylation. The positioning element is 6 bases long, with at least 4 out of 6 bases being adenine, and located between 10 bases and 40 bases 5' of the cleavage site. The upstream element is located between 1 base and 250 bases 5' of the positioning element; and, comprises the sequence TAYRTA or two or more repeats of TA, TG, or TA and TG where the repeats are separated by 0 to 10 bases. The expression cassette is then used to transfect a plant cell. The transfected plant cell is then cultured in a manner allowing the cell to express the recombinant protein. Finally, the recombinant protein is isolated.

Still another embodiment of the invention is a method of identifying non-plant 3' termination sequences that are functional in plants. The method comprises obtaining a non-plant 3' termination sequence that has a nucleotide sequence having at least 60% identity, sometimes at least 70% identity, occasionally at least 80% identity, or possibly at least 90% identity to a native fungal or native animal 3' termination sequence and less than 90% identity to a native plant 3' termination sequence; a cleavage site comprising the sequence YA defining the position of endonucleolytic cleavage and subsequent 3' polyadenylation; a positioning element of 6 bases located between 10 bases and 40 bases 5' of the cleavage site and with at least 4 out of 6 bases being adenine; and an upstream element that is located between 1 base and 250 bases 5' of the positioning element and comprises TAYRTA or two or more repeats of TA, TG, or TA and TG where the repeats are separated by 0 to 10 bases. This non-plant 3' termination sequence is used in constructing an expression cassette having a functional plant promoter operably linked with a coding sequence encoding a selectable marker that is in turn operably linked with the 3' termination sequence described above. Finally, the selectable trait displayed by the marker gene is detected.

Another embodiment is a method for making a transgenic plant. The method involves first obtaining a nucleic acid encoding a genetic trait to be expressed. A recombinant expression vector is constructed for the plant transfection. This recombinant expression vector comprises a promoter that is functional in plants operably linked with the nucleic acid encoding the genetic trait to be expressed. The nucleic acid is in turn operably linked with a non-plant 3' termination sequence having the same characteristics as the 3' termination sequence described in the previous paragraph. A plant cell is transfected with this recombinant expression vector and is subsequently cultured into a viable plant expressing the genetic trait.

A further embodiment of the present invention is an isolated 3' termination sequence that is functional in plants and is identical to a native fungal or native animal 3' termination sequence.

DEFINITIONS

Figure 1:
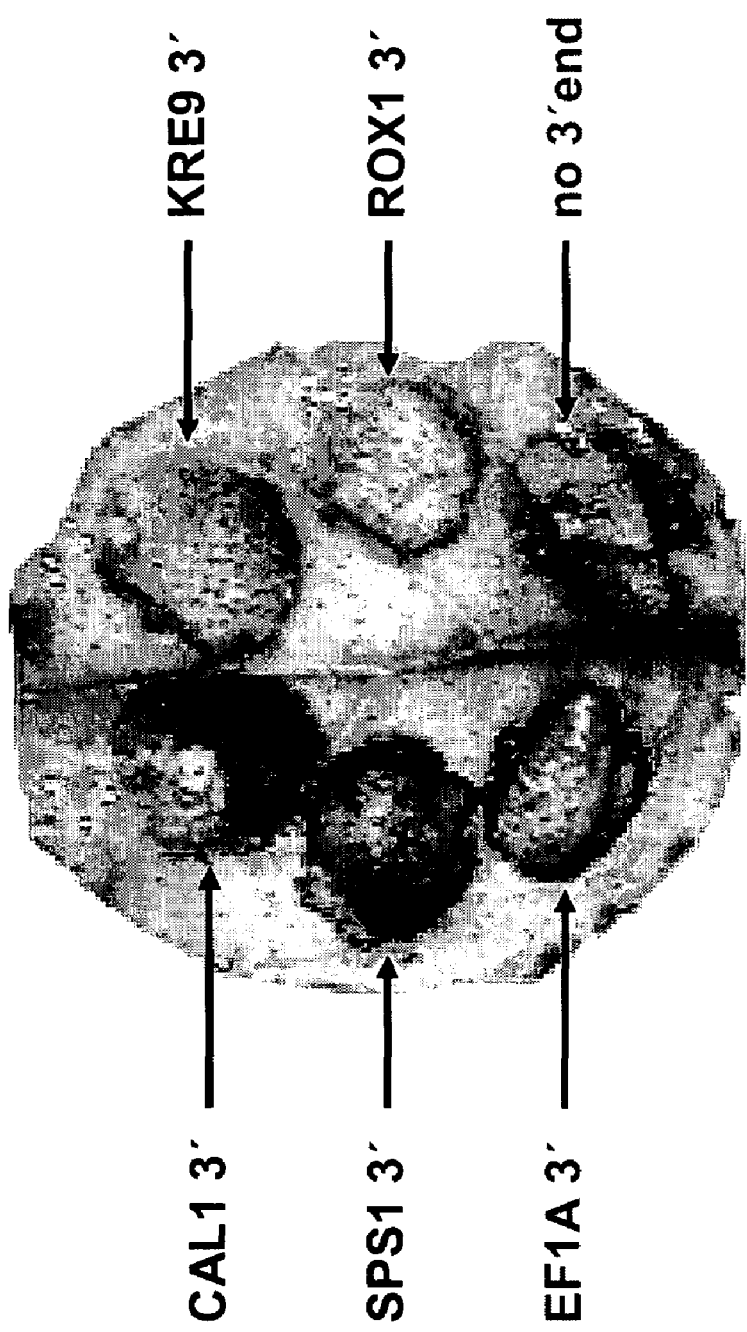
FIG. 1 illustrates the functionality of various yeast 3' termination sequences in plants by measuring the activity of the linked GUS gene in *Agrobacterium*-infiltrated *Nicotiana benthamiana* leaves.

The term "3' termination sequence" refers to the DNA sequence portion of a gene that contains a polyadenylation signal and any other regulatory signal capable of affecting mRNA processing or gene expression. The polyadenylation signal is usually characterized by affecting an endonucleic cleavage at a "cleavage site" and the addition of polyadenylic acid tracts to the new 3' end created by the cleavage reaction.

The term "3' polyadenylation" refers to the process of adding a string of several to dozens of adenylyl residues to the 3' end of a nucleic acid. 3' polyadenylation normally occurs in the course of mRNA processing in the nucleus, following endonucleolytic cleavage of the 3' termination sequence.

The term "cis element" refers to any polynucleotide sequence or region capable of being recognized and bound in a specific manner by a binding partner, usually a protein or nucleic acid.

The term "cleavage site" refers to the nucleotide sequence "YA", and is commonly found flanked by thymidine-rich regions within about 50 nucleotides. Functionally, the cleavage site marks the precise position where the 3' termination sequence processing complex cleaves the 3' termination sequence in preparation for 3' polyadenylation of the freshly formed 3' end. Cleavage at the cleavage site normally occurs between the nucleotide pair making up the cleavage site.

The term "coding sequence", in relation to nucleic acid sequences, refers to a plurality of contiguous sets of three nucleotides, termed codons, each codon corresponding to an amino acid as translated by biochemical factors according to the universal genetic code, the entire sequence coding for an expressed protein, or an antisense strand that inhibits expression of a protein. A "genetic coding sequence" is a coding sequence where the contiguous codons are intermittently interrupted by non-coding intervening sequences, or "introns." During mRNA processing intron sequences are removed, restoring the contiguous codon sequence encoding the protein or anti-sense strand.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

The term "endonucleolytic cleavage" refers to severing of the covalent bond between two nucleotides in a polynucleotide chain, neither of the nucleotides being a terminal nucleotide prior to severing the covalent bond. A terminal nucleotide is a nucleotide that has flanking nucleotides at only it's 3' or the 5' end.

The term "functional in plants" refers to the ability of any genetic element or protein to exhibit at least a part of its native behavior in plants. Native behavior refers to those aspects of function normally displayed when expressed or present in a homologous (native) system. When the behavior can be manifested as a measurable activity, the magnitude of the activity can be greater than, equal to or less than the magnitude displayed in a homologous system. Where a genetic element or protein has multiple behavioral aspects, the genetic element or protein is considered "functional in plants" if only one aspect of it's native behavior is exhibited to any degree when expressed or present in a plant.

The term "genetic trait" refers to a property of a cell that is encoded in the nucleic acid pool of the cell and normally can be passed on, typically through mitotic or meiotic division, to progeny of the original cell.

The term "heterologous" when used with reference to portions of a nucleic acid or protein indicates that the molecule comprises two or more subsequences that are not found in the same relationship to each other in nature. For instance, a heterologous nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "isolate" in all of its grammatical forms refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other components normally present in a solution of the same.

The terms "isolated" and "purified" do not encompass nucleic acids or polypeptides present in their natural source.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); Rossolini et al., *Mol. Cell. Probes*, 8:91-98 (1994)). The term "nucleic acid" is used interchangeably with the terms "gene", "cDNA", "mRNA", "oligonucleotide", and "polynucleotide".

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

As used herein a "nucleic acid probe" or "oligonucleotide probe" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, U, or T) or modified bases (e.g., 7-deazaguanosine, inosine, etc.). In addition, a linkage other than a phosphodiester bond may join the bases in a probe, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence, depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe" or "labeled oligonucleotide probe" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "nucleotide" refers to a single purine or pyrimidine-derived ribonucleic acid, phosphorylated at least in one position. Unless otherwise indicated, all nucleotide representations in this manuscript comply with the single letter code recommended by the IUPAC-IUB Biochemical Nomenclature Commission, and published by the Patent and trademark Office of the United States in the PatentIn User Manual. These include those for pyrimidines (Y), purines (R), amino (M), keto (K), strong interactions (i.e., G or C) (S), weak interactions (i.e., A or T) (W) and others, in addition to the commonly used symbols A, C, G, T, and U.

The term "nucleotide sequence" refers to a contiguous chain of covalently linked nucleotides.

The term "native fungal" refers to any aspect of a fungus, or portion thereof, that represents the aspect or portion as it occurs naturally in the fungus, but not including variant forms, to any degree, of the aspect or aspect portion.

The term "native animal" refers to any aspect of a animal, or portion thereof, that represents the aspect or portion as it occurs naturally in the animal, but not including variant forms, to any degree, of the aspect or aspect portion.

The term "non-plant", in relation to isolated biological material, refers to a biological source incapable of undergoing photosynthesis under any circumstances. In relation to synthetic or semi-synthetic material, the term "non-plant" refers to any composition that is not identical to a composition found in plants. For example, a "non-plant 3' termination sequence" is any 3' termination sequence that is not identical in nucleotide sequence to a 3' termination sequence known to exist in any plant or plant pathogen that inserts its DNA into the plant (e.g. *Agrobacterium*, plant viruses). In the context of this definition, the term "plants" encompasses the organisms classified in the Kingdom Plantae while excluding members of the Kingdom Animalia and the Kingdom Fungi.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The terms "primers" or "primer pairs" refer to oligonucleotide probes capable of recognizing and hybridizing to specific nucleotide sequences found in a target gene or sequence to be amplified by polymerase chain reaction (PCR). The degree of complementarity required between the primers and the target sequence determines the specificity, or stringency of conditions required for hybridization of the sequences. A temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications*, Academic Press, Inc. N.Y. (1990)).

The term "promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg, *Biochemistry of Plants*, 15:1-82 (1989). It is further recognized that since in most cases the exact boundaries of regulatory sequences have not been completely defined, nucleic acid fragments of different lengths may have identical promoter activity.

The term "recombinant DNA" refers to DNA that has been derived or isolated from any source that may be subsequently chemically altered, and later introduced into a plant cell. An example of recombinant DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Therefore "recombinant DNA" includes completely synthetic DNA, semi-synthetic DNA, DNA isolated from biological sources, and DNA derived from introduced RNA. Generally, the recombinant DNA is not originally resident in the plant genotype which is the recipient of the DNA, but it is within the scope of the invention to isolate a gene from a given plant genotype, and to subsequently introduce multiple copies of the gene into the same. genotype, e.g., to enhance production of a given gene product such as a storage protein.

The recombinant DNA used for transformation herein may be circular or linear, double-stranded or single-stranded. Generally, the DNA is in the form of chimeric DNA, such as plasmid DNA, which can also contain coding regions flanked by regulatory sequences that promote the expression of the recombinant DNA present in the resultant plant. For example, the recombinant DNA may itself comprise or consist of a promoter that is active in plants, or may utilize a promoter already present in the plant genotype that is the transformation target.

A "recombinant expression cassette" is a recombinant DNA containing a nucleic acid capable of being transcribed in a cell. The recombinant expression cassettes of the invention generally comprise a coding sequence transcribed by cellular (or cellularly-derived) agents, although vectors used for the amplification of nucleotide sequences (both coding and non-coding) are also encompassed by the definition. In addition to the coding sequence, expression vectors will generally include restriction enzyme cleavage sites and the other initial, terminal and intermediate DNA sequences that are usually employed in vectors to facilitate their construction and use. The expression vector can be part of a plasmid, virus, or a nucleic acid fragment.

The term "messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA. "Antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression.

The term "plant" refers to a photosynthetic organism, either eukaryotic or prokaryotic. The term "higher plant" refers to a eukaryotic plant. "Native plant" refers to any aspect of a plant, or portion thereof, that represents the aspect or portion as it occurs naturally in the plant, but not including variant forms, to any degree, of the aspect or aspect portion.

The term "positioning element" refers to a region of nucleotide sequence that is 6 nucleotides long, 4 of the 6 nucleotides being adenine, and located between 10 nucleotides and 40 nucleotides upstream of the 3' termination sequence cleavage site. Functionally, the positioning element is believed to be a critical component necessary for correct alignment of the 3' termination sequence processing complex prior to the complex cleaving the 3' termination sequence precisely at the cleavage site, as defined herein.

The terms "selectable marker", or "selectable trait" refers to a molecule that imparts a distinct phenotype to cells expressing the nucleic acid fragment encoding the marker and thus allow such transformed cells to be distinguished from cells that do not have the marker. A selectable marker confers a trait which one can 'select' for by chemical means, i.e., through the use of a selective agent (e.g., a herbicide, antibiotic, or the like). A screenable marker confers a trait which one can identify through observation or testing, i.e., by 'screening'. A "scoreable marker" is a screenable marker with a phenotypic trait that can be quantified.

The phrase "selectively (or specifically) hybridizing" refers to the binding, duplexing, or hybridizing between two particular nucleotide sequences under stringent hybridization conditions when the sequences are present in a complex mixture (e.g., total cellular or library DNA or RNA).

The term "recombinant protein" refers to a protein or polypeptide having a heterologous sequence, the combination of amino acids not normally being present in nature. Recombinant protein also refers to proteins or polypeptides that are transcribed from recombinant (heterologous) genes.

The terms "sequence similarity", "sequence identity", or "percent identity," in the context of two or more nucleic acids or polypeptide sequences, refer to two or more sequences or subsequences that are, when optimally aligned with appropriate nucleotide insertions or deletions, the same or have a specified percentage of amino acid residues or nucleotides that are the same (i.e., 50% identity, 65%, 70%, 75%, 80%, preferably 85%, 90%, 91%, 92%, 93%, 94%, 95%, 96%, 97%, 98%, 99% or higher identity to a nucleotide sequence such as SEQ ID NO:1), when compared and aligned for maximum correspondence over a comparison window, or designated region as measured using one of the following sequence comparison algorithms or by manual alignment and visual inspection. This definition also refers to the compliment of a test sequence. Preferably, the identity exists over a region that is at least about 25 nucleotides in length, or more preferably over a region that is 50-100 nucleotides in length. These relationships hold, notwithstanding evolutionary origin (Reeck et al., *Cell*, 50:667 (1987)). When the sequence identity of a pair of polynucleotides or polypeptides is greater or equal to 65%, the sequences are said to be "substantially identical."

The term "stop (or "termination") codon" refers to a unit of three adjacent nucleotides in a polynucleotide coding sequence that specifies translational termination of protein synthesis (i.e., mRNA translation) by the ribosomal complex.

The phrase "stringent conditions" or "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength and pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

The terms "substantially similar" or "substantially identical" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to regulate gene expression through effects on transcription and translation rates or to mediate gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript such as 3' end processing, transport, mRNA stability, or the ability to mediate or suppress gene silencing. For "regulatory" or non-coding sequences such as promoters, enhancers, introns, and 3' ends, any of these modifications (base substitutions, insertions, or deletions) that do not significantly affect the functional properties of the sequence would be considered to produce a "substantially similar" nucleic acid. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize, under stringent conditions (0.1×SSC, 0.1% SDS, 65° C.), with the nucleic acid fragments disclosed herein.

A "comparison window", as used herein, includes reference to a segment of any one of the number of contiguous positions selected from the group consisting of from 4 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, *Adv. Appl. Math.*, 2:482 (1981), by the homology alignment algorithm of Needleman and Wunsch, *J. Mol. Biol.*, 48:443 (1970), by the search for similarity method of Pearson and Lipman, *Proc. Nat'l. Acad. Sci. USA*, 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acid sequences, the BLAST and BLAST 2.0 algorithms and the default parameters discussed below are used.

The BLAST and BLAST 2.0 algorithms are described in Altschul et al., *Nuc. Acids Res.*, 25:3389-3402 (1977) and Altschul et al., *J. Mol. Biol.*, 215:403-410 (1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, *Proc. Natl. Acad. Sci. USA*, 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Nat'l. Acad. Sci. USA*, 90:5873-5787 (1993)). One measure of similarity provided by the BLAST algorithm is the smallest sum probability (P(N)). P(N) provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An alternative to the BLAST program is the GCG (Genetics Computer Group, Program Manual for the GCG Package, Version 7, Madison, Wis.) PILEUP program. PILEUP creates a multiple sequence alignment from a group of related sequences using progressive, pair wise alignments to show relationship and percent sequence identity. It also plots a tree or dendrogram showing the clustering relationships used to create the alignment. PILEUP uses a simplification of the progressive alignment method of Feng and Doolittle, *J. Mol. Evol.*, 35:351-360 (1987). The method used is similar to the method described by Higgins and Sharp, CABIOS, 5:151-153 (1989). The program can align up to 300 sequences, each of a maximum length of 5,000 nucleotides or amino acids. The multiple alignment procedure begins with the pair wise alignment of the two most similar sequences, producing a cluster of two aligned sequences. This cluster is then aligned to the next most related sequence or cluster of aligned sequences. Two clusters of sequences are aligned by a simple extension of the pair wise alignment of two individual sequences. The final alignment is achieved by a series of progressive, pair wise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

The terms "thymidine-rich or T-rich region" refer to a region of nucleotide sequence at least 6 nucleotides long, within about 50 nucleotides of the 3' termination sequence cleavage site, and having a thymidine (or in the case of an mRNA, uracil) content of at least 80%. Functionally, thymidine-rich regions are currently believed to signal the polymerase complex transcribing the gene to pause prior to terminating transcription.

The term "transfect," in all of its forms, refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al., *Meth. Enzymol.*, 143:277 (1987)) and particle-accelerated or "gene gun" transformation technology (Klein et al., *Nature* (London) 327:70-73 (1987); U.S. Pat. No. 4,945,050, incorporated herein by reference).

"Transgenic" as used herein refers to any cell, cell line, tissue plant part or plant the genotype of which has been altered by the presence of an exogenous coding region. Typically, the exogenous coding region was introduced into the genotype by a process of genetic engineering, or was introduced into the genotype of a parent cell or plant by such a process and is subsequently transferred to later generations by sexual crosses or asexual propagation.

The term "upstream element" refers to a region of nucleotide sequence that has within it the hexanucleotide TAYRTA or 2 or more repeats of TA, TG, or TA and TG, where the repeats are separated by 0 to 10 nucleotides. Functionally, upstream elements aid in formation of the 3' termination sequence processing complex, and can modulate activity of the complex.

The term "viable" refers to the ability of a biological component or system to function, live, develop, or germinate under favorable conditions.

DETAILED DESCRIPTION OF THE INVENTION

I. Introduction

The present invention provides novel plant expression cassettes comprising non-plant 3' termination sequences, allowing for a greater degree of control over expression of the gene(s) contained within the cassette, whilst minimizing potential pitfalls associated with molecular interaction between homologous elements found in the expression cassette and the plant genome, such as molecular recombination and gene "silencing."

Non-plant 3' termination sequences of the present invention are either isolated or engineered to possess particular sequence motifs found by the inventors to be necessary for gene function in plants. These motifs include a cleavage site, a positioning element and an upstream element, each element demanding particular sequence and location requirements be met if the 3' termination sequence is to be functional in plants.

A general approach to isolating non-plant 3' termination sequences that are functional in plants involves first screening a gene sequence database, such as GENBANK, using the criteria noted above. Acceptable sequences isolated from this in silico screening of databases are then used to create PCR primers specific for the identified 3' termination sequence. The PCR primers are in turn used to amplify the 3' termination sequence from a suitable sequence library or from purified genomic DNA. Once isolated, the structure of the 3' termination sequence is checked for structural consistency with the polynucleotide expected from the sequence database search, and for functionality in biochemical assays, as described below.

The in silico sequence search for putative 3' termination sequences having the desired criteria can be performed with any number of analysis algorithms available commercially and in the public domain, such as the BLAST or PILEUP programs mentioned earlier. One first uses the analysis program to locate a suitable 3' termination sequence positioning element. Suitable 3' termination sequence positioning elements are 6 nucleotides long, and have at least four nucleotides that are adenine residues. Suitable positioning elements must also be located downstream from the coding sequence stop codon (UAA, UGA or UAG in frame with the coding sequence) for the gene containing the putative 3' termination sequence, and between 10 and 40 nucleotides upstream from a potential 3' termination sequence cleavage site (i.e., YA). Any putative 3' termination sequences lacking a positioning element meeting these criteria are eliminated from the pool of putative sequences.

Having limited the pool of putative 3' termination sequences to those having a suitable positioning element, the pool is then further limited by excluding all sequences lacking an upstream element as defined by the criteria of the present invention. This is accomplished by searching the pool for candidates having the sequence TAYRTA, or two or more repeats of TA, TG, or TA and TG in any combination, where the repeats are contiguous, or separated by up to 10 nucleotides. To qualify as an upstream element, the sequence must also be located downstream from the stop codon of the coding sequence and no more than 250 nucleotides upstream from the 5' nucleotide of the positioning element. Any putative 3' termination sequences not having the upstream element nucleotide sequence and location described above is discarded from the pool of 3' termination sequence candidates.

3' termination sequences remaining in the pool after discarding all of those sequences not meeting the criteria described in both of the previous two paragraphs are then tested for their functional characteristics in plants, as described in detail below.

3' termination sequences isolated in this manner will frequently be joined to a coding sequence, and possibly also to extraneous sequences 3' to the termination sequence of interest. These undesired sequences can be removed by methods common in the art. For example, their removal can be accomplished through cleavage with restriction endonucleases or a combination of restriction site engineering by site-directed mutagenesis combined with endonuclease cleavage. The latter approach offers the additional benefit of engineering additional restriction sites into the termination sequence to ease subsequent cloning steps. This technique is described in detail in Example 1.

By engineering these sequence motifs into other non-plant 3' termination sequences, it is possible to create novel non-plant 3' termination sequences that function in plants. The invention therefore also provides methods for constructing non-plant 3' termination sequences that are functional in plants as well as methods for testing the functionality of expression cassettes comprising non-plant 3' termination sequences modified according to the present invention. These methods use recombinant DNA technology known in the art to insert the common sequence motifs and where necessary to remove identified native motifs known to interfere with 3' termination sequence function in plants.

The invention also provides novel expression cassettes incorporating non-plant 3' termination sequences modified as disclosed herein. These novel expression cassettes can be used to transform plant cells that in turn can be grown to transgenic plants. Transgenic plants transformed with the expression cassettes of the present invention display stable genetic properties, with those embodiments where the cassettes are integrated into the host genome displaying typical Mendelian genetic segregation in crosses with both wild type and other transgenic strains. Moreover, as a consequence of their heterologous nature, the non-plant 3' termination sequences of the present invention are much less likely to contribute to gene silencing of native transcripts, nor are they prone to undesired recombination with the host genome, both common problems with constructs comprising plant 3' termination sequences.

A. General Recombinant Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994).

For nucleic acids, sizes are given in either kilobases (Kb) or base pairs (bp). These are estimates derived from agarose or acrylamide gel electrophoresis, from sequenced nucleic acids, or from published DNA sequences. For proteins, sizes are given in kilodaltons (kDa) or the number of amino acid residues. Proteins sizes are estimated from gel electrophoresis, from automated protein sequencing, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.*, 22:1859-1862 (1981), using an automated synthesizer, as described in Van Devanter et. al., *Nucleic Acids Res.*, 12:6159-6168 (1984). Purification of oligonucleotides is by either native acrylamide gel electrophoresis or by anion-exchange HPLC as described in Pearson & Reanier, *J. Chrom.*, 255:137-149 (1983).

One of skill in the art will recognize many ways of generating alterations in a given nucleic acid sequence. Such well-known methods include site-specific mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Berger and Kimmel, Guide to Molecular Cloning Techniques, *Methods in Enzymology*, Volume 152 Academic Press, Inc., San Diego, Calif. (Berger); Sambrook et al., *Molecular Cloning—A Laboratory Manual* (2nd ed.) Vol. 1-3, Cold Spring Harbor Laboratory, Cold Spring Harbor Press, N.Y., (Sambrook) (1989); and Current Protocols in Molecular Biology, F. M. Ausubel et al., eds., *Current Protocols*, a joint venture between Greene Publishing Associates, Inc. and John Wiley & Sons, Inc., (1994 Supplement) (Ausubel); Pirrung et al., U.S. Pat. No. 5,143,854; and Fodor et al., *Science,* 251:767-77 (1991). Product information from manufacturers of biological reagents and experimental equipment also provide information useful in known biological methods. Such manufacturers include the SIGMA Chemical Company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.), as well as many other commercial sources known to one of skill. Using these techniques, it is possible to insert or delete, at will, a polynucleotide of any length into a 3' termination sequence nucleic acid described herein.

For example, site-directed mutagenesis techniques are described in (Ling et al., "Approaches to DNA mutagenesis: an overview", *Anal Biochem.*, 254(2): 157-178 (1997); Dale et al., "In vitro mutagenesis", *Ann. Rev. Genet.*, 19:423-462 (1996); Botstein & Shortle, "Strategies and applications of in vitro mutagenesis", *Science,* 229:1193-1201 (1985); Carter, "Site-directed mutagenesis", *Biochem. J.*, 237:1-7 (1986); and Kunkel, "The efficiency of oligonucleotide directed mutagenesis" in *Nucleic Acids & Molecular Biology* (Eckstein, F. and Lilley, D. M. J. eds., Springer Verlag, Berlin) (1987)); mutagenesis using uracil containing templates (Kunkel, "Rapid and efficient site-specific mutagenesis without phenotypic selection", *Proc. Natl. Acad. Sci. USA,* 82:488-492 (1985); Kunkel et al., "Rapid and efficient site-specific mutagenesis without phenotypic selection", *Methods in Enzymol.*, 154:367-382 (1987); and Bass et al. (1988); oligonucleotide-directed mutagenesis (*Methods in Enzymol.*, 100:468-500 (1983); *Methods in Enzymol.*, 154: 329-350 (1987); Zoller & Smith, "Oligonucleotide-directed mutagenesis using M13-derived vectors: an efficient and general procedure for the production of point mutations in any DNA fragment", *Nucleic Acids Res.,* 10:6487-6500 (1982); Zoller & Smith "Oligonucleotide-directed mutagenesis of DNA fragments cloned into M13 vectors", *Methods in Enzymol.*, 100:468-500 (1983); and Zoller & Smith, "Oligonucleotide-directed mutagenesis: a simple method using two oligonucleotide primers and a single-stranded DNA template", *Methods in Enzymol.*, 154:329-350 (1987)); Taylor et al. (1985) "The rapid generation of oligonucleotide-directed mutations at high frequency using phosphorothioate-modified DNA", *Nucl. Acids Res.*, 13: 8765-8787 (1985); Nakamaye & Eckstein, "Inhibition of restriction endonuclease Nci I cleavage by phosphorothioate groups and its application to oligonucleotide-directed mutagenesis", *Nucl. Acids Res.,* 14:9679-9698 (1986); Sayers et al., "Y-T Exonucleases in phosphorothioate-based oligonucleotide-directed mutagenesis", *Nucl. Acids Res.,* 16:791-802 (1988); and Sayers et al. (1988); mutagenesis using gapped duplex DNA (Kramer et al., "The gapped duplex DNA approach to oligonucleotide-directed mutation construction", *Nucl. Acids Res.*, 12:9441-9456 (1984); Kramer & Fritz, "Oligonucleotide-directed construction of mutations via gapped duplex DNA", *Methods in Enzymol.*, 154:350-367 (1987); Kramer et al., "Improved enzymatic in vitro reactions in the gapped duplex DNA approach to oligonucleotide-directed construction of mutations", *Nucl. Acids Res.*, 16:7207 (1988); and Fritz et al., "Oligonucleotide-directed construction of mutations: a gapped duplex DNA procedure without enzymatic reactions in vitro", *Nucl. Acids Res.*, 16:6987-6999 (1988)).

Other techniques for altering DNA sequences include; Wells et al., "Cassette mutagenesis: an efficient method for generation of multiple mutations at defined sites", *Gene*, 34:315-323 (1985); and Grundstrom et al., "Oligonucleotide-directed mutagenesis by microscale 'shot-gun' gene synthesis", *Nucl. Acids Res.*, 13:3305-3316 (1985)), double-strand break repair (Mandecki, "Oligonucleotide-directed double-strand break repair in plasmids of *Escherichia coli:* a method for site-specific mutagenesis", *Proc. Natl. Acad. Sci. USA*, 83:7177-7181 (1986); and Arnold, "Protein engineering for unusual environments", *Current Opinion in Biotechnology*, 4:450-455 (1993)). Additional details on many of the above methods can be found in *Methods in Enzymology* Volume 154, which also describes useful controls for trouble-shooting problems with various mutagenesis methods. The sequence of the cloned genes and synthetic oligonucleotides can be verified after cloning using, e.g., the chain termination method for sequencing double-stranded templates of Wallace et al., *Gene*, 16:21-26 (1981).

B. Sources and Methods for Isolating 3' Termination Sequences

In general, 3' termination sequences are isolated from genomic or cDNA libraries, or through amplification techniques using oligonucleotide primers and purified genomic DNA. In one embodiment of the present invention, non-plant 3' termination sequences that function in plants without alteration can be isolated from a variety of sources, by first identifying 3' ends of known non-plant genes that satisfy the selection criteria described herein. PCR primers can then be synthesized using sequence information from the selected 3' termination sequences and the primers used to amplify the non-plant 3' termination sequences from any suitable library or genomic DNA preparation. Examples of primers constructed using this technique are listed as SEQ ID NOS:4-9 and reproduced below. These primers were used to amplify 3' termination sequences from specific genes of the yeast *Saccharomyces cerevisiae*. The amplified 3' termination sequences are provided as SEQ ID NOS:1-3 and SEQ ID NOS 16-31.

```
Primer set for isolating the 3' termination sequence of SEQ ID NO:1;

SEQ ID NO:4
CAL1 (5)CE, coding strand termination sequence primer:
5'-GCGCGCGGAAGGAGGAAAGTGACTCCTTCGTTGC-3'

SEQ ID NO:5
CAL1 (3)NE, noncoding strand termination sequence primer:
5'-GGTACCTCATCATTTGGAGGTTCAAGTCATGGAG-3'

Primer set for isolating the 3' termination sequence of SEQ ID NO:2;

SEQ ID NO:6
SPS1 (5)CE, coding strand termination sequence primer:
5'-GCGCGCAAGTCACAAGTAGTAGCGAGTTACAAC-3'

SEQ ID NO:7
SPS1 (3)NE, noncoding strand termination sequence primer:
5'-GGTACCTTGTAATATAACGAGGAAACGCAACTTATCC-3'

Primer set for isolating the 3' termination sequence of SEQ ID NO:3;

SEQ ID NO:8
KRE9 (5)CE, coding strand termination sequence primer:
KRE9-5CE: 5'-GCGCGCCATCCAAGAGATTGTCTTTGTCTGCAAG-3'

SEQ ID NO:9
KRE9 (3)NE, noncoding strand termination sequence primer:
5'-GGTACCAGCGAAACACCAGAGTTGACCCCACAG-3'

Primer set for isolating the 3' termination sequence of SEQ ID NO:16

SEQ ID NO:32
BDF1-5C1:
5'-CCTAGGTGAAGAAGAGTGACTGAATTTTG-3'

SEQ ID NO:33
BDF1-3N2:
5'-GGTACCGTAAATTTTGTGAGTTAGGTTG-3'

Primer set for isolating the 3' termination sequence of SEO ID NO:17

SEQ ID NO:34
CHS5-5C1:
5'-CCTAGGATTAATGGATGCCTTCAATGAG-3'

SEQ ID NO:35
CHS5-3N2:
```

-continued
5'-GGTACCTAGAATGTGTTTAGGGATAGTTG-3'

Primer set for isolating the 3' termination sequence of SEQ ID NO:18

SEQ ID NO:36
GSG1-SC1
5'-ACTAGTTAGCTTTATTGGATGACTTTATGG-3'

SEQ ID NO:37
GSG1-3N2:
5'-GGTACCAAGTGAAGATTTTGATTATACCAG-3'

Primer set for isolating the 3' termination sequence of SEQ ID NO:19

SEQ ID NO:38
UBI2-5C1:
5'-CCTAGGAATTGCGTCCAAAGAAGAAGTTG-3'

SEQ ID NO:39
UBI2-3N2:
5'-GGTACCATATTACGTTGACGGGAGTTTTC-3'

Primer set for isolating the 3' termination sequence of SEQ ID NO:20

SEQ ID NO:40
IQG2-5C1:
5'-CCTAGGAGTCCACTCTTCACCTCGTCTTG-3'

SEQ ID NO:41
IQG2-3N2:
5'-GGTACCTTTTCCCTTTTGGTAGTCAC-3'

Primer set for isolating the 3' termination sequence of SEQ ID NO:21

SEQ ID NO:42
UBI3-5C1:
5'-CCTAGGTAAGTGTCATTCCGTCTACAAG-3'

SEQ ID NO:43
UBI3-3N2:
5'-GGTACCTACACATGTCATCGCAGTGGAC-3'

Primer set for isolating the 3' termination sequence of SEQ ID NO:22

SEQ ID NO:44
RPO2-5C1:
5'-CCTAGGTGATATAGTATATCATCCTTACG-3'

SEQ ID NO:45
RPO2-3N2:
5'-GGTACCCTTAGGTGATATCGAGC-3'

Primer set for isolating the 3' termination sequence of SEQ ID NO:23

SEQ ID NO:46
YEF3-5C1:
5'-CCTAGGTGATGCTTACGTTTCTTCTGACG-3'

SEQ ID NO:47
YEF3-3N2:
5'-GGTACCGTGGCAGTTACTTTATATAGAGTG-3'

Primer set for isolating the 3' termination sequence of SEQ ID NO:24

SEQ ID NO:48
AOX-5C1:
5'-CCTAGGAGTTTGTAGCCTTAGACATGAC-3'

SEQ ID NO:49
AOX-3N2:
5'-GGTACCGGTAATTAACGACACCCTAGAGG-3'

Primer set for isolatina the 3' termination sequence of SEQ ID NO:25

SEQ ID NO:50
NTBP-5C1:
5'-CCTAGGTCTAAAGAGTAGCAATTCTGATG-3'

SEQ ID NO:51
NTBP-3N2:

```
                                            -continued
5'-GGTACCACTTTGACGGAACAGAGGATGGAAG-3'

Primer set for isolating the 3' termination sequence of SEQ ID NO:26

SEQ ID NO:52
NHYM-5C1:
5'-CCTAGGACTGTTGCGTAGACATGAGC-3'

SEQ ID NO:53
NHYM-3N2:
5'-GGTACCAGTGCATTCCATGGATTCG-3'

Primer set for isolating the 3' termination sequence of SEQ ID NO:27

SEQ ID NO:54
NACT-5C1:
5'-CCTAGGATCGTCCACCGCAAGTGCTTC-3'

SEQ ID NO:55
NACT-3N2:
5'-GGTACCTGTATACTAGCAATACTGTAC-3'

Primer set for isolating the 3' termination sequence of SEQ ID NO:28

SEQ ID NO:10
hLaminLF:
5'-GGCGCGCCTAGGCCAAGCCCTGCGTCCAGCGAGC-3'

SEQ ID NO:11
hLaminLR:
5'-CGGGGTACCCCGAGTCAGCTTGTGCAACAGCGTCG-3'

Primer set for isolating the 3' termination sequence of SEQ ID NO:29

SEQ ID NO:56
hLaminSF:
5'-GGCGCGCCTAGGGAAGCCTGCACGCGGCAGTTC-3'

SEQ ID NO:57
hLaminSR:
5'-CGGGGTACCCCGGAATAAACTCAGAGGCAGAAC-3'

Primer set for isolatina the 3' termination sequence of SEQ ID NO:30

SEQ ID NO:58
hC2F:
5'-GGCGCGCCTAGGCTAGCCATGGCCACTGAGCCCT-3'

SEQ ID NO:59
hC2:
5'-CGGGGTACCCCGCCAAGGCCAGCCCTACCTGGC-3'

Primer set for isolating the 3' termination sequence of SEQ ID NO:31

SEQ ID NO:60
UBQF:
5'-GGCGCGCCTAGGTGGCTGTTAATTCTTCAGTCATGGC-3'

SEQ ID NO:61
UBQR:
5'-CGGGGTACCCCGCCTAACTTGTAATGACTTAAACAGC-3'
```

Alternatively, non-plant 3' termination sequences that are not functional in plants can serve as a backbone from which termination sequences that are functional in plants can be engineered. This is performed generally by removing or replacing sequence motifs present in the native non-plant 3' termination sequence that interfere with gene expression in plants, and adding the cis regulatory elements identified in the present invention as necessary components of a 3' termination sequence capable of functioning in plants.

cDNA Libraries

Although cDNA libraries only provide information regarding the 3' termination sequence 5' to the polyadenylation/cleavage site, this information is frequently all that is required to construct a 3' termination sequence that is functional in plants. First, unlike 3' termination sequences of animal genes, plant gene 3' termination sequences do not have sequence elements necessary for correct 3' termination sequence processing downstream from the cleavage site. Second, transcription often terminates shortly after the polymerase transcribes the cleavage site. As a consequence, the nucleotide sequence 3' to the cleavage site is often much shorter and less important than the untranslated sequence 5' to the cleavage site.

Recombinant or semi-synthetic 3' termination sequences can be constructed using the 3' termination sequence data from a cDNA library. This is accomplished, for example, by replacing the poly-A tail of the cDNA with either a nucleic acid located 3' to the cleavage site of a different 3' termination sequence, or by replacing the poly-A tail with a suitable synthetic nucleic acid. Alternatively, the cDNA nucleotide sequence information is valuable as a source of primers and probes for isolating full-length 3' termination sequences from genomic DNA or to search for the appropriate downstream sequences in various sequence databases such as GENBANK.

Preparation of cDNA libraries can be performed by standard techniques well known in the art. Well known cDNA library construction techniques can be found for example, in Sambrook et al., *Molecular Cloning: A Laboratory Manual;* Cold Spring Harbor Laboratory, Cold Spring Harbor, N.Y. (1989). It will be readily apparent to those skilled in the art that libraries can be constructed from a variety of cell and viral types.

In constructing a cDNA library, the mRNA is made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene,* 25:263-269 (1983); Sambrook et al., supra; Ausubel et al., supra).

Genomic Libraries

Genomic libraries provide a source for full-length 3' termination sequences. To construct a genomic library, the DNA is extracted from the tissue and either mechanically sheared or enzymatically digested to yield fragments of about 12-20 kb. The fragments are then separated by gradient centrifugation from undesired sizes and are constructed in bacteriophage λ vectors. These vectors and phage are packaged in vitro. Recombinant phage are analyzed by plaque hybridization as described in Benton & Davis, *Science,* 196:180-182 (1977). Colony hybridization is carried out as generally described in Grunstein et al., *Proc. Natl. Acad. Sci. USA.,* 72:3961-3965 (1975). See also, Gussow, D. and Clackson, T., *Nucl. Acids Res.,* 17:4000 (1989).

Purified Genomic DNA

Genomic DNA can be easily purified from many sources using commercially available kits and following the manufacturer's instructions. Alternatively, genomic DNA preparations from certain tissues and organisms can be purchased from various vendors or repositories such as the American Type Culture Collection (ATCC).

PCR Amplification

As mentioned previously, polymerase chain reaction and other in vitro amplification methods are also useful in cloning 3' termination sequences. Examples include making nucleic acids to use as probes for detecting, in physiological samples, the presence of polynucleotides comprising a 3' termination sequence of the present invention, for nucleic acid sequencing, or other purposes (see U.S. Pat. Nos. 4,683,195 and 4,683,202; *PCR Protocols: A Guide to Methods and Applications* (Innis et al., eds, 1990)). Such methods can be used to amplify 3' termination sequences directly from genomic DNA, or from DNA libraries.

Restriction endonuclease sites can also be incorporated into the primers and used in site-directed mutagenesis methods to create constructs for modification by insertion or deletion of nucleic acid(s). Sequences amplified by the PCR reaction can be purified from agarose gels and cloned into an appropriate construct for further amplification or other manipulation.

PCR techniques include 5' and/or 3' RACE techniques, both being capable of generating a full-length 3' termination sequence from a suitable library (e.g., Frohman, et al., *Proc. Natl. Acad. Sci. USA,* 85:8998-9002 (1988)). The strategy involves using specific oligonucleotide primers for PCR amplification of DNA comprising a 3' termination sequence. These specific primers are designed through identification of nucleotide sequences either in the 3' termination sequence itself, and/or the vector comprising the 3' termination sequence.

Site-Directed Mutagenesis

Site-directed mutagenesis may be used to modify non-plant 3' termination sequences to create 3' termination sequences that are functional in plants or to create restriction sites in a 3' termination sequence that can in turn be used to insert or delete specific nucleotide sequences necessary to create 3' termination sequences that are functional in plants from non-plant sources. The technique further provides a ready ability to prepare and test sequence variants by introducing one or more nucleotide sequence changes into the DNA.

The technique of site-directed mutagenesis is generally well known in the field (see i.e., Adelman et al., *DNA,* 2:183 (1983) and the references cited above). As initially developed, the technique typically employs a phage vector that exists in both a single stranded and double stranded form. Typical vectors useful in site-directed mutagenesis include vectors such as the M13 phage (Messing et al., *Third Cleveland Symposium on Macromolecules and Recombinant DNA,* Ed: A. Walton, Elsevier, Amsterdam, (1981)). These phage are readily commercially available and their use is generally well known to those skilled in the art. Double stranded plasmids are also routinely employed in site directed mutagenesis, eliminating the step of transferring the gene of interest from a plasmid to a phage.

In general, site-directed mutagenesis in accordance herewith is performed by first obtaining a single-stranded nucleic acid that includes within its sequence a 3' termination sequence. An oligonucleotide that is generally complimentary with the region of the 3' termination sequences but bearing nucleotide substitutions required to create a cis element necessary to render the 3' termination sequence functional in plants is then generated. Such oligonucleotides can be generated for example by the de novo (phosphoramidite) synthesis techniques noted above. This oligonucleotide is then annealed with the single-stranded nucleic acid comprising a 3' termination sequence, and subjected to DNA polymerizing enzymes such as *E. coli* polymerase I Klenow fragment, in order to complete the synthesis of the mutation-bearing strand. A heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement. Typically, a primer of about 17 to 25 nucleotides in length is preferred, with about 5 to 10 residues on both sides of the junction of the sequence being altered. Suitable techniques are also described in U.S. Pat. No. 4,888,286, incorporated herein by reference.

The preparation of 3' termination sequence variants using site-directed mutagenesis is provided as a means of producing novel, potentially useful 3' termination sequences and is not meant to be limiting, as there are other ways in which 3' termination sequence variants may be obtained. For example, recombinant vectors comprising a 3' termination sequence may be treated with mutagenic agents to obtain sequence variants (see, e.g., the method described by Eichenlaub, *J. Bacteriol,* 138:559-566 (1979)).

Although the foregoing methods are suitable for use in mutagenesis, the use of site-directed primers in conjunction with the polymerase chain reaction (PCR) technique is generally now preferred. Briefly, sequence information is modified by replacing directed nucleic acids in a non-plant 3' termination sequence by amplifying the non-plant 3' termination sequence with primers generally directed for the 3' termination sequence, but where at least one of the primers comprises the desired nucleotide substitutions resulting in amplification of a 3' termination sequence containing the desired substitutions. Resulting reaction products should be examined by e.g., restriction mapping, electrophoresis and/or automated nucleotide sequencing to confirm the desired product is obtained.

Restriction Endonucleases

Although site-directed mutagenesis techniques allow for precise base alterations in a nucleotide sequence, restriction endonucleases allow for larger pieces of polynucleotide to be inserted into or deleted from a 3' terminations sequence, either by using existing restriction sites or by first creating the necessary restriction sites by, for example, site-directed mutagenesis.

In general, an endonuclease is an enzyme that is capable of breaking DNA into smaller segments. An endonuclease is capable of attaching to a strand of DNA somewhere in the middle of the strand and breaking it. By comparison, an exonuclease removes nucleotides from the end of a strand of DNA. All of the endonucleases discussed herein are capable of breaking double-stranded DNA into segments. This may require the breakage of two types of bonds: (1) covalent bonds between phosphate groups and deoxyribose residues, and (2) hydrogen bonds (A-T and C-G) which hold the two strands of DNA to each other.

A "restriction endonuclease" breaks a segment of DNA at a precise sequence of bases. Over 100 different endonucleases are known, each of which is capable of cleaving DNA at specific sequences. See, e.g., Roberts, T. et al., *Proc. Natl. Acad. Sci. USA*, 76:760 (1979). All restriction endonucleases are sensitive to the sequence of bases. Some restriction endonucleases create a "cohesive" end with a 5' overhang (i.e., the single-stranded "tail" has a 5' end rather than a 3' end). Cohesive ends can be useful in promoting desired ligations. For example, an EcoRI end is much more likely to anneal to another EcoRI end than to, for example, a HaeIII end.

In addition, some endonucleases are sensitive to whether certain bases have been methylated. For example, two endonucleases, MboI and Sau3a are capable of cleaving the DNA at the same sequence of bases, but MboI cannot cleave the sequence if an adenine residue present in the sequence is methylated (me-A). Sau3a can cleave this sequence, regardless of whether either A is methylated. To some extent the methylation (and therefore the cleavage) of a plasmid may be controlled by replicating the plasmids in cells with desired methylation capabilities. An *E. coli* enzyme, DNA adenine methylase (dam), methylates the A residues that occur in GATC sequences. Strains of *E. coli* that do not contain the dam enzyme are designated as dam– cells. Cells that contain dam are designated as dam.sup.+ cells.

Several endonucleases are known which cleave different sequences, but create cohesive ends that are fully compatible with cohesive ends created by other endonucleases. For example, at least five different endonucleases create 5' GATC overhangs (MboI, Sau3a, BglII, BclI, and BamHI). A cohesive end created by any of the endonucleases will ligate preferentially to a cohesive end created by any of the other endonucleases. However, a ligation of cohesive ends created by different enzymes will in some cases create a new site that is not recognized by one or both of the restriction endonucleases creating the initial cohesive ends. For example, ligating a BglII end with a BamHI end will create a sequence that cannot be cleaved by either Bgl II or BamHI; however, it can be cleaved by MboI (unless methylated) or by Sau3a. Many other such examples exist and are known in the art.

C. Synthetic Nucleic Acid Constructs

As noted previously, semi-synthetic 3' termination sequences can easily be fashioned by replacing the poly-A tail of a suitable cDNA with a synthetic sequence derived from sequence 3' to the cleavage site of a second 3' termination sequence. (cf. Sambrook et al., *Molecular Cloning: A Laboratory Manual*, Cold Spring Harbor Laboratory, New York, USA (1989)). Synthetic oligonucleotides can also be constructed for use as probes to isolate 3' termination sequences or for creating 3' termination sequences de novo. This de novo synthesis is generally performed using a series of overlapping oligonucleotides usually 40-120 bp in length, representing both the sense and non-sense (antisense) strands of the gene. These DNA fragments are then annealed, ligated and cloned. Alternatively, amplification techniques can be used with precise primers to amplify the whole 3' termination sequence, or a specific subsequence.

Fragments corresponding to various parts of an entire 3' termination sequence, including the sequence of incorporated cis elements of the present invention, can optionally be from any source including different 3' termination sequences, and combined to form novel 3' termination sequences. Alternatively, cis elements from one 3' termination sequence may be "swapped" into a different 3' termination sequence. See, e.g., Cunningham, et al., *Science*, 243:1330-1336 (1989); and O'Dowd, et al., *J. Biol. Chem.*, 263:15985-15992 (1988) for analogous techniques, each of which is incorporated herein by reference. Thus, new chimeric 3' termination sequences that are functional in plants will result from the functional linkage of the cis elements described in this invention in non-plant 3' termination sequences, with necessary deletion of interfering non-plant cis elements, the latter process again accomplished using standard recombinant DNA technology.

Of course entirely novel 3' termination sequences can be constructed using sequence information from any number of sources, but preferably from sequence information relating to 3' termination sequences. Using the selection criteria disclosed herein, synthetic chimeric 3' termination sequence constructs can be created de novo, as discussed in more detail below.

The 3' termination sequences of the invention, modified 3' termination sequences or hybrid 3' termination sequences may be prepared synthetically by established standard methods, e.g. the phosphoramidite method described by Beaucage and Caruthers, *Tetrahedron Letters*, 22:1859-1869 (1981), or the method described by Matthes et al., *EMBO J.*, 3:801-805 (1984). According to the phosphoramidite method, oligonucleotides are synthesized, e.g. in an automatic DNA synthesizer, purified, annealed, ligated and cloned in suitable vectors.

Finally, as discussed briefly above, the portion of a 3' termination sequence upstream from the cleavage site of any expressed gene can be isolated from a suitable cDNA expression library. These partial 3' termination sequences can be used to create probes for isolation of full-length 3' termination sequences, or as templates that can be extended using synthetic oligonucleotides and standard PCR techniques known in the art and described above, to create full-length synthetic or semi-synthetic 3' termination sequences through ligation of heterologous oligonucleotides.

D. Molecular Labels

The particular label or detectable group used in the assays described herein is not a critical aspect of the invention, as long as it does not significantly interfere with binding of the nucleic acids or proteins used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™); fluorescent dyes and techniques capable of monitoring the change in fluorescent intensity, wavelength shift, or fluorescent polarization (e.g., fluorescein isothiocyanate, Texas red, rhodamine, and the like); radiolabels (e.g., $^{3}H$, $^{125}I$, $^{35}S$, $^{14}C$, or $^{32}P$); enzymes (e.g., horse radish peroxidase, alkaline phosphatase and others commonly used in an ELISA); and colorimetric labels such as colloidal gold or colored glass or plastic beads (e.g., polystyrene, polypropylene, latex, etc.). For exemplary methods for incorporating such labels, see U.S. Pat. Nos. 3,940,475; 3,817,837; 3,850,752; 3,939,350; 3,996,345; 4,277,437; 4,275,149; and 4,366,241.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand (e.g., biotin) is covalently bound to the molecule. The ligand then binds to another molecule (e.g., streptavidin) that is either inherently detectable or covalently bound to a signal system, such as a detectable enzyme, a fluorescent compound, or a chemiluminescent compound.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

E. Identifying Non-Plant 3' Termination Sequences that Function in Plants

The present invention initially identifies four specific selection criteria for identifying non-plant 3' termination sequences capable of functioning in plants, namely;

1. The presence of a canonical positioning element downstream of a coding region stop codon
2. The presence of "T-rich regions" downstream of the positioning element
3. A bias for "A-rich" regions at or near the positioning element
4. The non-plant termination sequences have no homologous counterpart in the plant variety to be transformed.

These four criteria are refined to greater precision to define a cleavage site comprising the sequence YA, a positioning element that is 6 bases long, at least 4 of which are adenine and located between 10 to 40 bases 5' of the cleavage site, and an upstream element that is located between 1 base and 250 bases 5' of the positioning element, and has a sequence comprising either TAYRTA or two or more repeats of TA, TG, or TA and TG where the repeats are separated by 0 to 10 bases. To ensure that the non-plant 3' termination sequence has no plant homologues, the additional limitation that the termination sequence must have at least 60% identity, sometimes at least 70% identity, occasionally at least 80% identity, or possibly at least 90% identity to a native fungal or native animal 3' termination sequence and less than 90% identity to a native plant 3' termination sequence was introduced.

It is important to realize that while positioning elements and cleavage sites are present in a given 3' termination sequence in a 1:1 ratio, each positioning element/cleavage site pair may be accompanied by multiple upstream elements, with each upstream element meeting the criteria outlined above. The entire group of elements comprising a cleavage site, positioning element and one or more upstream elements is termed a 3' regulatory set. It is also important to recognize that the 3' termination sequences of the present invention may comprise more than one 3' regulatory set, as is the case for plant 3' termination sequences generally. Additionally, experimental evidence (reviewed in Rothnie, *Plant Mol Biol* 32:43-61 (1996)) has shown that when the original 3' end cleavage site is removed or mutated, cleavage can still occur at an appropriate position downstream of the functional positioning element, even in the absence of a suitable YA dinucleotide, although with less precision. Therefore, the absence or alteration of a known cleavage site does not necessarily preclude the functionality of a 3' regulatory set, as the termination sequence processing complex in plants may operate in some capacity in a distance-dependent manner based upon the positioning and upstream elements. This potential flexibility is recognized and is considered a variation of the criteria outlined above.

F. Obtaining Non-Plant 3' Termination Sequences that Function in Plants

There are multiple ways of obtaining 3' termination sequences satisfying the criteria noted above and being functional in plants. For example, the 3' termination sequences can be identified from databases and the nucleic acid recovered from a DNA library by methods common to the art of molecular biology. Alternatively the 3' termination sequences can be isolated from any non-plant source and engineered to meet the criteria for a 3' termination sequence functional in plants using the recombinant DNA techniques described above. Examples of using these selection criteria to identify non-plant 3' termination sequences capable of functioning in plants and in using the selection criteria for engineering novel 3' termination sequences that function in plants are detailed in the sections that follow.

Isolation of Native Non-Plant 3' Termination Sequences that Function in Plants

As noted above, a general approach to isolating non-plant 3' termination sequences that are functional in plants involves first screening a gene sequence database using the 3' termination motif criteria of the present invention. Acceptable sequences isolated from this in silico screening of databases are then used to create PCR primers specific for the identified 3' termination sequence. The PCR primers are in turn used to amplify the 3' termination sequence from a suitable sequence library or genomic DNA preparation. Once isolated, the structure of 3' termination sequence is checked for structural consistency with the polynucleotide expected from the sequence database search, and for functionality in biochemical assays, as described below.

In an exemplary application, the 3' termination sequences of the CAL1, SPS1, and KRE9 genes were identified from *Saccharomyces cerevisiae* by in silico screening as potential candidates for testing. In the first step of the application, an in silico sequence search was performed by examining the GENBANK annotations of well-characterized yeast genes for which at least 350 bases of sequence downstream of the stop codon was provided. The search was confined to genes related to fungal biology (spore formation, chitin synthesis, etc.) and for which no plant counterparts are known or expected. The 3' sequences of these genes were then evaluated for the particular elements and properties outlined above. First, the 3' sequences were scanned for a positioning element 6 nucleotides long, where at least four nucleotides were adenine residues. The positioning elements also had to be located downstream from the coding sequence stop codon (UAA, UGA or UAG in frame with the coding sequence) of the gene and between 10 and 40 nucleotides upstream from a potential 3' termination sequence cleavage site (i.e., YA). Any yeast genes lacking a positioning element meeting these criteria were eliminated from the candidate pool of putative sequences.

Having limited the pool of candidates to those nucleotide sequences having a suitable positioning element, the pool was further limited by excluding all sequences lacking an upstream element as defined by the criteria of the present invention. This was accomplished by searching the pool for candidates having the sequence TAYRTA, or two or more repeats of TA, TG, or TA and TG in any combination, where the repeats are contiguous, or separated by up to 10 nucleotides. To qualify as an upstream element, the sequences also had to be located downstream from the stop codon of the coding sequence and no more than 250 nucleotides upstream from the 5' nucleotide of the positioning element. Any yeast genes not having the upstream element nucleotide sequence and location described above were discarded from the pool of 3' termination sequence candidates.

Figure 2:
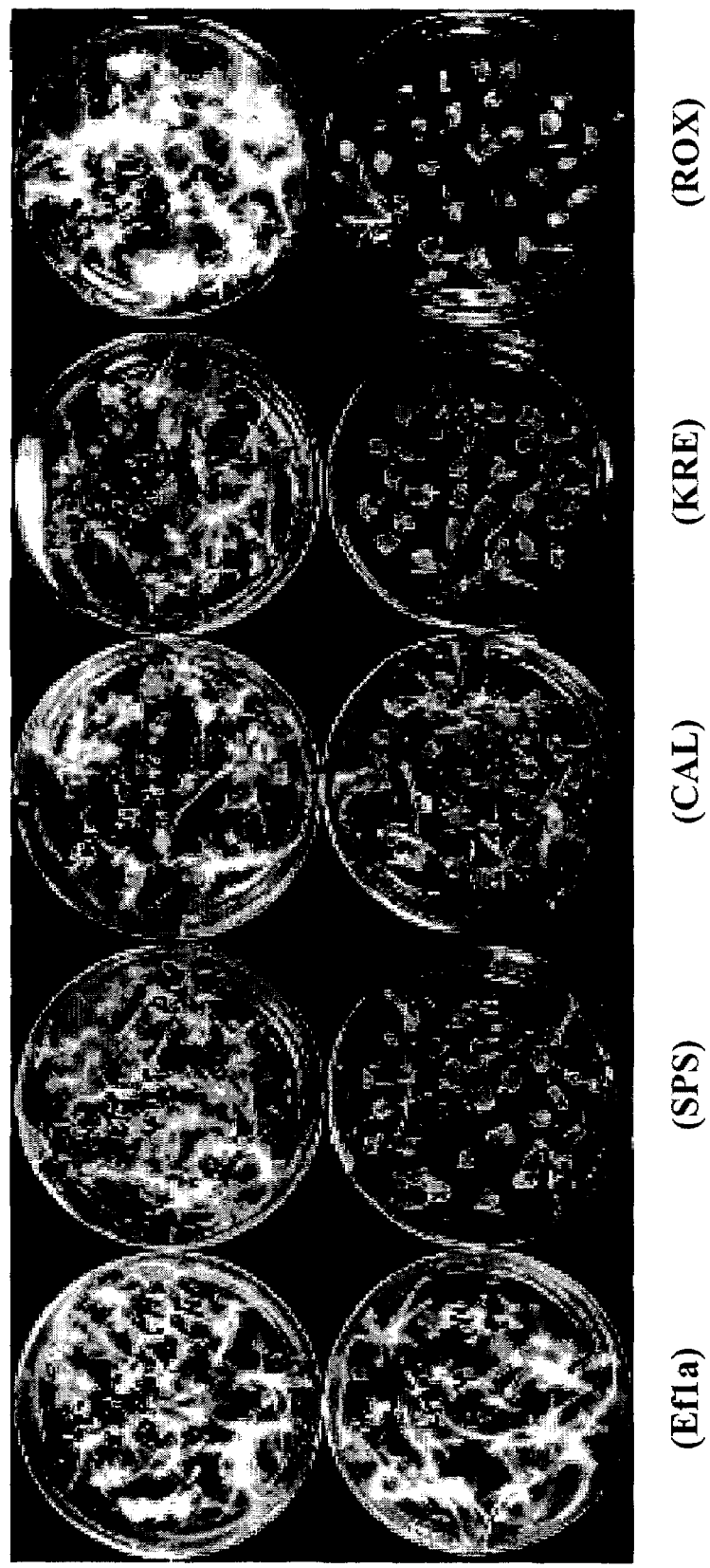
FIG. 2 illustrates the functionality of various yeast 3' termination sequences in plants by measuring the level of kanamycin resistance in transfected tobacco hairy roots.
Figure 3:
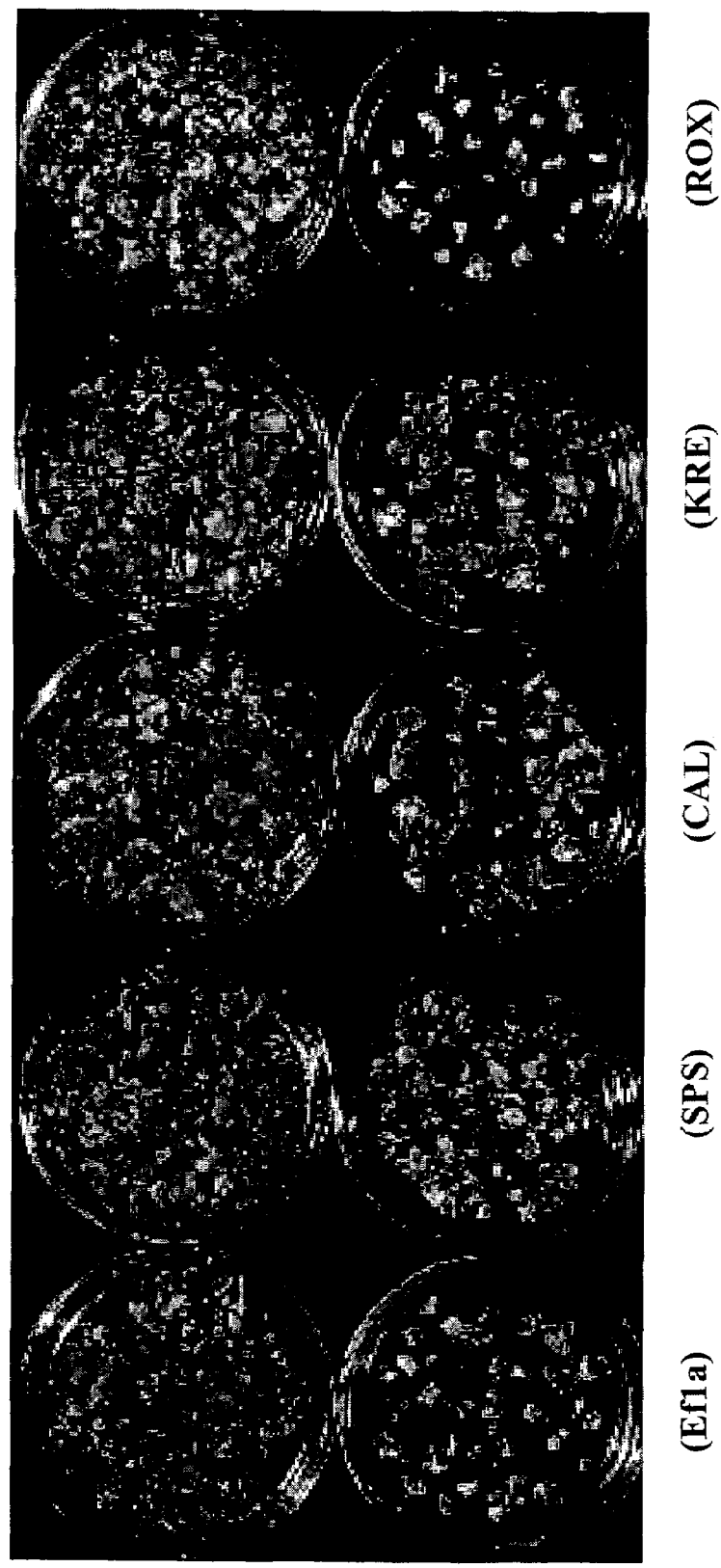
FIG. 3 illustrates the functionality of various yeast 3' termination sequences in plants by measuring the level of kanamycin resistance in tobacco shoots.
Figure 4:
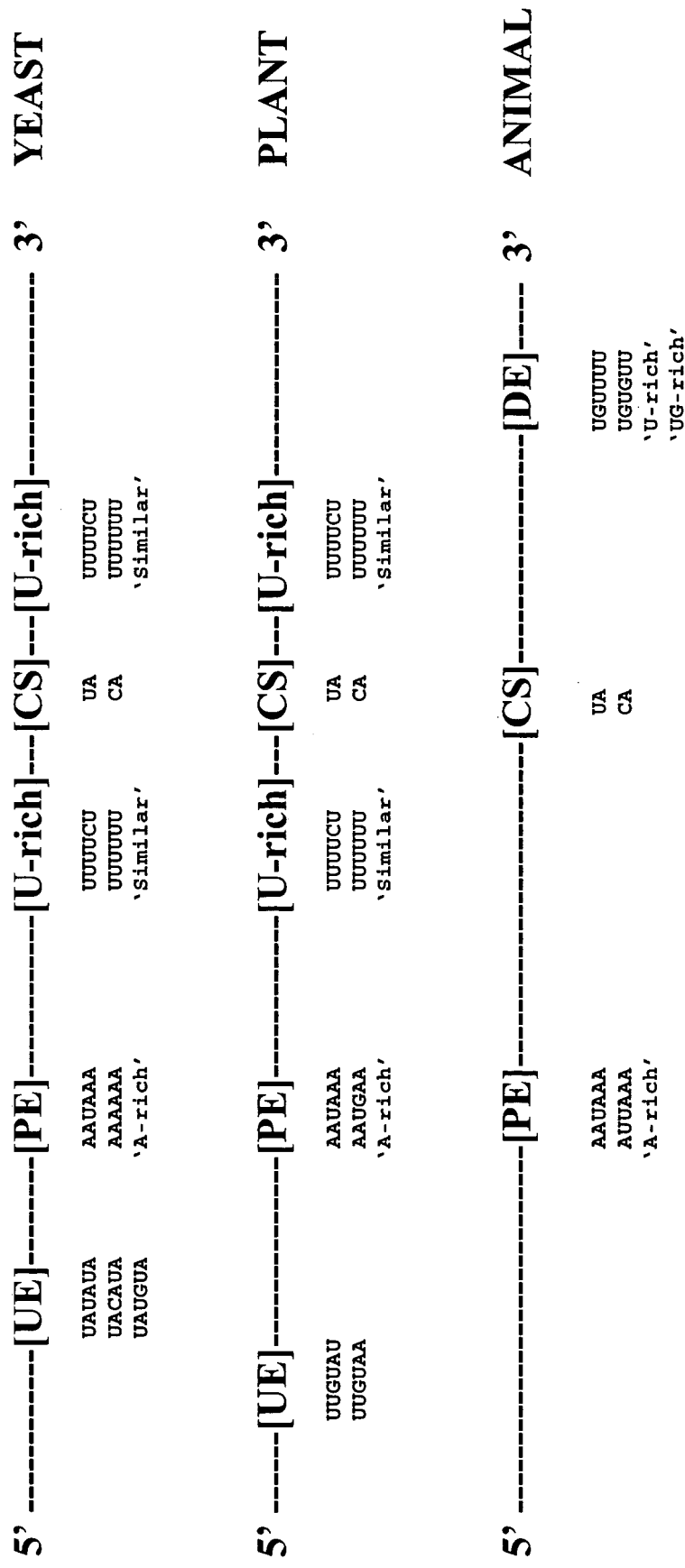
FIG. 4 is a cartoon of composite sequences and a schematic depiction of the relative orientation of cis regulatory sequences in the 3' termination sequences of genes from yeast, plants and animals, respectively.

The remaining candidate nucleotide sequences were examined for T-rich regions around the putative positioning elements and cleavage sites. The CAL1, SPS1, and KRE9 gene 3' ends each have at least 2 copies of the classic animal positioning element (AATAAA), numerous nucleotide stretches with at least 4 out of 6 residues being adenine, and multiple T-rich regions. The 3' ends from these genes were chosen for further evaluation, although many more candidates were identified and the search was clearly not exhaustive. PCR primers were then constructed based on the published sequences of these 3 genes (see SEQ ID NOS: 4-9), and used to amplify each respective 3' termination sequence. Expression cassettes were then constructed comprising a promoter functional in plants operably linked with a reporter gene (beta-glucuronidase) or selectable marker gene (neomycin phosphotransferase) which in turn was linked to one of the 3 isolated yeast 3' termination sequences. The expression cassettes were then used to transfect *Agrobacterium sp.*, which were subsequently used to transform plant cells in transient or stable expression assays (see FIGS. 1-3). Reporter gene expression was observed for each of the 3 yeast termination sequences described, at a level comparable to or greater than a control plant 3' end (from the *Arabidopsis* EF1a gene), and significantly greater than the reporter gene with no 3' termination sequence at all (FIG. 1). Additionally, the 3' ends were sufficiently functional to allow nptII gene expression and selection of transformed roots and shoots on kanamycin-containing media (FIGS. 2 and 3). Therefore, the sequence criteria used to identify these yeast 3' termination sequences, and which share some common motifs with plant 3' termination sequences (see FIG. 4), were sufficient to allow the identification of non-plant 3' termination sequence that are functional in plants.

A second search with slightly modified criteria was conducted for additional *Saccharomyces cerevisiae* 3' ends that might also prove to be highly functional in plants. In this case, the candidate pool was not limited to genes related to fungal biology. Selected candidates from this in silico exercise include the 3' ends from GENBANK entries U18116, (SEQ ID NO:69) Z49198 (SEQ ID NO:70), U26674 (SEQ ID NO:71), X05729 (SEQ ID NO:72), X01474 (SEQ ID NO:73), X05730 (SEQ ID NO:74), X03128 (SEQ ID NO:75), and J05583 (SEQ ID NO:76).

To extend the searching beyond *S. cerevisiae* 3' ends and into other fungal species, a limited in silico screen was carried out for *Aspergillus nidulans* 3' ends using the search parameters outlined above. Selected candidates from this screen include the 3' ends from GENBANK entries U28333 (SEQ ID NO:78), M22869 (SEQ ID NO:80), and AJ001157 (SEQ ID NO:79).

A limited effort was made, using the criteria described above, to identify 3' ends from human genes that may be functional in plants. Possible candidates for isolation and in planta testing include the 3' ends from GENBANK entries X04803 (SEQ ID NO:68) and M94363 (SEQ ID NO:66).

Engineering, Non-Plant 3' Termination Sequences to Function in Plants

While isolation of native non-plant 3' termination sequences that function in plants offers a direct way of obtaining the desired sequence material, engineering non-functional 3' termination sequences such that they will function in plants offers several additional benefits over using native sequences. First, engineered 3' termination sequences can be derived from any non-plant source. The only restrictions placed on the source material are that it is not derived from a plant and that it comprises the non-translated portion of a gene. This latter requirement is necessary as termination sequences are frequently several hundred to several thousand bases long. Nucleic acids of these lengths are known to adopt complex secondary structures. In the case of nucleic acids comprising known 3' termination sequences, it is presumed that the secondary structure adopted will not inhibit gene expression in plants, at least after the sequence has been engineered to function in plants.

As noted above, non-plant 3' termination sequences require at least one 3' regulatory group of elements to function in plants. To the extent that these elements are absent from the non-plant 3' termination sequence, they can be inserted using techniques well known in the art. For example, using the techniques described in detail above, restriction sites can be engineered into the non-plant 3' termination sequence at precise positions using site-directed mutagenesis techniques, allowing for the insertion of the necessary sequence elements after restriction endonuclease digestion. Where a native sequence is positioned correctly and homologous to the regulatory element to be inserted, site-directed mutagenesis can be used to directly alter the native sequence and incorporate the desired regulatory element.

Any non-plant source of genetic material can be used to obtain 3' termination sequences suitable for modification according to the present invention. Generally 3' termination sequence material will be identified through database searches using the same search tools as described above for identifying non-plant 3' termination sequences that are functional in plants without modification. In the case of sequences sought for modification, however, the criteria applied is much less stringent-than that described in the identification procedure above.

Sequences sought to be modified to function in plants must be from the 3' untranslated region of a gene capable of being expressed when in a native environment. As noted above, this requirement is necessary to limit the possibility of the termination sequence adopting an inhibitory secondary structure. By definition, this also means that the sequence must be downstream (3') to the stop codon of the coding sequence of the gene. As a practical limitation, the sequence should also contain a cleavage site (YA) or, in the case of cDNA, terminate at the 3' end with a "Y" excluding any poly-dT (poly A) tail. In the case of a cDNA, or any other potential sequence lacking a complete cleavage site, a cleavage site and any additional 3' trailing sequences that may be added can be constructed by appending an appropriate polynucleotide to the 3' terminus of the potential sequence lacking a complete cleavage site.

As an example, a sequence suitable for engineering into a 3' termination sequence that is functional in plants can be obtained from a cDNA by constructing PCR primers for the cDNA and any 3' termination sequence having a complete cleavage site and trailing 3' sequence. Using an overlapping primer that spans the cleavage site, a complete, chimeric 3' termination sequence can be created. The resulting chimeric 3' termination sequence will have a 5' end from the cDNA and a 3' end derived from the 3' termination sequence having a complete cleavage site and trailing 3' sequence. The 3' termination sequence having a complete cleavage site and trailing 3' sequence can be from any source, including an entirely novel synthetic sequence.

Once a termination sequence suitable for engineering has been isolated to serve as a platform for modifications, the 3' regulatory group members can be individually inserted into the 3' termination sequence. Alternatively, the entire 3' regulatory group can be inserted as a unit, complete with nucleotide sequences intervening between the individual elements of the group to ensure proper orientation.

An exemplary protocol for constructing heterologous 3' termination sequences functional in plants involves first cloning a non-plant 3' termination sequence into a standard ds-DNA plasmid. The plasmid is then converted to a ss-DNA by standard methods (Maniatas et al.). The ss-DNA is annealed to 40-50 nucleotide DNA oligomers having base mismatches at the site(s) intended to be engineered to create restriction sites allowing for the directionally-controlled insertion of desired termination sequence elements of the present invention, or eliminate an interfering native element. The hybrid DNA is then converted to a closed ds-DNA plasmid vector by use of DNA polymerase and standard protocols. Plasmids containing the desired alterations are next identified by restriction analysis following plasmid DNA isolation from *E. coli* strains transformed with the mutagenized DNA. The mutagenized DNA is isolated and subjected to restriction endonuclease cleavage, with a restriction enzyme capable of cleaving at the engineered restriction sites. The desired termination sequence elements, which can be entirely synthetic or derived from a biological source (or combination of both) are then inserted into the non-plant 3' termination sequence. Analysis for structural correctness is confirmed by PCR and DNA sequencing. Genetic or biochemical tests are then carried out as detailed below to ensure the new construct in functional in plants.

In some non-plant 3' termination sequences there exists sequence motifs that interfere with gene expression in plants. This is particularly true in termination sequences isolated from animal sources that contain elements downstream from the termination sequence cleavage site not found in plants. These elements can be removed or replaced with neutral sequence using the recombinant techniques described above. As the sequence elements are very short, (between 5 and 25 bases), neutral sequence can be determined through routine experimentation.

It is contemplated that linker regions and the like can be used in constructing 3' termination sequences. Linker regions may be needed, for example, to correctly position regulatory elements.

Deletion Analysis of 3' Termination Sequences

Sequences within a 3' termination sequence that affect the functionality of the entire sequence in a given system may be determined by using deletion constructs analogous to those described by Sherri et al. for the determination of HSP70 intron alterations which impact transcription of genes operably linked thereto (see U.S. Pat. No. 5,593,874, hereby incorporated by reference). Briefly, several expression plasmids are constructed to contain a reporter gene operably linked to different candidate nucleotide sequences that are obtained either by restriction enzyme deletion of internal sequences of the 3' termination sequence, restriction enzyme truncation of sequences at the 5' and/or 3' termination sequence of the 3' termination sequence, or by the introduction of single nucleic acid base changes by site-directed PCR into the 3' termination sequence. Expression of the reporter gene by the deletion constructs is detected. Detection of expression of the reporter gene in a given deletion construct indicates that the candidate nucleotide sequence in that deletion construct comprises a functional 3' termination sequence. By quantifying the results, sequences inhibitory to 3' termination sequence function can be identified.

Similarly, deletion analysis will also yield data allowing for the identification of nucleotide sequences necessary for, or enhancing 3' termination sequence function. Identified sequences can then be tested by incorporation into engineered 3' termination sequences at different locations relative to the cleavage site. By creating a number of constructs, each containing the necessary/enhancing nucleotide sequence at a different location in an engineered 3' termination sequence, the optimal nucleotide sequence and positioning of cis elements can be ascertained.

II. Constructing Expression Cassettes

Expression cassettes of the present invention include both single gene expression cassettes and binary or multiple gene cassettes. Binary vector systems are described in further detail in Gynheung An et al., Binary Vectors, *Plant Molecular Biology Manual*, A3:1-19 (1980). Single gene expression cassettes invariably comprise a claimed 3' termination sequence. Generally, expression cassettes containing a single gene are constructed to test the functionality of the 3' termination sequence in the plant cell system being used. The gene in such systems, when expressed, displays a selectable marker trait that eases identification of a functional construct.

In addition to a gene comprising a 3' termination sequence of the invention, multiple gene expression cassettes also contain a marker gene known to be functional in the plant expression system, preferably linked to a constitutive promoter. The nucleotide sequence encoding the marker is typically flanked on the 5' side by functional regulatory sequences, as described below, and flanked on the 3' side by a 3' termination sequence that is functional in a plant expression system. Exemplary 3' termination sequences that function in plants include the nopaline synthase 3' termination sequence, and the octopine T-DNA gene 7 3' termination sequence. Alternatively, the 3' termination sequence can be provided by the marker gene, if the 3' termination sequence of the gene is functional in the plant system being transformed.

In the single gene expression cassette construct, the marker trait is used to identify both transformed cells and functional 3' termination sequences. The drawback of this strategy is that successfully transformed cells may nonetheless fail to display the marker trait because the 3' termination sequence being tested does not function in the plant expression system. Conversely, while the multiple gene expression cassette is designed to allow for identification of all successfully transformed cells, it does not readily indicate functionality of the 3' termination sequence being tested, unless the test 3' termination sequence is flanking a sequence for expression of a different marker trait than the accompanying marker gene known to be functional. Therefore, in both scenarios, a method of physically detecting the presence, and preferably the orientation, of the gene comprising the 3' termination sequence being tested is also desirable.

Such physical techniques typically are known in the art and typically take the form of blotting assays, such as Northern and Southern blotting and the like, where oligonucleotide probes specific for the gene comprising the 3' termination sequence being tested are hybridized to RNA or DNA isolated from the transformed cell or it's progeny. Using stringent hybridization conditions, only sequences of the isolated DNA derived from the expression cassette will be bound by the probes and identified. Another physical method involves sequencing the incorporated chimeric test gene. To facilitate the process, restriction sites can be engineered into the expression cassette, allowing for ready isolation of the oligonucleotide to be sequenced.

A. Standard Methods

Standard techniques for construction of the chimeric genes incorporated into the expression cassettes of the present invention are well known to those of ordinary skill in the art (Sambrook, J., Fritsch, E. F., and Maniatus, T., *Molecular Cloning, A Laboratory Manual* 2nd ed. (1989); Gelvin, S. B., Schilperoort, R. A., Varma, D. P. S., eds. *Plant Molecular Biology Manual* (1990)). A variety of strategies are available for ligating fragments of DNA, the choice of which depends on the nature of the termini of the DNA fragments. Preferred constructs will generally include a plant promoter. Suitable promoters include any constitutive, inducible, tissue or organ specific, or developmental stage specific promoter which can be expressed in the particular plant cell. Suitable such promoters are disclosed in Weising et al., supra. The following is a partial representative list of promoters suitable for use herein: the CaMV 35S promoter (Odell, J. T., Nagy, F., Chua, N. H., *Nature,* 313:810-812 (1985)), the CaMV 19S (Lawton, M. A., Tierney, M. A., Nakamura, I., Anderson, E., Komeda, Y., Dube, P., Hoffman, N., Fraley, R. T., Beachy, R. N., *Plant Mol. Biol.,* 9:315-324 (1987)), nos (Ebert, P. R., Ha, S. B., An. G., *PNAS,* 84:5745-5749 (1987)), Adh (Walker, J. C., Howard, E. A., Dennis, E. S., Peacock, W. J, *PNAS,* 84:6624-6628 (1987)), sucrose synthase (Yang, N. S., Russell, D., *PNAS,* 87:4144-4148 (1990)), α-tubulin, actin (Wang, Y., Zhang, W., Cao, J., McEhoy, D. and Ray Wu., *Molecular and Cellular Biology,* 12:3399-3406 (1992)), cab (Sullivan, T. et al., *Mol. Gen. Genet,* 215:431-440 (1989)), PEPCase (Hudspeth, R. L. and J. W. Grula., *Plant Mol Biol.,* 12:579-589 (1989)) or octopine synthase (OCS) promoters, the light-inducible promoter from the small subunit of ribulose bisphosphate carboxylase (Khoudi, et al., *Gene,* 197:343 (1997)) and the mannopine synthase (MAS) promoter (Velten et al., *EMBO J.,* 3:2723-2730 (1984); Velten & Schell, *Nucleic Acids Research,* 13:6981-6998 (1985)). Tissue specific promoters such as root cell promoters (Zhang & Forde, *Science,* 279:407 (1998); Keller, et al., *The Plant Cell,* 3(10): 1051-1061 (1991); Conkling, M. A., Cheng, C. L., Yamamoto, Y. T., Goodman, H. M., *Plant Physiol.,* 93:1203-1211 (1990)) and tissue specific enhancers (Fromm M. E., Taylor L. P., Walbot V., *Nature,* 312:791-793 (1986)) are also contemplated to be particularly useful, as are inducible promoters such as ABA- and turgor-inducible promoters. Still other promoters are wound-inducible and typically direct transcription not just on wound induction, but also at the sites of pathogen infection. Examples are described by Xu et al., *Plant Mol. Biol.,* 22:573-588 (1993); Logemann et al., *Plant Cell,* 1:151-158 (1989); and Firek et al., *Plant Mol. Biol.,* 22:129-142 (1993). The skilled artisan will recognize that the subject promoters and parts thereof, can be provided by other means, for example chemical or enzymatic synthesis analogous to that described above for construction of 3' termination sequences.

In the construction of heterologous promoter/structural gene combinations, the promoter is preferably positioned about the same distance from the heterologous transcription start site as it is from the transcription start site in its natural setting. As is known in the art, however, some variation in this distance can be accommodated without loss of promoter function and indeed may be necessary when the heterologous construct comprises elements from different genera.

Several methods for isolation of promoters are known. For instance, the full length of a promoter sequence may be isolated if a portion of the promoter or the corresponding gene sequence is known. One skilled in the art will recognize that a variety of small or large insert genomic DNA libraries may be screened using hybridization or polymerase chain reaction (PCR) technology to identify library clones containing the desired sequence. Typically, the desired sequence may be used as a hybridization probe to identify individual library clones containing the known sequence. Alternatively, PCR primers based on the known sequence may be designed and used in conjunction with other primers to amplify sequences adjacent to the known DNA polynucleotide sequence. Library clones containing adjacent DNA sequences may thereby be identified. Restriction mapping and hybridization analysis of the resulting library clones' DNA inserts allows for identification of the DNA sequences adjacent to the known DNA polynucleotide sequence. Thus, promoters may be isolated if only a portion of a promoter sequence is known.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNA's, from suitable eukaryotic genes, or from a synthetic gene sequence. The present invention is not limited to constructs, as presented in the following examples. Rather, the non-translated leader sequence can be part of the 5' end of the non-translated region of the coding sequence for the virus coat protein, or part of the promoter sequence, or can be derived from an unrelated promoter or coding sequence. In any case, it is preferred that the sequence flanking the initiation site conform to the translational consensus sequence rules for enhanced translation initiation reported by Kozak, M., *Nature*, 308:241-246 (1984) and, of course, be functional in plants. Regulatory elements such as Adh intron 1 (Callis, J. Fromm, M. and Walbot, V., *Genes and Develop.*, 1:1183-1200 (1987)), sucrose synthase intron ("Mutagenesis of Cultured Cells" by P. J. King, *Cell Culture and Somatic Cell Genetics of plants*, Chapter 61, vol. 1, By I. K. Vasil, (Ed.) Academic Press, Inc., Orlando 1984, pp. 547-549) or TMV omega element (Gallie et al., *Nucl. Acids Res.*, 15:8693-8711 (1987)), may further be included where desired.

In preparing the expression cassette, the various DNA sequences may normally be inserted or substituted into a bacterial plasmid. Any convenient plasmid may be employed, which will be characterized by having a bacterial replication system, a marker which allows for selection in the bacterium and generally one or more unique, conveniently located restriction sites. These plasmids, referred to as vectors, may include such vectors as pACYC184, pACYC177, pBR322, pUC9, the particular plasmid being chosen based on the nature of the markers, the availability of convenient restriction sites, copy number, and the like. Thus, the sequence may be inserted into the vector at an appropriate restriction site(s), the resulting plasmid used to transform the *E. coli* host, the *E. coli* grown in an appropriate nutrient medium and the cells harvested and lysed and the plasmid recovered. One then defines a strategy that allows for the stepwise combination of the different fragments.

As necessary, the fragments may be modified by employing synthetic adapters, adding linkers, employing in vitro mutagenesis or primer repair to introduce specific changes in the sequence, which may allow for the introduction of a desired restriction site, for removing superfluous base pairs, or the like. By appropriate strategies, one desires to minimize the number of manipulations required as well as the degree of selection required at each stage of manipulation. After each manipulation, the vector containing the manipulated DNA may be cloned, the clones containing the desired sequence isolated, and the vector isolated and purified. As appropriate, hybridization, restriction mapping or sequencing may be employed at each stage to ensure the integrity and correctness of the sequence.

B. Coding Sequences

Non-Plant Genes

The coding region of genes comprising the expression cassettes of the present invention can be isolated from virtually any source, including but not limited to animal, viral, fungal and bacterial species, in addition to plants and genes normally associated with cellular organelles such as mitochondria and chloroplasts. Coding regions may also comprise chimeric genes and genes derived from ligating genomic regions of two or more gene sequences together to construct novel heterologous genes. Genomic sequences used in forming heterologous genes need not be isolated from a biological source, by may be designed in silico and produced chemically prior to incorporation into the expression cassette. Coding regions may be free of intronic sequences, or further comprise introns that are functionally recognized by the species to be transfected. Expression cassettes will typically include restriction enzyme sites at the 5' and 3' ends of the cassette to allow for easy insertion of genes into a pre-existing vector.

By way of example, bacterial genes with insecticidal properties can be incorporated into the expression cassette. (e.g., de Maagd, R. A., et al., "Bacillus thuringiensis toxin-mediated Insect Resistance in Plants", *Trends in Plant Sci.*, 4(1):9-13 (1999); Fishhoff, D. A. and Bondish. K. S., "Insect tolerant transgenic tomato plants", *Bio/Technology*, 5:807-813 (1987), U.S. Pat. No. 5,952,485 "Procedures and materials for Conferring Disease Resistance in Plants"). Other embodiments comprise antisense sequences capable of hybridizing to mRNA sequences thereby inducing "gene silencing", as applied for example to the control of fruit ripening. (U.S. Pat. No. 5,545,815). Still other embodiments provide methods for transfecting avian genes such as those for ovalbumin or a-actin, mammalian genes, such as human-EGF, or proteases such as trypsin and papain. Any coding construct of the present invention may be modified prior to transfection, either by molecular biological, chemical or other methods known in the art, to produce genes encoding proteins with enhanced or novel activities, targeting capabilities or extended biological half-lives, or simply to impart a codon set which is more efficiently utilized by the prospective transfected plant. An additional embodiment comprises entirely synthetic genes designed in silico from stored database sequences. Such synthetic genes may comprise functional domains from diverse molecules, imparting a unique set of properties to the transcribed protein.

Selectable Marker Genes

For purposes of screening successfully transfected cells and/or 3' termination sequences functional in plants, polynucleotides encoding selectable markers can be used in constructing the chimeric gene(s) of an expression cassette in the present invention. Alternatively, the selectable marker may be carried on a separate piece of DNA and used in a co-transformation procedure with the expression cassette comprising the 3' termination sequence to be tested. Selectable markers are operably linked with appropriate regulatory sequences to enable expression in plants, in addition to the 3' termination sequence to be tested or a 3' termination sequence known to function in plants.

Selectable marker genes can be isolated from any source and encode a variety of selectable traits. For example, one can employ antibiotic resistance genes, e.g., a kanamycin resistance gene or methotrexate resistance gene (DHFR). These genes are described in Haas and Dowding, "Aminoglycoside-Modifying Enzymes", *Meth. Enzymology*, 43:611-628 (1975), and Bourouis et al., *EMBO J.*, 2:1099-1104(1983). Additional genes include chromogenic substrates; a luciferase (lux) coding region (Ow et al., *Science*, 234:856 (1986)), which allows for bioluminescence detection; an aequorin coding region (Prasher et al., *Biochem. Biophys. Res. Comm.*, 126:1259 (1985)), which may be employed in calcium-sensitive bioluminescence detection, or a green fluorescent protein coding region (Niedz et al., *Plant Cell Reports*, 14:403 (1995)); the chloramphenicol acetyl transferase gene (cat) from Tn9 of *E. coli*, the beta-glucuronidase gene (gus) of the uida locus of *E. coli;* the nptII gene which confers resistance to kanamycin (Messing & Vierra, *Gene*, 19:259-268 (1982); and Bevan et al., *Nature*, 304:184-187 (1983)), the bar gene which confers resistance to the herbicide phosphinothricin (White et al., *Nucl. Acids Res.*, 18:1062 (1990); Spencer et al., *Theor. Appl. Genet.*, 79:625-631 (1990)), and the hph gene which confers resistance to the antibiotic hygromycin (Blochlinger and Diggelmann, *Mol. Cell. Biol.*, 4:2929-2931 (1984)). Other markers are disclosed in K. Weising et al., *Ann. Rev. of Genetics*, 22:421 (1988). More recently, a number of selection systems have been developed which do not rely of selection for resistance to antibiotic or herbicide. These include the inducible isopentyl transferase system described by Kunkel et al., *Nature Biotechnol.*, 17:916-919 (1999).

Expression of the selectable marker is determined at a suitable time after the DNA has been introduced into the recipient cells. A preferred assay entails the use of the *E. coli* beta-glucuronidase (GUS) gene (R. Jefferson et al., *EMBO J.*, 16:3901 (1987)). Plant cells transformed and expressing this gene will stain blue upon exposure to the substrate, 5-bromo-4-chloro-3-indolyl-β-D-glucuronide (X-GLUC), and can also be used to quantify the amount of transient or stable protein expression attributable to a specific vector system (Rhodes C A et al., *Methods Mol Biol*, 55:121-131 (1995)). Thus, in one aspect, the present invention relates to an expression cassette that carries a construct encoding a GUS gene terminated by a 3' termination sequence of the present invention capable of introduction into the genome of, and expression in, a plant. This aspect of the invention is illustrated in FIG. 1, which illustrates the results of a test for functionality of yeast 3. ends in *Agrobacterium*-infiltrated *Nicotiana benthamiana* leaves. Plant binary expression cassettes were constructed containing the following genetic elements: the dMMV promoter linked to the beta-glucuronidase (GUS) reporter gene linked to a 3' end. The *Arabidopsis* EF1A 3 end served as the positive control plant 3' end, whereas an expression cassette with no 3' end served as the negative control. The vectors were transformed into *Agrobacterium tumefaciens* and used to infect *N. benthamiana* leaves. The infected leaves were stained for expression of the GUS reporter gene using a histochemical substrate, and then the green chlorophyll was removed from the leaves with ethanol. In the figure, the SPS1 and CAL1 yeast 3' ends appear to function as well or better than the plant EF1A 3' end, and the KRE9 3' end works slightly less well than the plant EF1A 3' end.

Another aspect of the present invention relates to an expression cassette that carries a construct encoding an nptII gene terminated by a 3' termination sequence of the present invention capable of introduction into the genome of, and expression in, a plant. This aspect of the invention is illustrated in FIGS. 2 and 3.

FIG. 2 depicts the functionality of yeast 3' termination sequences in the expression of kanamycin resistance in tobacco hairy roots. Plant binary vectors were constructed containing the following genetic elements: the dMMV promoter linked to the nptII selectable marker gene linked to a 3' termination sequence. The *Arabidopsis* EF1A 3' termination sequence served as the positive control plant 3' termination sequence. The vectors were transformed into *Agrobacterium rhizogenes* and used to infect tobacco leaf pieces. Successful transformation and root out-growth is an indication of the level of kanamycin resistance conferred by the selectable marker elements. The plates in the top row contain no kanamycin, whereas the plates in the bottom row contain 75 micrograms per milliliter kanamycin. Some variability in response is observed due to differences in the leaf explant material used for each transformation. Therefore, it is most informative to compare the number of root initials formed between the top and bottom plate for each construct.

The CAL1 yeast 3' termination sequence appears to function about as well as the plant EF1A3' termination sequence, the SPS and KRE9 3' termination sequences works reasonably well compared to the plant EF1A 3' termination sequence.

FIG. 3 depicts the functionality of yeast 3' termination sequences in the expression of kanamycin resistance in tobacco shoots. Plant binary vectors were constructed which contained the following genetic elements: the dMMV promoter linked to the nptII selectable marker gene linked to a 3' termination sequence. The *Arabidopsis* EF1A 3' termination sequence served as the positive control plant 3' termination sequence. The vectors were transformed into *Agrobacterium tumefaciens* and used to infect tobacco leaf pieces. Successful transformation and shoot out-growth is an indication of the level of kanamycin resistance conferred by the selectable marker elements. The plates in the top row contain no kanamycin, whereas the plates in the bottom row contain 75 micrograms per milliliter kanamycin. Some variability in response is observed due to differences in the leaf explant material used for each transformation. Therefore, it is most informative to compare the number of shoots formed between the top and bottom plate for each construct. Additional experiments confirm the general trends that are seen in the above photos.

The CAL1, SPS, and KRE9 yeast 3' termination sequences appear to function about as well as the plant EF1A3' termination sequence (poor explant material).

In addition to providing expression cassettes for monitoring cellular transformation and 3' termination sequence functionality in plants, the present invention also provides cassettes for the expression of any nucleic acid encoded trait, including antisense constructs for suppressing endogenous gene expression. Typically, however, the coding region will express a protein.

III. Identifying Plant Expression Cassettes Constructed with Non-Plant 3' Termination Sequences To confirm the presence of the exogenous 3' termination sequences in plant cells, a variety of assays may be performed. Such assays include, for example, "molecular biological" assays, including Southern and Northern blotting, and PCR; "biochemical" assays, such as detecting the presence of a protein product, e.g., by immunological means (ELISAs and Western blots) or by enzymatic function; plant part assays, such as leaf or root assays; and also, by analyzing the phenotype of a whole regenerated plant. Constructs may also be engineered to ease isolation of all or part of the heterologous expression system, which can then be subjected to nucleic acid sequencing analysis.

A. In vitro Assay Systems

Genomic DNA may be isolated from plant cell lines or any plant parts to determine the presence of the exogenous gene through the use of techniques well known to those skilled in the art. Note that intact sequences will not always be present, presumably due to rearrangement or deletion of sequences in the cell.

The presence of DNA elements introduced through the methods of this invention may be determined by polymerase chain reaction (PCR). Using this technique, discreet fragments of DNA are amplified and detected by gel electrophoresis. This type of analysis permits one to determine whether a gene is present in a stable transformant, but does not prove integration of the introduced gene into the host cell genome. It is not possible using PCR techniques to determine whether transformants have exogenous genes introduced into different sites in the genome, i.e., whether transformants are of independent origin. It is contemplated that by using PCR techniques it would be possible to clone fragments of the host genomic DNA adjacent to an introduced gene.

Positive proof of DNA integration into the host genome and the independent identities of transformants may be determined using the technique of Southern hybridization. Using this technique, specific DNA sequences that were introduced into the host genome and flanking host DNA sequences can be identified. Hence the Southern hybridization pattern of a given transformant serves as an identifying characteristic of that transformant. In addition, it is possible through Southern hybridization to demonstrate the presence of introduced genes in high molecular weight DNA, i.e., confirm that the introduced gene has been integrated into the host cell genome. The technique of Southern hybridization provides information that is obtained using PCR e.g., the presence of a gene, but also demonstrates integration into the genome and characterizes each individual transformant.

It is contemplated that using the techniques of dot or slot blot hybridization, which are modifications of Southern hybridization techniques, one could obtain the same information that is derived from PCR, e.g., the presence of a gene.

Both PCR and Southern hybridization techniques can be used to demonstrate transmission of a transgene to progeny. The nonchimeric nature of the callus and the parental transformants ($R_0$) is demonstrated by germline transmission and identical Southern blot hybridization patterns and intensities of the transforming DNA in callus, $R_0$ plants, and $R_1$ progeny that segregated for the transformed gene.

Whereas DNA analysis techniques may be conducted using DNA isolated from any part of a plant, RNA will only be expressed in particular cells or tissue types and hence it will be necessary to prepare RNA for analysis from these tissues. PCR techniques may also be used for detection and quantitation of RNA produced from introduced genes. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridization. These techniques are modifications of Northern blotting and will only demonstrate the presence or absence of an RNA species.

B. Biochemical Assay Systems

While Southern blotting and PCR may be used to detect the gene(s) in question, they do not provide information as to whether the gene is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focussing, or by chromatographic techniques such as ion exchange or gel exclusion chromatography. The unique sequences and structures of individual proteins offer opportunities for use of specific antibodies to detect their presence in formats such as an ELISA assay. Combinations of approaches may be employed with even greater specificity such as western blotting in which antibodies are used to locate individual gene, products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabelled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins that have changes in amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays. An example is to evaluate resistance to antibiotics.

IV. Selection of Transformants

Once plant cells have been transformed with the expression cassette as described supra, it is necessary to identify and select cells that both contain the recombinant DNA and still retain sufficient regenerative capacity. There are two general approaches that have been found useful for accomplishing this. First, the transformed cells or plants regenerated therefrom can be screened for the presence of the recombinant DNA by various standard methods which could include assays for the expression of selectable markers or assessment of phenotypic effects of the recombinant DNA, if any, as described above. Alternatively, and preferably, when a selectable marker gene has been transmitted along with or as part of the recombinant DNA, those cells that have been transformed can be identified by the use of a selective agent to detect expression of the selectable marker gene, as exemplified in FIGS. 2 and 3.

V. Transgenic Plants

Transformed plant cells derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., "Protoplasts Isolation and Culture", *Handbook of Plant Cell Culture*, pp. 124-176, Macmillan Publishing Company, New York (1983); and Binding, "Regeneration of Plants", *Plant Protoplasts*, pp. 21-73, CRC Press, Boca Raton (1985). Regeneration can also be obtained from plant callus, explants, organs, or parts thereof. Such regeneration techniques are described generally in Klee et al., *Ann. Rev. of Plant Phys.*, 38:467-486 (1987).

A. Transfection Techniques

Expression cassettes of the invention may be introduced into the genome of the desired plant host by a variety of conventional techniques. For example, the cassette may be introduced directly into the genomic DNA of the plant cell using techniques such as electroporation and microinjection of plant cell protoplasts, or the DNA constructs can be introduced directly to plant tissue using ballistic methods, such as DNA particle bombardment. DNA can be stably incorporated into cells or can be transiently expressed using methods known in the art. Stably transfected cells can be prepared by transfecting cells with an expression vector having a selectable marker gene, and growing the transfected cells under conditions selective for cells expressing the marker gene. To prepare transient transfectants, cells are transfected with a reporter gene to monitor transfection efficiency. A review of the general techniques can be found in articles by Potrykus (*Annu. Rev. Plant Physiol. Plant Mol. Biol.*, 42:205-225 (1991)) and Christou (*Agri-Food-Industiy Hi-Tech* Mar./Apr. 17-27, 1994).

DNA can also be introduced into plants by leaf disk transformation-regeneration procedures as described by Horsch et al., *Science*, 227:1229-1231 (1985), and other methods of transformation such as protoplast culture (Horsch et al., *Science*, 223:496 (1984); DeBlock et al., *EMBO J.*, 2:2143 (1984); Barton et al., *Cell*, 32:1033 (1983)) can also be used and are within the scope of this invention.

Microinjection techniques are known in the art and thoroughly described in the scientific and patent literature. The introduction of DNA constructs using polyethylene glycol precipitation is described in Paszkowski et al., *Embo. J.*, 3:2717-2722 (1984). Electroporation techniques are described in Fromm et al., *Proc. Natl. Acad. Sci. USA*, 82:5824 (1985). Ballistic transformation techniques are described in Klein et al., *Nature*, 327:70-73 (1987). Other methods are also available for the introduction of expression vectors into plant tissue, e.g., electroinjection (Nan et al., In "*Biotechnology in Agriculture and Forestry*," Ed. Y. P. S. Bajaj, Springer-Verlag Berlin Heidelberg, 34:145-155 (1995); Griesbach, *HortScience*, 27:620 (1992)); fusion with liposomes, lysosomes, cells, minicells or other fusible lipid-surfaced bodies (Fraley et al., *Proc. Natl. Acad. Sci. USA*, 79:1859-1863 (1982)); polyethylene glycol (Krens et al., *Nature*, 296:72-74 (1982)); chemicals that increase free DNA uptake; transformation using virus, and the like.

Alternatively, expression cassettes may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example, Horsch et al., *Science*, 233:496-498 (1984), and Fraley et al., *Proc. Natl. Acad. Sci. USA*, 80:4803 (1983) and *Gene Transfer to Plants*, Potrykus, ed. (Springer-Verlag, Berlin 1995).

Alternatively, to enhance integration into the plant genome, terminal repeats of transposons may be used as borders in conjunction with a transposase. In this situation, expression of the transposase should be inducible, so that once the transcription construct is integrated into the genome, it should be relatively stably integrated and avoid further transposition.

One of skill will recognize that after the expression cassette is stably incorporated into transgenic plants and confirmed to be operable, it can be introduced into other plants by sexual crossing. Any of a number of standard breeding techniques can be used, depending upon the species to be crossed.

Using known procedures, one of skill can screen for plants of the invention by detecting the increase or decrease of marker mRNA or protein in transgenic plants or expression of marker traits by the transgenic plant. Alternative embodiments of the present invention allow for detection of target gene mRNA, protein or other trait, in which case the optional marker genes can be omitted from the expression cassette. Methods for detecting and quantitation of mRNAs and proteins as well as screening assays for such traits as antibiotic resistance are well known in the art.

B. Site-Directed Integration

Non-plant 3' termination sequences are particularly suited to applications requiring heterologous recombination between elements in the expression cassette and elements present in the host cell genome. Unlike commonly used plant 3' termination sequences, non-plant 3' termination sequences of the present invention have no homologous counterparts in the host cell genome. Consequently, non-plant 3' termination sequences are not prone to inadvertent integration into the host cell genome by homologous recombination at the site of a 3' termination sequence homologue. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (Offringa et al., (1996), U.S. Pat. No. 5,501,967, the entire contents of which are herein incorporated by reference). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

Where homologous recombination is desired, the targeting vector used may be of the replacement- or insertion-type (Offringa et al. (1996), supra). Replacement-type vectors generally contain two regions which are homologous with the targeted genomic sequence and which flank a heterologous nucleic acid sequence, e.g., a selectable marker gene sequence. Replacement-type vectors result in the insertion of the selectable marker gene thereby disrupting the targeted gene. Insertion-type vectors contain a single region of homology with the targeted gene and result in the insertion of the entire targeting vector into the targeted gene.

C. Producing Transgenic Plants

The transformed plant cell, usually in the form of a callus culture, leaf disk, explant or whole plant (via the vacuum infiltration method of Bechtold et al., *C. R. Acad. Sci. Paris*, 316:1194-1199 (1993)) is regenerated into a complete transgenic plant by methods well-known to one of ordinary skill in the art (e.g., Horsh et al., 1985).

Using these methods, virtually any gene, regardless of source, can be incorporated into the expression cassettes of the present invention for use in creating transgenic plants. The non-plant 3' termination sequences claimed herein are particularly useful for this purpose. In addition to failing to recombine with endogenous nucleotide sequences as noted above, the lack of homology between the 3' termination sequences of the present invention and native plant 3' termination sequences also reduces the possibility of gene silencing through interference with transcripts comprising host 3' termination sequences. Similarly, because of the heterologous nature of the 3' termination sequences used in the claimed expression cassettes, transgenic plants created using these cassettes are genetically extremely stable and the genetic traits encoded by the cassettes segregate in a predictable manner. Thus transgenic plants created using the present invention can be readily crossed with other stably transformed transgenic plants to create new transgenic plant strains having genomic stability equal to their parental plants.

It may also be desirable to express a nucleic acid sequence that encodes an antisense RNA that hybridizes with a genomic plant DNA sequence. For example, it may be of advantage to express antisense RNA that is specific for genomic plant DNA sequences that encode an enzyme whose activity is sought to be decreased. Examples of DNA sequences whose reduced expression may be desirable are known in the art including, but not limited to, the ethylene inducible sequences in fruits (U.S. Pat. No. 5,545,815, the entire contents of which are herein incorporated by reference). Expression of antisense RNA that is homologous with these ethylene inducible sequences is useful in delaying fruit ripening and in increasing fruit firmness. Other DNA sequences whose expression may be desirably reduced include the ACC synthase gene, which encodes the enzyme that is the first and rate limiting step in ethylene biosynthesis. Nucleic acid sequences for this gene have been described from a number of plant sources (e.g., Picton et al., *The Plant J.*, 3:469-481 (1993); U.S. Pat. Nos. 5,365,015 and 5,723,766, the contents of both of which are herein incorporated by reference). Expression of antisense RNA that hybridizes with ACC synthase genomic sequences in plants may be desirable to delay fruit ripening.

One of skill in the art knows that the antisense DNA segment to be introduced into the plant may include the full-length coding region of the targeted gene or a portion thereof. Complete homology between the nucleotide sequences of the antisense RNA and the targeted genomic DNA is not required. Rather, antisense DNA sequences which encode antisense RNA sequences that are partially homologous to a targeted genomic DNA sequence are contemplated to be within the scope of the invention so long as the antisense RNA sequences are capable of repressing expression of the target genomic DNA sequence.

Also included within the scope of this invention are vectors that contain the same or different nucleic acid sequences under the transcriptional control of different 3' termination sequences, and other sequences. Such vectors may be desirable to, for example, to control different levels of expression of different nucleic acid sequences of interest in plant tissues.

EXAMPLES

The following examples are offered to illustrate, but not to limit the claimed invention.

Example 1

Isolation and Amplification of *Saccharomyces cerevisiae* CAL1 3' Termination Sequence Studies by the applicants have shown that at least three 3' termination sequences isolated from the yeast *Saccharomyces cerevisiae* function in plants as part of a heterologous expression cassette. The present example describes the isolation of one of these sequences by PCR amplification.

Oligonucleotide primers for PCR amplification were synthesized on an Applied Biosystems 394 DNA synthesizer using established phosphoramidite chemistry, precipitated with ethanol according to standard protocols, and used in the amplification reaction without further purification. The sequences of the synthetic primers were:

```
                                                 SEQ ID. NO:4
        5'-GCGCGCGGAAGGAGGAAAGTGACTCCTTCGTTGC-3'

SEQ ID. NO:5
        5'-GGTACCTCATCATTTGGAGGTTCAAGTCATGGAG-3'
```

A BssH II restriction site (5'-GCGCGC-3') and an Asp718 I restriction site (5'-GGTACC-3') were incorporated at the ends of the SEQ ID. NO:4 and SEQ ID. NO:5 primers, respectively, to facilitate subcloning of the PCR-amplified 3' termination sequences into various plant expression cassettes.

The CAL1 3' termination sequence (~485 bp) was amplified from the yeast chitin synthase 3 gene (GENBANK accession number X57300; SEQ ID NO:81). PCR reactions were performed by mixing the primers with ~100 nanograms of *S. cerevisiae* genomic DNA prepared with a DNeasy™ Plant Mini Kit according to the manufacturer's (Qiagen) instructions. The primers were added to a final concentration of 1 µM each to a mixture containing 10 mM TrisHCl (pH8.8), 25 mM KCl, 3.5 mM $MgCl_2$, 2.5 mM each deoxynucleoside triphosphate, 0.001% gelatin, 1.5 U AmpliTaq DNA Polymerase (Perkin-Elmer/Cetus), and the genomic DNA. Following 5 min denaturation at 95° C., the cycling conditions were 95° C. for 1 min, 45° C. for 1 min 30 s, and 72° C. for 30 s for 45 cycles. PCR products were T-A cloned into the pCR2.1-Topo cloning vector according to the manufacturer's (Invitrogen) instructions. Cloning of the correct 3' end was confirmed by comparison of the Topo clone sequences to the sequence reported in GENBANK entry X57300 (SEQ ID NO:81).

Example 2

Construction of a Recombinant Expression Cassette Using the CAL1 3' Termination Sequence and Testing Non-Plant 3' Termination Sequence Function in Plants This example describes the construction of a reporter expression cassette for testing 3' termination sequence functionality in plants. The reporter expression cassette comprises a dMMV promoter (Dey and Maita, Plant Mol Biol 40: 771-782 1999) operably linked to a β-glucuronidase (GUS) reporter gene containing a plant intron and a glycine-rich protein signal peptide secretion signal (Jefferson et al., PCT WO99/13085). The Cal1 3' end was sub-cloned from the pCR2.1-Topo vector as a BssH II-Asp718 I fragment into the BssH II-Asp 718 I sites of the plant binary vector pMAXY-3768 (Right border-dMMV promoter-GFP-[BssH II]Arabidopsis EF1a 3' end[Asp718 I]-Left border). The "GUSplus+intron+SP" sequences derived from pCAMBIA1305.2 were subcloned from pMAXY-3568 as an Nco I-Asc I fragment into the Nco I-BssH II sites of the above vector to remove the GFP gene and insert the GUS reporter gene. The 3' termination sequence to be tested was operably linked to the GUS reporter sequence and located 20 nucleotides downstream of the GUS stop codon. The completed expression cassette was then used to transform competent Agrobacterium tumefaciens cells. Leaf tissue was infected with the recombinant A. tumefaciens using a transformation procedure modified from Horsch et al Science 227:1229-1231 (1985), and the expression of β-glucuronidase is monitored by histochemical and fluorometric assays.

In an exemplary construct, a Saccharomyces cerevisiae CAL1 3' termination sequence, amplified as described in example 1, was inserted into the reporter expression cassette 3' to the reporter gene. Two control reporter expression cassette constructs were also produced: a positive control vector comprising an Arabidopsis EF1A 3' termination sequence, and a negative control lacking a 3' termination sequence of any type.

All three vectors were transformed into Agrobacterium tumefaciens strain C58. Successfully transfected Agrobacterium colonies were clonally selected based on the Kanamycin resistance encoded by the vector nptIII gene. Briefly, A. tumefaciens transformed with each vector were plated on LB+KAN plates [per liter of medium: 10 g bacto-tryptone, 5 g bacto-yeast extract, 10 g NaCl, adjust pH to 7.0 with NaOH, 1.5% bacto-agar, plus 40 µg/ml Kanamycin (Phyto-Technology Laboratories)] and allowed to incubate at 30° C. for 48 hours. Two clones from each transformation were picked from the plates and suspended in three ml of LB+KAN liquid media (as above without agar). The bacterial cultures were grown overnight at 30° C. with rapid shaking (250 rpm).

The saturated bacterial cultures were pelleted by centrifugation at 3500 rpm in an Eppendorf 5810 R centrifuge. The supernatants were decanted and the bacterial pellets resuspended in 3 ml of 10 mM Mg SO$_4$. Samples from each clonal selection were used to infect separate, discrete areas on the same Nicotiana benthamiana leaf. Inoculation involved forcing between 100 to 250 microliters of bacterial suspension into the interstitial leaf spaces using a syringe (no needle) placed in direct contact with the underside of the leaf. The infected leaf, still attached to the plant, was allowed to incubate for 4 days at room temperature prior to staining with 5-bromo-4-chloro-3-indolyl-beta-D-glucuronide (X-GLUC) according to the method described by R. Jefferson et al., EMBO J., 16, 3901 (1987). Chlorophyll was then removed from the tissue by treatment with 70% ethanol at room temperature for 2 days. The ethanol was repeatedly replaced with fresh stock as it turned green from the extracted chlorophyll. Test results are depicted in Table 2. Relative levels of GUS expression are depicted by the number of "+" present in each column.

TABLE 2

Functionality of S. cerevisiae CAL1 3' termination sequence in Agrobacterium-infected Nicotiana Benthamiana leaves

| 3' Termination Sequence | GUS expression |
|---|---|
| EF1A | +++ |
| CAL1 | ++++ |
| no 3' termination sequence | -- |

From this inquiry, it is apparent that the S. cerevisiae CAL1 termination sequence is capable of supporting gene expression in plants, without overt modification.

Comparative studies with S. cerevisiae SPS1 and KRE9 3' termination sequences also yielded positive results when incorporated into the reporter expression cassette as described in the method above. Expression of the reporter gene, however, appeared to be stronger for the construct comprising the CAL1 termination sequence than from constructs using either of the other two S. cerevisiae termination sequences (e.g., see FIG. 1).

Example 3

Constructing a Heterologous 3' Termination Sequence that is Functional in Plants from the 3' Termination Sequence from Human Genes The following primer sets were used to PCR amplify 3' termination sequences from the genomic sequences corresponding to the indicated GENBANK accession numbers by using the PCR amplification method described in example 1 above.

| PRIMER NAME | PRIMER SEQUENCE | GENBANK REFERENCE |
|---|---|---|
| hLaminLF (SEQ ID NO:10) | 5'- GGCGCGCCTAGGCCAAGCCCTGCGTCCAGCGAGC -3' | GENBANK AC#: M94363 (SEQ ID NO:66) |
| hLaminLR (SEQ ID NO:11) | 5'- CGGGGTACCCCGAGTCAGCTTGTGCAACAGCGTCG -3' | |
| hLaminSF (SEQ ID NO:56) | 5'- GGCGCGCCTAGGGAAGCCTGCACGCGGCAGTTC -3' | GENBANK AC#: M94363 (SEQ ID NO:66) |
| hLaminSR | 5'- CGGGGTACCCCGGAATAAACTCAGAGGCAGAAC -3' | |

-continued

| PRIMER NAME | PRIMER SEQUENCE | GENBANK REFERENCE |
|---|---|---|
| (SEQ ID NO:57) | | |
| hC2F (SEQ ID NO:58) | 5'- GGCGCGCCTAGGCTAGCCATGGCCACTGAGCCCT -3' | GENBANK AC#: L09708 (SEQ ID NO:67) |
| hC2R (SEQ ID NO:59) | 5'- CGGGGTACCCCGCCAAGGCCAGCCCTACCTGGC -3' | |
| UBQF (SEQ ID NO:60) | 5'- GGCGCGCCTAGGTGGCTGTTAATTCTTCAGTCATGGC -3' | GENBANK AC#: X04803 (SEQ ID NO:68) |
| UBQR (SEQ ID NO:61) | 5'- CGGGGTACCCCGCCTAACTTGTAATGACTTAAACAGC -3' | |

For the lamin gene, a long (L) and short (S) version of the 3' region were amplified. The human 3' termination sequences were cloned into a plant binary vector and tested for activity in the leaf infiltration assay as described above.

GUS activity of four human 3' termination sequences in the *N. benthamiana* leaf infiltration assay.

| 3' end | Specific Activity (RFU/min/ug) | Relative Activity |
|---|---|---|
| C2 | 0.15 | 0.2 |
| LAM S | 0.21 | 0.2 |
| UBQ | 0.43 | 0.4 |
| LAM L | 0.46 | 0.4 |
| EF1a | 1.02 | 1 |
| CAL1 | 1.66 | 1.6 |

All four of these human 3' termination sequences were weakly active and functional in the plant transient assay. The CAL1 3' termination sequence from *S. cerevisiae* (CAL1) and a 3' termination sequence from the *Arabidopsis* elongation factor 1a gene (EF1a) served as controls in this experiment.

Example 4

Constructing a Heterologous 3' Termination Sequence that is Functional in Plants from the 3' Termination Sequence of *Saccharomyces cerevisiae*

The following primer sets were used to PCR amplify 3' termination sequences from the genomic sequences corresponding to the indicated GENBANK accession numbers by using the PCR amplification method described in example 1 above.

| PRIMER NAME | PRIMER SEQUENCE | GENBANK REFERENCE |
|---|---|---|
| BDF1-5C1 (SEQ ID NO:32) | 5'- CCTAGGTGAAGAAGAGTGACTGAATTTTG -3' | GENBANK AC#: U18116 (SEQ ID NO:69) |
| BDF1-3N2 (SEQ ID NO:33) | 5'- GGTACCGTAAATTTTGTGAGTTAGGTTG -3' | |
| CHS5-5C1 (SEQ ID NO:34) | 5'- CCTAGGATTAATGGATGCCTTCAATGAG -3' | GENBANK AC#: Z49198 (SEQ ID NO:70) |
| CHS5-3N2 (SEQ ID NO:35) | 5'- GGTACCTAGAATGTGTTTAGGGATAGTTG -3' | |
| GSG1-5C1 (SEQ ID NO:36) | 5'- ACTAGTTAGCTTTATTGGATGACTTTATGG -3' | GENBANK AC#: U26674 (SEQ ID NO:71) |
| GSG1-3N2 (SEQ ID NO:37) | 5'- GGTACCAAGTGAAGATTTTGATTATACCAG -3' | |
| UBI2-5C1 (SEQ ID NO:38) | 5'- CCTAGGAATTGCGTCCAAAGAAGAAGTTG -3' | GENBANK AC#: X05729 (SEQ ID NO:72) |
| UBI2-3N2 (SEQ ID NO:39) | 5'- GGTACCATATTACGTTGACGGGAGTTTTC -3' | |
| IQG2-5C1 (SEQ ID NO:40) | 5'- CCTAGGAGTCCACTCTTCACCTCGTCTTG -3' | GENBANK AC#: X01474 (SEQ ID NO:73) |
| IQG2-3N2 (SEQ ID NO:41) | 5'- GGTACCTTTTCCCTTTTGGTAGTCAC -3' | |
| UBI3-5C1 (SEQ ID NO:42) | 5'- CCTAGGTAAGTGTCATTCCGTCTACAAG -3' | GENBANK AC#: X05730 (SEQ ID NO:74) |
| UBI3-3N2 (SEQ ID NO:43) | 5'- GGTACCTACACATGTCATCGCAGTGGAC -3' | |

-continued

| PRIMER NAME | PRIMER SEQUENCE | GENBANK REFERENCE |
|---|---|---|
| RPO2-5C1 (SEQ ID NO:44) | 5'- CCTAGGTGATATAGTATATCATCCTTACG -3' | GENBANK AC#: X03128 (SEQ ID NO:75) |
| RPO2-3N2 (SEQ ID NO:45) | 5'- GGTACCCTTAGGTGATATCGAGC -3' | |
| YEF3-5C1 (SEQ ID NO:46) | 5'- CCTAGGTGATGCTTACGTTTCTTCTGACG -3' | GENBANK AC#: J05583 (SEQ ID NO:76) |
| YEF3-3N2 (SEQ ID NO:47) | 5'- GGTACCGTGGCAGTTACTTTATATAGAGTG -3' | |

The 3' termination sequences were cloned into the same plant binary test vector as described in example 2 above (Right border-dMMV promoter-GUS+intron+SP reporter gene-Left border).

Functional analyses of the 3' termination sequences were conducted as described in Example 2 of the application (*Agrobacterium* infiltration into *N. benthamiana* leaves). Extracts were prepared from the infiltrated leaves and the GUS specific activity was determined using a quantitative fluorometric assay (essentially as described by Jefferson in Plant Molecular Biology Reporter 5(4): 387-405, 1987).

GUS activity of various *S. cerevisiae* 3' termination sequences in the *N. benthamiana* leaf infiltration assay.

| 3' end | Specific Activity (RFU/min/ug) | Relative activity |
|---|---|---|
| UBI3 | 0.18 | 0.3 |
| BDF1 | 0.24 | 0.4 |
| GSG1 | 0.42 | 0.7 |
| CHS5 | 0.46 | 0.7 |
| UBI2 | 0.50 | 0.8 |
| IQG2 | 0.64 | 1.0 |
| RPO2 | 0.97 | 1.6 |
| YEF3 | 1.07 | 1.7 |
| CAL1 | 0.40 | 0.7 |
| nos 3' | 0.61 | 1 |
| EF1a | 0.63 | 1 |

This transient assay system is quite variable due to the nature of the procedure, so the relative activities should be viewed as a rough estimate. The key point to note is that all of the *S. cerevisiae* 3' termination sequences tested were active and functional in plants. Some of the 3' ends were relatively weak, such as UBI3 and BDF1, whereas others (i.e. RPO2 and YEF3) had activity greater than the control plant 3' ends. 3' termination sequences from the *Agrobacterium* nopaline synthase gene (nos 3') and the *Arabidopsis* elongation factor 1a gene (EF1a) were used as controls in this experiment.

Example 5

Constructing a Heterologous 3' Termination Sequence that is Functional in Plants from the 3' Termination Sequence of *Aspergillus nidulans*

The following primer sets were used to PCR amplify 3' termination sequences from the genomic sequences corresponding to the indicated GENBANK accession numbers by using the PCR amplification method described in example 1 above.

| PRIMER NAME | PRIMER SEQUENCE | GENBANK REFERENCE |
|---|---|---|
| AOX-5C1 (SEQ ID NO:48) | 5'- CCTAGGAGTTTGTAGCCTTAGACATGAC -3' | pPICZα (Invitrogen) (SEQ ID NO:77) |
| AOX-3N2 (SEQ ID NO:49) | 5'- GGTACCGGTAATTAACGACACCCTAGAGG -3' | |
| NTBP-5C1 (SEQ ID NO:50) | 5'- CCTAGGTCTAAAGAGTAGCAATTCTGATG -3' | GENBANK AC#: U28333 (SEQ ID NO:78) |
| NTBP-3N2 (SEQ ID NO:51) | 5'- GGTACCACTTTGACGGAACAGAGGATGGAAG -3' | |
| NHYM-5C1 (SEQ ID NO:52) | 5'- CCTAGGACTGTTGCGTAGACATGAGC -3' | GENBANK AC#: AJ001157 (SEQ ID NO:79) |
| NHYM-3N2 (SEQ ID NO:53) | 5'- GGTACCAGTGCATTCCATGGATTCG -3' | |
| NACT-5C1 (SEQ ID NO:54) | 5'- CCTAGGATCGTCCACCGCAAGTGCTTC -3' | GENBANK AC#: M22869 (SEQ ID NO:80) |
| NACT-3N2 (SEQ ID NO:55) | 5'- GGTACCTGTATACTAGCAATACTGTAC -3' | |

The *Aspergillus* and *Pichia* 3' termination sequences were cloned into a plant binary vector and tested for activity in the leaf infiltration assay as described above.

GUS activity of three *A. nidulans* 3' termination sequences and one *P. pastoris* 3' termination sequence in the *N. benthamiana* leaf infiltration assay.

| 3' end | Specific Activity (RFU/min/ug) | Relative Activity |
| --- | --- | --- |
| NHYM | 0.21 | 0.4 |
| NACT | 0.21 | 0.4 |
| NTBP | 0.34 | 0.6 |
| AOX | 0.70 | 1.3 |
| nos 3' | 0.54 | 1 |
| CAL1 | 0.81 | 1.5 |
| EF1a | 1.39 | 2.6 |

All four of these fungal 3' termination sequences were active and functional to various degrees in the plant transient assay. A 3' termination sequence from the *Agrobacterium* nopaline synthase gene (nos 3') and a 3' termination sequence from the *Arabidopsis* elongation factor 1a gene (EF1a) served as controls in this experiment.

Example 6

Constructing a Synthetic, Heterologous 3' Termination Sequence that is Functional in Plants Using Oligonucleotide Primers This example provides a conceptual framework for building synthetic or semi-synthetic 3' termination sequences using oligonucleotide primers. It is meant to exemplify, but not to limit, the possible approaches that could be used to construct non-plant 3' termination sequences that have functionality in plants. As a first step in creating an upstream element, the following primers are designed and annealed together:

```
                                           SEQ ID NO:62
Up1CA    5'- AATTCTATGTATGTGTGTTTGTGTGTGTG -3'

SEQ ID NO:63
Up2NA    5'- AATTCACACACACACAAACACACACATACATAG -3'
```

When these 2 primers (containing a TAYRTA sequence and multiple TG repeats) anneal together, the double-stranded oligonucleotide pair forms EcoR I-compatible sticky ends that can be ligated into the EcoR I site of pBSSK+ (Stratagene). In the next step, a positioning element and downstream cleavage site are created by designing and annealing the following primers:

When these 2 primers (containing 2 copies of AATAAA followed by YA's at 10-40 nucleotides downstream) anneal together, the double-stranded oligonucleotide pair forms one Hind III-compatible end and one Xho I-compatible end that can be ligated into the Hind III and Xho I sites of the above pBSSK+ vector containing the engineered upstream region. Finally, additional spacer DNA can be added downstream of the cleavage site(s) by PCR amplification of a T-rich region from any yeast gene 3' end. The primers used for this purpose would be designed to introduce Xho I and Kpn I restriction sites at the 5' and 3' ends of the amplified nucleic acid, respectively. This spacer fragment would be subcloned into the Xho I and Kpn I sites of the above pBSSK+ vector containing the engineered upstream region plus positioning element(s) and cleavage site(s). The final, assembled 3' regulatory set would then be subcloned as a BssH II to Kpn I fragment into the BssH II to Asp 718 I sites of a plant expression vector for in planta testing as described above in Example 2.

Vectors used to clone and express the 3' termination sequences of the present invention are derivatives of commercially available plasmids such as pCR2.1-Topo (Invitrogen, San Diego, Calif.), pBSSK+ (Stratagene, La Jolla, Calif.) and pBI121 (Clonetech, Palo Alto, Calif.).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

```
PECS1CA  5'- AGCTTAATAAATAAATATTTCTCTATCTTTAAAGGCAC -3'    SEQ ID NO:64

PECS2NA  5'- TCGAGTGCCTTTAAAGATAGAGAAATATTTATTTATTAA -3'   SEQ ID NO:65
```

What is claimed is:

1. A recombinant expression cassette comprising a promoter that is functional in plants operably linked with a coding sequence having a stop codon, the coding sequence being operably linked with a non-plant 3' termination sequence, wherein the non-plant termination sequence is heterologous to the coding sequence and comprises:
   i. a cleavage site including a nucleotide sequence YA defining a position of endonucleolytic cleavage and subsequent 3' polyadenylation;
   ii. a positioning element of 6 nucleotides located between 10 nucleotides and 40 nucleotides 5' of the cleavage site and with at least 4 out of 6 nucleotides being adenine;
   iii. an upstream element that
      (a) is located between 1 nucleotide and 250 nucleotides 5' of the positioning element; and
      (b) comprises TAYRTA or two or more repeats of the TA, TG, or TA and TG where the repeats are separated by 0 to 10 nucleotides;
   wherein the non-plant 3' termination sequence is a fungal 3' termination sequence.

2. The recombinant expression cassette of claim 1, wherein the cleavage site is flanked by a pair of thymidine-rich regions, each thymidine-rich region:
   a. comprising at least 6 nucleotide pairs of at least 80% thymidine; and
   b. being within about 50 nucleotides of the cleavage site.

3. The recombinant expression cassette of claim 1, wherein the promoter is a virus promoter.

4. The recombinant expression cassette of claim 1, wherein the 3' termination sequence has at least 90% sequence identity to SEQ ID NO:1.

5. A recombinant plant cell comprising the expression cassette of claim 1.

6. The recombinant expression cassette of claim 1, wherein the non-plant 3' termination sequence is a native fungal 3' termination sequence.

* * * * *

SEQUENCE LISTING

<160> NUMBER OF SEQ ID NOS: 81

<210> SEQ ID NO 1
<211> LENGTH: 485
<212> TYPE: DNA
<213> ORGANISM: Saccharomyces cerevisiae

<400> SEQUENCE: 1

| | | | | | |
|---|---|---|---|---|---|
| gcgcgcggaa | ggaggaaagt | gactccttcg | ttgcgtagac | agtatgaaaa | tatttttact | 60 |
| gtgatactta | caagttgata | tatggttgtg | tgtaacttat | ttatttgaga | ggtattttaa | 120 |
| cacaccttag | aactaaaact | taataaataa | atatttctct | atctttaaag | gcacatatta | 180 |
| cgtggctaag | gcaattacag | ctgatatact | gtaaaactca | tgtcgccact | aaattcttct | 240 |
| aacacgcgtt | ctgtctcttt | ccaagggact | ccgaatatgc | cactatttat | ctgtggcatt | 300 |
| tccaatttat | attccctat | tgggtatttg | atgtggccgt | ttaaatagtc | accgattgaa | 360 |
| tcttcacttg | ttcgagtttt | gtcttttgct | tctctaaagg | tcttcaattt | atctaaagca | 420 |
| agttttgtat | aattcaaaat | actttgcttt | tctccatgac | ttgaacctcc | aaatgatgag | 480 |
| gtacc | | | | | | 485 |

<210> SEQ ID NO 2
<211> LENGTH: 541
<212> TYPE: DNA
<213> ORGANISM: Saccharomyces cerevisiae

<400> SEQUENCE: 2

| | | | | | |
|---|---|---|---|---|---|
| gcgcgcaagt | cacaagtagt | agcgagttac | aacaaatctt | ccctgttagt | caacaataag | 60 |
| atgattatgt | gttgtgtact | acgaaaataa | gcaaaaaata | aataaaataa | aaacaaaaac | 120 |
| agaaacaaaa | acaaaaacaa | aaacaaaaac | acatattgtt | atgatgactg | gacgaaagaa | 180 |
| agatcgtcgt | tactttccta | attgtttgtc | ttcagtacag | ttattatcag | tgttctcttt | 240 |
| cttttttatt | gtactatgtg | atgttactga | tacatcacgc | gcttcctta | tgttttcttt | 300 |
| ttttatgttc | gttacaggat | ttatagtttt | tacagtatat | tgacttcaat | aatttctaat | 360 |
| attcagttcc | tattaaattt | gattattccg | attagatcgg | tcggcgctac | caaaaagagg | 420 |
| cgaagaaaag | aggaaaacgc | aagtggataa | aggggtgggg | ggcaaaagta | tttaagaaaa | 480 |
| agcgatgcga | tggagagaac | aaatggataa | gttgcgtttc | ctcgtaatat | tacaaggtac | 540 |
| c | | | | | | 541 |

<210> SEQ ID NO 3
<211> LENGTH: 666
<212> TYPE: DNA
<213> ORGANISM: Saccharomyces cerevisiae

<400> SEQUENCE: 3

| | | | | | |
|---|---|---|---|---|---|
| gcgcgccatc | caagagattg | tctttgtctg | caaggaaaat | caacatgaga | aaagtatgaa | 60 |
| aaatagacgg | cttctactat | catcattaca | gtaaggttg | aagtcaggaa | aggttaaaaa | 120 |
| taaaataaat | atcaaaaagt | ttttagcgga | aggcgttaag | gcagcaagta | cacattcatt | 180 |
| tatctatcta | tacatctata | aacacaacta | caattttttt | agaaatgaa | tttattatat | 240 |
| gaagggaaga | catatagagg | caacagtaca | taaaggtaag | aataaaagcg | attttagcta | 300 |
| gtatatttct | gggtatttct | tacatagtct | ttgtaaagca | accacaccgt | ttaagcttaa | 360 |
| atcttcgttc | tccttgaatt | tgcatagtac | agcgtctaga | atcaaaaatc | ctagctcgcc | 420 |

```
gtcatcattg ttcctgcaaa caaactcata ccacgagtcg atctcaaatg ttttattcat    480
agatacacga atattgttca acgtaatcat ttcaacctcg ctgccgtttt tcgatgatat    540
ggttggcgat tgtaaaatca actgagattc agtgggttgt gatttgattt gcgctattat    600
cctaaacaca ggagcattga cgttggagat ttctgtgggg tcaactcttg gtgtttcgct    660
ggtacc                                                              666

<210> SEQ ID NO 4
<211> LENGTH: 34
<212> TYPE: DNA
<213> ORGANISM: Artificial Sequence
<220> FEATURE:
<223> OTHER INFORMATION: PCR primer

<400> SEQUENCE: 4
gcgcgcggaa ggaggaaagt gactccttcg ttgc                                34

<210> SEQ ID NO 5
<211> LENGTH: 34
<212> TYPE: DNA
<213> ORGANISM: Artificial Sequence
<220> FEATURE:
<223> OTHER INFORMATION: PCR primer

<400> SEQUENCE: 5
ggtacctcat catttggagg ttcaagtcat ggag                                34

<210> SEQ ID NO 6
<211> LENGTH: 33
<212> TYPE: DNA
<213> ORGANISM: Artificial Sequence
<220> FEATURE:
<223> OTHER INFORMATION: PCR primer

<400> SEQUENCE: 6
gcgcgcaagt cacaagtagt agcgagttac aac                                 33

<210> SEQ ID NO 7
<211> LENGTH: 37
<212> TYPE: DNA
<213> ORGANISM: Artificial Sequence
<220> FEATURE:
<223> OTHER INFORMATION: PCR primer

<400> SEQUENCE: 7
ggtaccttgt aatataacga ggaaacgcaa cttatcc                             37

<210> SEQ ID NO 8
<211> LENGTH: 34
<212> TYPE: DNA
<213> ORGANISM: Artificial Sequence
<220> FEATURE:
<223> OTHER INFORMATION: PCR primer

<400> SEQUENCE: 8
gcgcgccatc caagagattg tctttgtctg caag                                34

<210> SEQ ID NO 9
<211> LENGTH: 33
<212> TYPE: DNA
<213> ORGANISM: Artificial Sequence
<220> FEATURE:
<223> OTHER INFORMATION: PCR primer
```

-continued

```
<400> SEQUENCE: 9
ggtaccagcg aaacaccaga gttgacccca cag                                    33

<210> SEQ ID NO 10
<211> LENGTH: 34
<212> TYPE: DNA
<213> ORGANISM: Artificial Sequence
<220> FEATURE:
<223> OTHER INFORMATION: PCR primer

<400> SEQUENCE: 10
ggcgcgccta ggccaagccc tgcgtccagc gagc                                   34

<210> SEQ ID NO 11
<211> LENGTH: 35
<212> TYPE: DNA
<213> ORGANISM: Artificial Sequence
<220> FEATURE:
<223> OTHER INFORMATION: PCR primer

<400> SEQUENCE: 11
cggggtaccc cgagtcagct tgtgcaacag cgtcg                                  35

<210> SEQ ID NO 12
<211> LENGTH: 43
<212> TYPE: DNA
<213> ORGANISM: Artificial Sequence
<220> FEATURE:
<223> OTHER INFORMATION: Mutagenic Oligonucleotide

<400> SEQUENCE: 12
taatatacat tttatgactg aattcttttt tgtacaacac tcc                         43

<210> SEQ ID NO 13
<211> LENGTH: 44
<212> TYPE: DNA
<213> ORGANISM: Artificial Sequence
<220> FEATURE:
<223> OTHER INFORMATION: PCR primer

<400> SEQUENCE: 13
ggagtgttgt acaaaaaaga attcagtcat aaaatgtata ttac                        44

<210> SEQ ID NO 14
<211> LENGTH: 44
<212> TYPE: DNA
<213> ORGANISM: Artificial Sequence
<220> FEATURE:
<223> OTHER INFORMATION: Mutagenic oligonucleotide

<400> SEQUENCE: 14
ggagtgttgt acaaaaaaga attcagtcat aaaatgtata ttac                        44

<210> SEQ ID NO 15
<211> LENGTH: 27
<212> TYPE: DNA
<213> ORGANISM: Artificial Sequence
<220> FEATURE:
<223> OTHER INFORMATION: Mutagenic Oligonucleotide

<400> SEQUENCE: 15
aattcacaca cacacaaaca cacacag                                           27

<210> SEQ ID NO 16
<211> LENGTH: 510
```

```
<212> TYPE: DNA
<213> ORGANISM: Saccharomyces cerevisiae

<400> SEQUENCE: 16
tgaagaagag tgactgaatt ttgaatttga ttatcttcaa cgactgagaa gaatgagcac      60
cattttgata ttttgattaa ttaagtggta atcttaagct catatacaaa aagggaagga     120
aaaaaaataa agatagaaaa gatcttagga acggatagaa gtttgaaaaa ggaataacag     180 gtaattttc  attttcatat cggttgtaac attataaagc tcacaaattt aaaacaaaaa     240
aaaacataaa cctaacaagg ttaatcattt gcacatgatc tcatcatata gatcaattca     300
taatctatat aataatgaat aattagaata aaaatttcct cttgtctcag aacgcccatc     360
ggatggcata actttagtta atgatatcac gacggacgaa gtattgaaag acaacctaac     420
ctgttcatca atttaaaagt caacgcagaa actataatac attgccacat agttctttcc     480
gatatgaaca acctaactca caaaatttac                                      510

<210> SEQ ID NO 17
<211> LENGTH: 877
<212> TYPE: DNA
<213> ORGANISM: Saccharomyces cerevisiae

<400> SEQUENCE: 17
attaatggat gccttcaatg agttccacga cgcacgttta ttttttcgac tgagaatccc      60
tcagcaaata taatctattt tttatatatc tgtgtatatg taagcatgta taactagtta     120
caaatatgat aactgctttg gcgatcactt cattttcttg agaggggtac tcagtagccg     180
ccaagcacga aatgtccgtt attaaaaatt ggggagtgaa tcttaaaagc ccgaaaagga     240
aattcaaaat ctgtctattt ataggccgtc gcgctctacg aaaacgcgaa attattcaaa     300
cggaaaacgg aaaaaaatct aaaaaaagaa attaattgag agatctcacg gaaatgccgc     360
gaggaatgtt tctcgaggct gagcggcgtg gtctgtgcaa aaaaatggca attttttttgt    420 aggagtttgc attgggccat tcagaaggag caccgttaga tgggatggta aatgaatttg     480
ctgtttcaga tttgaatcaa tctttacccg ttattttttgc cgttttgctt tcataatctg    540
caaattaaca aagtcataaa gaacataaag acatcacccc agttttttaca ctctttttttc   600 ctgtgtttgg tttagcacaa cttttccaata accaagttgg tttcagatca tcccccatatt   660 attttctagt ttcatttact taccaaactc accattcaag gctttcaaat taagttacga     720
gtacagtgga ccattttttt ctgattcttc atattttccg ttataagtct tataaggaag     780
gtatacattt atattgcgaa tttgaaaaat aatttaaagc tgactttgcg ttttaggtag     840
gctagaaaag aatacaacta tccctaaaca cattcta                              877

<210> SEQ ID NO 18
<211> LENGTH: 669
<212> TYPE: DNA
<213> ORGANISM: Saccharomyces cerevisiae

<400> SEQUENCE: 18
tagctttatt ggatgacttt atggaaaatt catgttttga gtataaatta tacgtacgaa      60
tcttatagat atatattttt cttttaaaac tccatttcag ctcataagcc gatacaaaca     120
ccttctatat attatttctc taacagctat gttaacatga ttgcctttgt ttatctacta     180
aaggaccctt ctactttatc taccatacgc tatatttttc tctgtgtttc aatcatatcg     240
agaaaaattt ggtacttcgt gtctaaaaga attctatctg gatgagtttt ctcatttgga     300
```

```
ttgacaattc ttgcattacc cgttagctct tgcataactt tccatagaaa acttgtcccg      360
ttatatcttc cctctcctag gctctcctgt cccacggtca atgaagcatc cttactactt      420
tcctcagagg ttttgtcaag tggttgttgt gtgcaaatcg gaagagaata gttatttatt      480
ttggcaggcg cacttggagt tgaaagttgt agattatgtg gggatacaaa gccatttgtc      540
gagtttcgat cttccattga taacttttgt atcgacgaat atgaatcgtt aaaacgttcc      600
gtctttgtct gagaagattt ttggcctttg agagttcttt tttccctggt ataatcaaaa      660
tcttcactt                                                             669
```

<210> SEQ ID NO 19
<211> LENGTH: 443
<212> TYPE: DNA
<213> ORGANISM: Saccharomyces cerevisiae

<400> SEQUENCE: 19

```
aattgcgtcc aaagaagaag ttgaaataat cgatttatta cgatctccac aaatccaaag       60
tttgtataca tcacgatttt tttactacat atatatttcc ttttctattc tatttgtaaa      120
tgggaggaaa tcttaatatg gacctctctt cacaaattgt tctataatac aatatatatc      180
aagatataat aacaagtcat tgagataat ggtatgcaaa tacgcgaaat aagagtaaac       240
ggatacagtg agcctgaaga ggacaagctg cttccatgtt gtagtgttta gatatatgag      300
cttaaaattt agatttactg aatattatac aatagtaatt atacataaag aaattccatt      360
ttatctgttc gatagcaatg gaagaggaga gagttctgtg aaacaaataa cagcagcaca      420
gaaaactccc gtcaacgtaa tat                                              443
```

<210> SEQ ID NO 20
<211> LENGTH: 427
<212> TYPE: DNA
<213> ORGANISM: Saccharomyces cerevisiae

<400> SEQUENCE: 20

```
agtccactct tcaccttgtc ttgaggttga ggggtggtaa ctgatcagtc ctcgcaatat       60
tttcattatg tcaatatata tatgtttact ctccttttt cttttggtt tttttttttt       120 tttgataaat actccataga acactaaata aattgttcaa ctgtgttatt gtctttattc     180
atgttggttt tcaagagctt ggattttgaa tcgtcttata ctatgacgtt cactattttc     240
gcgaacccgg gtaataccat tagctatttt gatagaaagg gattttttatt agggaatata    300 accacattta aagtgtccta tcatgtttca atctccagta aacgcacata agccgaccaa     360
ttgagtcaac ctttaactc tatttaattt gatacggata gaatattgtg actaccaaaa      420
gggaaaa                                                              427
```

<210> SEQ ID NO 21
<211> LENGTH: 810
<212> TYPE: DNA
<213> ORGANISM: Saccharomyces cerevisiae

<400> SEQUENCE: 21

```
taagtgtcat tccgtctaca aggttaacgc ttaagtaaag tatttttaaa acttatatat       60
tttaattgat cgttaaattt tgaaaaaggc ttttaatatt gtcattattt acttttctat     120
ttacaacaaa agaacaaatg aatagataga cagtagagga atataagtag tatgcagtgc    180
catgcgggat caaggaattt gtatctctaa ttttcgtggt tgtatgcgtc tctaaacaag    240
tcaatatttt gctgtaagat ggttctgccg ctcctttcag ttcctttaag aagcgtacct    300
```

```
gcagatattt taacatcctc catggtttca ttgactttac tgacaagttg attgctcaag    360
tcatcaacat gttttcccca attttcacta aatacttgca aaacagcatc gaatcccatt    420 ttacccttt tagcgttctc gcaaaacctt tgaactgacc aatcttccat cttattacac    480
agctttctaa tggatccata tgctgtaatt tgggcttcct gctggaaaag tgttttatta    540
gccgagtcat cgggatgcgg gctatatgtt acagtttcgt agacttttaa tagattgcac    600
atcgttaaat tacagcttct catggtcaag ctcttttat ttaagtctac cacagaaact    660
tctctgacat gactcatatt ggtccctcct agcatcatca tgatccattt gggaacacct    720
tgttttacag taatcaaccg ttcagtaact aagaccttac cttgatcctt caattctctt    780
cttaaaacgt ccactgcgat gacatgtgta                                    810
```

<210> SEQ ID NO 22
<211> LENGTH: 763
<212> TYPE: DNA
<213> ORGANISM: Saccharomyces cerevisiae

<400> SEQUENCE: 22

```
tgatatagta tatcatcctt acgtatttga cgttattaca ttatatatag tttctcaaat     60
aatatttcta gtttattttt gtatcataat aaaaacgtat accaaatata ccattatttt    120
tcataacatt atggtaggga tagggaatca agtaactaat ttatatccgc agagcattgg    180
gaaaaccaac ggcgctagta aatgcattta aattacgtcc gtccaacttc taagcttcaa    240
tggtagactc ttaactctga cctttttagc aattaagctc ttgaagatat caaaagtgtt    300
accgtccggc tgtaaattat aaacgttttcc tgtaaattga gtggaatacc gcttaccatt    360
cttttgcaat cagtaaaccg tagtcttccg tgataccagt aatcatggct tgcgtatttc    420
cgtgatctgg taatgttact atttggttac tatgtaacac aactcataat aacttggcaa    480
tatttccgca gctccgtagt taataaactg ttttaatatg acctcaaggt tattcatata    540
gagtgcctgc agttttttctg cctttattgc tggcaataaa tcaaggtgta attgttggcg    600
ttcttcattc aggatatcaa tccaagtttg taatgaagtt gtaggaccat cactagtcaa    660
atttatacca cagccaagta gcaaacaata tttattgttt atgaagtggg tattaactaa    720
taaaccagag atcttaagat aagcgggctc gatatcacct aag                      763
```

<210> SEQ ID NO 23
<211> LENGTH: 498
<212> TYPE: DNA
<213> ORGANISM: Saccharomyces cerevisiae

<400> SEQUENCE: 23

```
tgatgcttac gtttcttctg acgaagaatt ctaatctttt tgatcactgc tttcacagtt     60
ttctttaaga ttttattga tcaataattt atgtatattt aatttctat gttttttgtaa    120 tattgtttat tttggtaaaa tatagacgca acttccttat tataaagaaa ggcattattt    180
aaaagaaaaa gcgttccatt agtcagacat cttttttttt catacattct taagctcagg    240
caaattgagc attgcctcat acccttttcg gtaagagggt aacgaaaata tttttttgga    300
agaataaaaa taggtgacgg atcatagact aggaagcttt aaaacatgat tgagcgtaat    360
attatattcc ttctagaaaa gataaaagag ccaagaccta aaattttttc atccctgttc    420
tattaaaatt gtggaaatga ggttttttgag gggatttgta ttttctttgg ctttcactct    480
atataaagta actgccac                                                 498
```

<210> SEQ ID NO 24
<211> LENGTH: 492
<212> TYPE: DNA
<213> ORGANISM: Pichia pastoris

<400> SEQUENCE: 24

| | | | | | | |
|---|---|---|---|---|---|---|
| agtttgtagc | cttagacatg | actgttcctc | agttcaagtt | gggcacttac | gagaagaccg | 60 |
| gtcttgctag | attctaatca | agaggatgtc | agaatgccat | ttgcctgaga | gatgcaggct | 120 |
| tcatttttga | tactttttta | tttgtaacct | atatagtata | ggatttttt | tgtcattttg | 180 |
| tttcttctcg | tacgagcttg | ctcctgatca | gcctatctcg | cagctgatga | atatcttgtg | 240 |
| gtaggggttt | gggaaaatca | ttcgagtttg | atgtttttct | tggtatttcc | cactcctctt | 300 |
| cagagtacag | aagattaagt | gagaccttcg | tttgtgcgga | tccccacac | accatagctt | 360 |
| caaaatgttt | ctactccttt | tttactcttc | cagattttct | cggactccgc | gcatcgccgt | 420 |
| accacttcaa | acacccaag | cacagcatac | taaattttcc | ctctttcttc | ctctagggtg | 480 |
| tcgttaatta | cc | | | | | 492 |

<210> SEQ ID NO 25
<211> LENGTH: 876
<212> TYPE: DNA
<213> ORGANISM: Pichia pastoris

<400> SEQUENCE: 25

| | | | | | | |
|---|---|---|---|---|---|---|
| tctaaagagt | agcaattctg | atgagggct | gagatatctc | agcactttgt | catactcact | 60 |
| tcaaacccct | gtattatcaa | aaagtttctc | gatgccgggg | cggctaaggc | tcaagtctag | 120 |
| tcagccgtgg | tatcttctga | actgcatcac | gagttttatg | cgagcattag | tacggcgttc | 180 |
| tagcgattcg | ggtttgtttg | gttttttttt | ctaaggcaat | tttcaacacg | attcacaaat | 240 |
| tagacagtcg | cacaccgcag | gttgaaaagg | gggcggtact | gcgcgctggt | cggcttgttg | 300 |
| cctccttcta | attcccgtt | tgtcttccag | tctattgaca | ccgagggctt | ctcgaactgc | 360 |
| tctatgcagt | ctcttgggtt | actcgtcttt | tttttcccgt | gggcactggg | ctccctgttt | 420 |
| tagatcgtcc | tacttaattg | atgcctgatg | acgggttgt | aagcctgatc | cagtagcatt | 480 |
| acttaacata | taaaataaaa | agtggatgag | atctttcttt | cgccgtttag | gtcttaaaag | 540 |
| ccagtttgcg | tcttaaagcc | agtttgcgaa | tataaatgtt | cgtataagga | tgaatcgtat | 600 |
| tcaaagaatt | aaattgtcag | aaaaactact | gatgctcgca | taagacatgt | gatgcagtcg | 660 |
| aagatacgca | tgcatataca | tatatacact | agctaacatc | cacccaatat | atatatccct | 720 |
| ctccgtttat | ctatttcaca | cacataccaa | aagctggttt | tatccgtcag | acctacaacg | 780 |
| cactctcccg | cttcgctttc | tgccccttcg | ccaactcatc | caaaagcagc | agccgcttat | 840 |
| cccctgaacg | acttccatcc | tctgttccgt | caaagt | | | 876 |

<210> SEQ ID NO 26
<211> LENGTH: 577
<212> TYPE: DNA
<213> ORGANISM: Pichia pastoris

<400> SEQUENCE: 26

| | | | | | | |
|---|---|---|---|---|---|---|
| actgttgcgt | agacatgagc | ggggctactt | acagctggcc | gcagtatcta | catgacacat | 60 |
| catcggtgtt | gttgttgttg | ttgttgttgt | tgcatggtca | tctgggatcg | cccttcgtc | 120 |
| gcctgtgtct | cgtgtccaga | ccccgcgcgt | ccttggctgt | agtctctgta | cgtatggttt | 180 |
| tgcatttacg | gccagctggt | atctggcttt | ttggagttac | ttttttgggat | ttggaaagaa | 240 |

```
ctacacagct tgttgcctgg agcgatgcct tggacaacaa acaggaaaat cgacggaaag      300
gatgcaataa tggacgggaa gtttagagtc cttgcattgg aggcgggcat aggcagccct      360
ggaatacaga accctgtaga gttaaggagt gtaaacaccc gacacagtat ataccaggcc      420
cctttgtctc agggcacgag ccaggggcct atagagcgat aaaaccatgc gactattgat      480
aataatgata accagcagcg catagcccag tacgaggcct tgacgtcaag gtcagtttct      540
gcagaacaat cgcattatcg aatccatgga atgcact                               577

<210> SEQ ID NO 27
<211> LENGTH: 650
<212> TYPE: DNA
<213> ORGANISM: Pichia pastoris

<400> SEQUENCE: 27
atcgtccacc gcaagtgctt ctaaggtatg agtcgcaaaa ttgttttttta ttttggtct      60 tgagtctaat atgctcgcag ctcttgagtt gtatatggtc gttggtcgcg tattttctgt     120
tgtattaaaa gatcaaacga gatcaaggga tggctcgcgg gctgtctctc gcactaggag     180
gaagaatgcc tgaaaaagga actttgattt tagctgtgga atagagatgg cttgtttgag     240
gacgcttgtc gcttggcgca gggacttgaa tggcagcttg tggaaaccga aggcgagaaa     300
agtcgacgga tactgtacgt ggttctattg ccagtgcggt ggaagcttgg ttgtgatata     360
gttcaatcct tctttgaatc tgtttgtttc atatttggat tctctgcttg cgcattctca     420
tcttcgagaa gcgactgcag ggattgttgg ttctgtggag ctgatgagcg cgccttgacc     480
acccttgttc ttgttttgct cttttgttct catttaaccc gtttctccct tccaaccctt     540
tgaccttgca acattgtctc ccagcgcgtt gccaaagcga acttgatatc agtatagtat     600
gaccaagtag tctaccaaaa taaatttttag tacagtattg ctagtataca                650

<210> SEQ ID NO 28
<211> LENGTH: 412
<212> TYPE: DNA
<213> ORGANISM: Homo sapiens

<400> SEQUENCE: 28
ccaagccctg cgtccagcga gcgtcacagc acaacctgca aaaacggagc tgggctgcag       60
ctggggctgg catggacttt catttcagag attcggtttt taagaagatg catgcctagc      120
gtgttctttt tttttttccaa tgatttgtaa tatacatttt atgactggaa acttttttgt     180
acaacactcc aataaacatt ttgattttag gttctgcctc tgagtttatt cctgagggga     240
agctcgagcc gggcctctgc cctaatgaag cggatgtcta agaaagatcc ctccaccccc     300
aaggaaaaag gtcactggct agtgtagcta gtgtaaacag gacccaggcg atgcatggga     360
ccctgccctt ttttttctag tgagcctccg acgctgttgc acaagctgac tc              412

<210> SEQ ID NO 29
<211> LENGTH: 308
<212> TYPE: DNA
<213> ORGANISM: Homo sapiens

<400> SEQUENCE: 29
gaagcctgca cgcggcagtt ctttgttaaa gatctgaggg actcgtcagt cctagcgtcg       60
ccgcctgcag cctcttccaa gccctgcgtc agcgagcgt cacagcacaa cctgcaaaaa      120
cggagctggg ctgcagctgg ggctggcatg gactttcatt tcagagattc ggtttttaag      180
aagatgcatg cctagcgtgt tctttttttt ttccaatgat ttgtaatata catttatga      240
```

```
ctggaaactt ttttgtacaa cactccaata aacattttga ttttaggttc tgcctctgag    300
tttattcc                                                              308
```

<210> SEQ ID NO 30
<211> LENGTH: 363
<212> TYPE: DNA
<213> ORGANISM: Homo sapiens

<400> SEQUENCE: 30

```
ctagccatgg ccactgagcc ctctgctgcc ctgccagaat ctgccgcccc tccatcttct     60
acctctgaat ggccacccctt agaccctgtg atccatcctc tctcctagct gagtaaatcc   120
gggtctctag gatgccagag gcagcgcaca caagctggga aatcctcagg gctcctacca   180
gcaggactgc ctcgctgccc cacctcccgc tccttggcct gtccccagat tccttccctg   240
gttgacttga ctcatgcttg tttcactttc acatggaatt tcccagttat gaaattaata   300
aaaatcaatg gtttccacat ctctcagtgc ctctatctgg aggccaggta gggctggcct   360
tgg                                                                  363
```

<210> SEQ ID NO 31
<211> LENGTH: 341
<212> TYPE: DNA
<213> ORGANISM: Homo sapiens

<400> SEQUENCE: 31

```
tggctgttaa ttcttcagtc atggcattcg cagtgcccag tgatggcatt actctgcact    60
atagccattt gccccaactt aagtttagaa attacaagtt tcagtaatag ctgaacctgt   120
tcaaaatgtt aataaaggtt tcgttgcatg gtagcatact tggtgttttg tcatgaaatt   180
ctctagtgat gtgtgggtac gcttaaaact ggtgaaaatg tttagggatt taattttgag   240
attggtaatg tgctcaaagt taagtcactt gactttggta tacacttggg tgggctgagg   300
ggcaagagcc ttctttgctg tttaagtcat tacaagttag g                        341
```

<210> SEQ ID NO 32
<211> LENGTH: 29
<212> TYPE: DNA
<213> ORGANISM: Artificial Sequence
<220> FEATURE:
<223> OTHER INFORMATION: PCR Primer

<400> SEQUENCE: 32

```
cctaggtgaa gaagagtgac tgaattttg                                       29
```

<210> SEQ ID NO 33
<211> LENGTH: 28
<212> TYPE: DNA
<213> ORGANISM: Artificial Sequence
<220> FEATURE:
<223> OTHER INFORMATION: PCR Primer

<400> SEQUENCE: 33

```
ggtaccgtaa attttgtgag ttaggttg                                        28
```

<210> SEQ ID NO 34
<211> LENGTH: 28
<212> TYPE: DNA
<213> ORGANISM: Artificial Sequence
<220> FEATURE:
<223> OTHER INFORMATION: PCR Primer

<400> SEQUENCE: 34
cctaggatta atggatgcct tcaatgag                                    28

<210> SEQ ID NO 35
<211> LENGTH: 29
<212> TYPE: DNA
<213> ORGANISM: Artificial Sequence
<220> FEATURE:
<223> OTHER INFORMATION: PCR Primer

<400> SEQUENCE: 35
ggtacctaga atgtgtttag ggatagttg                                   29

<210> SEQ ID NO 36
<211> LENGTH: 30
<212> TYPE: DNA
<213> ORGANISM: Artificial Sequence
<220> FEATURE:
<223> OTHER INFORMATION: PCR Primer

<400> SEQUENCE: 36
actagttagc tttattggat gactttatgg                                  30

<210> SEQ ID NO 37
<211> LENGTH: 30
<212> TYPE: DNA
<213> ORGANISM: Artificial Sequence
<220> FEATURE:
<223> OTHER INFORMATION: PCR Primer

<400> SEQUENCE: 37
ggtaccaagt gaagattttg attataccag                                  30

<210> SEQ ID NO 38
<211> LENGTH: 29
<212> TYPE: DNA
<213> ORGANISM: Artificial Sequence
<220> FEATURE:
<223> OTHER INFORMATION: PCR Primer

<400> SEQUENCE: 38
cctaggaatt gcgtccaaag aagaagttg                                   29

<210> SEQ ID NO 39
<211> LENGTH: 29
<212> TYPE: DNA
<213> ORGANISM: Artificial Sequence
<220> FEATURE:
<223> OTHER INFORMATION: PCR Primer

<400> SEQUENCE: 39
ggtaccatat tacgttgacg ggagttttc                                   29

<210> SEQ ID NO 40
<211> LENGTH: 29
<212> TYPE: DNA
<213> ORGANISM: Artificial Sequence
<220> FEATURE:
<223> OTHER INFORMATION: PCR Primer

<400> SEQUENCE: 40
cctaggagtc cactcttcac ctcgtcttg                                   29

<210> SEQ ID NO 41
<211> LENGTH: 26

```
<212> TYPE: DNA
<213> ORGANISM: Artificial Sequence
<220> FEATURE:
<223> OTHER INFORMATION: PCR Primer

<400> SEQUENCE: 41 ggtaccttt cccttttggt agtcac                                            26

<210> SEQ ID NO 42
<211> LENGTH: 28
<212> TYPE: DNA
<213> ORGANISM: Artificial Sequence
<220> FEATURE:
<223> OTHER INFORMATION: PCR Primer

<400> SEQUENCE: 42
cctaggtaag tgtcattccg tctacaag                                         28

<210> SEQ ID NO 43
<211> LENGTH: 28
<212> TYPE: DNA
<213> ORGANISM: Artificial Sequence
<220> FEATURE:
<223> OTHER INFORMATION: PCR Primer

<400> SEQUENCE: 43
ggtacctaca catgtcatcg cagtggac                                         28

<210> SEQ ID NO 44
<211> LENGTH: 29
<212> TYPE: DNA
<213> ORGANISM: Artificial Sequence
<220> FEATURE:
<223> OTHER INFORMATION: PCR Primer

<400> SEQUENCE: 44
cctaggtgat atagtatatc atccttacg                                        29

<210> SEQ ID NO 45
<211> LENGTH: 23
<212> TYPE: DNA
<213> ORGANISM: Artificial Sequence
<220> FEATURE:
<223> OTHER INFORMATION: PCR Primer

<400> SEQUENCE: 45
ggtaccctta ggtgatatcg agc                                              23

<210> SEQ ID NO 46
<211> LENGTH: 29
<212> TYPE: DNA
<213> ORGANISM: Artificial Sequence
<220> FEATURE:
<223> OTHER INFORMATION: PCR Primer

<400> SEQUENCE: 46
cctaggtgat gcttacgttt cttctgacg                                        29

<210> SEQ ID NO 47
<211> LENGTH: 30
<212> TYPE: DNA
<213> ORGANISM: Artificial Sequence
<220> FEATURE:
<223> OTHER INFORMATION: PCR Primer

<400> SEQUENCE: 47
```

```
ggtaccgtgg cagttacttt atatagagtg                                30
```

<210> SEQ ID NO 48
<211> LENGTH: 28
<212> TYPE: DNA
<213> ORGANISM: Artificial Sequence
<220> FEATURE:
<223> OTHER INFORMATION: PCR Primer

<400> SEQUENCE: 48

```
cctaggagtt tgtagcctta gacatgac                                  28
```

<210> SEQ ID NO 49
<211> LENGTH: 29
<212> TYPE: DNA
<213> ORGANISM: Artificial Sequence
<220> FEATURE:
<223> OTHER INFORMATION: PCR Primer

<400> SEQUENCE: 49

```
ggtaccggta attaacgaca ccctagagg                                 29
```

<210> SEQ ID NO 50
<211> LENGTH: 29
<212> TYPE: DNA
<213> ORGANISM: Artificial Sequence
<220> FEATURE:
<223> OTHER INFORMATION: PCR Primer

<400> SEQUENCE: 50

```
cctaggtcta aagagtagca attctgatg                                 29
```

<210> SEQ ID NO 51
<211> LENGTH: 31
<212> TYPE: DNA
<213> ORGANISM: Artificial Sequence
<220> FEATURE:
<223> OTHER INFORMATION: PCR Primer

<400> SEQUENCE: 51

```
ggtaccactt tgacggaaca gaggatggaa g                              31
```

<210> SEQ ID NO 52
<211> LENGTH: 26
<212> TYPE: DNA
<213> ORGANISM: Artificial Sequence
<220> FEATURE:
<223> OTHER INFORMATION: PCR Primer

<400> SEQUENCE: 52

```
cctaggactg ttgcgtagac atgagc                                    26
```

<210> SEQ ID NO 53
<211> LENGTH: 25
<212> TYPE: DNA
<213> ORGANISM: Artificial Sequence
<220> FEATURE:
<223> OTHER INFORMATION: PCR Primer

<400> SEQUENCE: 53

```
ggtaccagtg cattccatgg attcg                                     25
```

<210> SEQ ID NO 54
<211> LENGTH: 27
<212> TYPE: DNA
<213> ORGANISM: Artificial Sequence

```
<220> FEATURE:
<223> OTHER INFORMATION: PCR Primer

<400> SEQUENCE: 54
cctaggatcg tccaccgcaa gtgcttc                                          27

<210> SEQ ID NO 55
<211> LENGTH: 27
<212> TYPE: DNA
<213> ORGANISM: Artificial Sequence
<220> FEATURE:
<223> OTHER INFORMATION: PCR Primer

<400> SEQUENCE: 55
ggtacctgta tactagcaat actgtac                                          27

<210> SEQ ID NO 56
<211> LENGTH: 33
<212> TYPE: DNA
<213> ORGANISM: Artificial Sequence
<220> FEATURE:
<223> OTHER INFORMATION: PCR Primer

<400> SEQUENCE: 56
ggcgcgccta gggaagcctg cacgcggcag ttc                                   33

<210> SEQ ID NO 57
<211> LENGTH: 33
<212> TYPE: DNA
<213> ORGANISM: Artificial Sequence
<220> FEATURE:
<223> OTHER INFORMATION: PCR Primer

<400> SEQUENCE: 57
cggggtaccc cggaataaac tcagaggcag aac                                   33

<210> SEQ ID NO 58
<211> LENGTH: 34
<212> TYPE: DNA
<213> ORGANISM: Artificial Sequence
<220> FEATURE:
<223> OTHER INFORMATION: PCR Primer

<400> SEQUENCE: 58
ggcgcgccta ggctagccat ggccactgag ccct                                  34

<210> SEQ ID NO 59
<211> LENGTH: 33
<212> TYPE: DNA
<213> ORGANISM: Artificial Sequence
<220> FEATURE:
<223> OTHER INFORMATION: PCR Primer

<400> SEQUENCE: 59
cggggtaccc cgccaaggcc agccctacct ggc                                   33

<210> SEQ ID NO 60
<211> LENGTH: 37
<212> TYPE: DNA
<213> ORGANISM: Artificial Sequence
<220> FEATURE:
<223> OTHER INFORMATION: PCR Primer

<400> SEQUENCE: 60
ggcgcgccta ggtggctgtt aattcttcag tcatggc                               37
```

<210> SEQ ID NO 61
<211> LENGTH: 37
<212> TYPE: DNA
<213> ORGANISM: Artificial Sequence
<220> FEATURE:
<223> OTHER INFORMATION: PCR Primer

<400> SEQUENCE: 61
cggggtaccc cgcctaactt gtaatgactt aaacagc                              37

<210> SEQ ID NO 62
<211> LENGTH: 33
<212> TYPE: DNA
<213> ORGANISM: Artificial Sequence
<220> FEATURE:
<223> OTHER INFORMATION: PCR Primer

<400> SEQUENCE: 62
aattctatgt atgtgtgtgt ttgtgtgtgt gtg                                  33

<210> SEQ ID NO 63
<211> LENGTH: 33
<212> TYPE: DNA
<213> ORGANISM: Artificial Sequence
<220> FEATURE:
<223> OTHER INFORMATION: PCR Primer

<400> SEQUENCE: 63
aattcacaca cacacaaaca cacacataca tag                                  33

<210> SEQ ID NO 64
<211> LENGTH: 38
<212> TYPE: DNA
<213> ORGANISM: Artificial Sequence
<220> FEATURE:
<223> OTHER INFORMATION: PCR Primer

<400> SEQUENCE: 64
agcttaataa ataaatattt ctctatcttt aaaggcac                             38

<210> SEQ ID NO 65
<211> LENGTH: 39
<212> TYPE: DNA
<213> ORGANISM: Artificial Sequence
<220> FEATURE:
<223> OTHER INFORMATION: PCR Primer

<400> SEQUENCE: 65
tcgagtgcct ttaaagatag agaaatattt atttattaa                            39

<210> SEQ ID NO 66
<211> LENGTH: 6953
<212> TYPE: DNA
<213> ORGANISM: Homo sapiens

<400> SEQUENCE: 66
gttaacagtc aggcgcatgg gccatggagc ctcctgggtg tcagatccca gttcagcccc      60
tgcttgccaa gagcccttgg cctctgtgaa ccctggtctc ttcttgtgta tcctggggac     120
catcaccctg gataagcctg cgtcgggctg gaaggactga acgcccaggg cattgaaggg     180
gctttgtggt aggggccact ggctggccca cgtccctgga accagaggtg accctgatgg     240
ggccattgtt attggggtcc tcaggtgtgg gcagctggtg acgggggtgg cccacagccc     300
cccctcgacg ctggtgtgga agggccagag cagctggggc acgggcgaga cttccgcacc     360

```
gtcctggtta acgcggatgg cgaggtgggt gtgtgtggct tggggggtgc tcggctggag    420
tcctgggcag ggtctgggca ccctcggggc cgccacagca gctctgggcc gatcccggga    480
catgccgccg tgtcctgtcc cgcacaggaa gtggccatga ggactgtgaa gaagtcctcg    540
gtgatgcgtg agaatgagaa tggggaggaa gaggaggagg aagccgagtt tggcgaggag    600
gatcttttcc accaacaggt aggacccctg tgcccacttg cggctggggg gcagcctctg    660
gggcagagtg agctcgtgca cacacataca catgcgtgct ggccgcatcc ccgacgggag    720
ctccatctgg ctgccgtggc tcagggtgaa gccagccttg ctgttaccag cacggcagag    780
acctgttctt tcctcctggg tcgtgcccat cgtgtgaatt tgcgacatca cagacctcag    840
ggtagctggc caggggatc cctgagaggt gggtgttgaa cagctcccaa atgctctctc    900
ctcaaccggc ttcctcagtc gaagaagcag ccagtcctct actgctctgg gagaagatga    960
gtcagaaacc acagctgcat aaacgcgtg cgtcgcaagt tcctgtgact gttttggaac    1020
ccagaacaga atgtgtagct cacaggcggg ctcatgggga catggaagtg gaatggaagg    1080
ctctagaaat agacactgtt gttgctcagc ccctccctgg tggggaggtg ggggcagcca    1140
tctacctgcc ggctgcctcc aggctggccc tcatcatggc cgaccttcct tccttccttc    1200
ctgaaggggg acccgaggac cacctcaaga ggctgctacg tgatgtgaac ccacactcct    1260
catccacaca cctttcttta cccagagcca ctgaaaacta ttttttatca ttggctttct    1320
ttagttcttg atacatttct agagaatttc taagcgaact gccagaacgt gtgggtgggt    1380
ctcccccagc cctccctcct ggcgggtctc ctccagcctc acttcgctgc acttcgccg     1440 ctgccccgga acttttcaa tcccacccca ctcctcatct caccatttgg tcaaattgga    1500
agcccagggc caggacccgg aggtttagaa gatgcttggg cttggaggga ggagggccgg    1560
cgaggctagc gaggggacag gagacggccc tgctgcggac ggagcgcgga aactgcgtag    1620
gaattcagtg gtggtgggtt tttttaaggc tttctacaaa accaaattca gaatccaggc    1680
gtcgacctgg tggggcccgg ggcaagcctg cattctggct gcccagcttc ggacagcggg    1740
aactcctcag gcagccacgc agcgggtgtg ggccagcatg gggatggcgt ggccccaggg    1800
gggttttcac tccgctgcct gggcttccag attcccgttc tggcagcgac cggccgggtt    1860
tctcggaccg ttgactttat ttgggggagt ttttcccgcag ttcagttcct gactgtgcaa    1920
ggccaacagg gcaggggagg ggaagacctg gggaaggaag aatgaggaca cagtcccgtc    1980
gtaagacctg tcacaacaat aagcaggag gggagatgtg gaggggacac atctggttgc    2040
cttggaggca gaagctgtga gtttcagaac agctgtctgc agggaacgcc accatgttga    2100
ccctctggag gagagcgctg tggagcccct ccgtgttcc agctccgtct gcctgtgcc     2160 tatatatcac atgcgtctat catactgtgt ctttatctgt gattttttctc gctgaaacat    2220 gtttctcaga cagccaaggc cacctgactc ctatcacgac gcacccaagc ccctcagtcc    2280
agcttcccaa tgcctggcac cccttcggc aatagctcac cgtttacacc ctccctcata    2340
gatacacaga agttatttttt ttaatggata tttattttttt tacattggtc agtacacagg    2400
tcagggagct cacgccaggg ccttgaggac aggctgaccc tcctcccgg ggtggcgtgg    2460 ggctggggca cccccgacgg cagagcctcc ttcagaaagt gcagctcaag tcttaaagac    2520
accaaaactg agccatgggc acgcgccgtc tccgggccat ggcgttcact gcagggcggg    2580
ggcggcaccg ctcccctgtg actgcatccc gcctccctgg ggacctgcct gtggcaggaa    2640
ggaatggggg gccccagccc aggccgggaa ggagccagcg gccgacaaag cagaaacacc    2700
```

```
gctgctccac gtagccoctg ctggctgtcc ttgctctcag aagtcccggt cccatgtaga    2760
tagagcccgg cggatcttac caaagcattt cctcctggag gctacgccgc ttggtgctcc    2820
cagtgaggcg gctggtaggg agctttgcct gccccgggga taccctctac cagccgctgg    2880
aagtgggaat gctggcgaca gactgtgtct gtttcccacc ttcatagcag gaatcacccg    2940 gaccccgactg gctgggcttc gtgctagcga gggttttctg ggggtgggtc ttggtgatct    3000
tgtcctatgg ggatctctgc agtggtctca gccacatcct agtatatttt ggctctggag    3060
gagcaaagct gtatcctgga gttggtctgt gatttgccga cagacttgca ggctgggctc    3120
agcaaagtcc cccccaaaac ccgcaggtcc tcatgtccag acgctgccag tcctgtcctg    3180
aaaacagcac gccccaggcc cacagaaccc cccaccctac atttgccttg ggtggagctg    3240 gggtggtcc taggactgcg ggtgcccta gctgaagggg gcccgcagaa gcgtgagctg    3300
ggccgcctgt gggtcattgg aggttcattg agaattgagt cctttggaaa gactaagaaa    3360
atcaaatttt taaagttat ttatggcctg ggaaacaatt tgcatttgtc cccaaatacg    3420
cttagctgtg tgccgcttag aacgatgaga aaccatccct ctgtgtaagc ccgtgccgtg    3480
tgactcgaag cctagcgccc tccctgcgaa gcatcagacg ccacccagcc ctgggggagg    3540
cccacgcctg ctggaccaac gcgggttctg gggtgcacag cgccaggtta acgctgaagc    3600
ctgccccgct gagcccaaga gccggggaggc ctgcgggctg acccagaatc cgatcatgca    3660
cctgtcctca tgccagcggc tttggctggg gttggtctga agcctgcacg cggcagttct    3720
ttgttaaaga tctgagggac tcgtcagtcc tagcgtcgcc gcctgcagcc tcttccaagc    3780
cctgcgtcca gcgagcgtca cagcacaacc tgcaaaaacg gagctgggct gcagctgggg    3840
ctggcatgga cttttcatttc agagattcgg ttttaagaa gatgcatgcc tagcgtgttc    3900 ttttttttt ccaatgattt gtaatataca ttttatgact ggaaactttt ttgtacaaca    3960
ctccaataaa catttttgatt ttaggttctg cctctgagtt tattcctgag gggaagctcg    4020
agccgggcct ctgccctaat gaagcggatg tctaagaaag atccctccac ccccaaggaa    4080
aaaggtcact ggctagtgta gctagtgtaa acaggaccca ggcgatgcat gggaccctgc    4140
cctttttttt ctagtgagcc tccgacgctg ttgcacaagc tgactcttcg tcacgtgatg    4200
cgaccggctc cgccccggcg gcaacacgct gtatagacgc gccgggtgcc tcgtgcgcat    4260
gcgcggcagg cccttcggga cgagctggag gcagagcgtg agtacaaagt gatcggcctc    4320
ggccgacgca gtagccccc tactccccgg ccaagtcagg gcctccctct tcccgcggag    4380
tcgcaaccac gggtagctcg tgtaggtaac ggcaggtcca ggcctccgca tgagcggagg    4440 gcccccccgca cgaccttgaa tggcccggtg gcgcgcgcgg tcgtgtggga gttgtagtcc    4500
tccgtccccg tccgcgcgga ctccgtttcc cgtggtgccc cgggcggccc gcttccggcg    4560
cagttagtta cgagtcggcg cacgcggcct cggtccggtt gactttgcgg agccatggag    4620
ggcggcttcg gctccgattt cggggggctcc ggcagcggga agctggaccc agggctcata    4680
atggagcagg tgaaagtgca gatcgccgtg gccaacgcgc aggagctgct gcaggtgcgg    4740
ggctggccgg gacgggcgc tggggggcgac agggccaccc ctaggggccg acgtcgcggc    4800
taagcctcgc gtgtctccac agaggatgac ggacaagtgt tccggaagt gtatagggaa    4860 acctaggggc tccctagaca actccgagca ggtgagaccc gcggaaggtt cggggcaagg    4920
gtcgcgaggg cctagattcg ggggggaggt gtctgcgcgt gcgagacaac ggggaggtgc    4980
gacggagtgc tcactgcacg tgcgtagtct gcagcccggg cgtcctggag ccggggttag    5040
ggcggtcccc ggggccgcga agtcccgagc tgagccgtgc gcccctccgc tcccgcagaa    5100
```

-continued

```
gtgcatcgcc atgtgcatgg accgctacat ggacgcctgg aacaccgtgt ctcgcgccta      5160
caactcgcgg ctgcagcggg aacgagccaa catgtgaccg gcgagcgcgg gccacccac       5220 cctgtcattt ccataaacgg tttgagaggc ggggtccgat gtacgtactg cctgcccggg      5280
gctaggaggg tggcaccggt gctgggacac acgggactgt gtcctcgcca cccccgccc      5340 tgcccctgc cagccagtgc agcttggatc tcggggtgt ggggccctgt gcttcctgaa        5400
gtgctggcag cccagtggca cctccttcag gcctttgggg tattcccta gtgtgcccaa       5460 gtcagcctca tattctgggc ggacagcttg tctggacttc ggagttgggg gtggtcagac      5520
accacaggag ctgtcacctc ctgcggatgg gcaaataaat tggtggagga cggagagaaa     5580
cctctttatt tcctccttgt ccctggaacc ccagctcgga gggtctcagc ctcccctggg     5640
ttgggagaag tcatctttcc ccttagtgcc gccgggctgc tgagtcacga ggaatgtgtt    5700
gctgctgcca cccctgcccc aaaggctaag ggggacagcc ttccccttgt cagggcttgc     5760
tttgaccctg cttcgttcca ccccgggtcc tggtggagcc accaggcagg tggtcctcgc     5820
tgtgacactg aggtgctgag ccagtgagct agggtggagg ggctgtgttt ggaacaaagg    5880
gtggtaccaa aatgcatccc catgacccac agcccccca cacccgtcct tgggtagggt     5940 acggtgggt ggggtgttgg gtggcctgct gctcctgttg cttcacgta gagtctcggc      6000 ctgggcagtc acgtggtggt cactcctgga tgtgctgtcc tatccagcct ctcacagctg    6060
ccacccgggt atagacacct gggaagtggg gccggccaca gccatagccc agctagtga    6120 ccccagttag cacccaccgt ccagagggct ccctgcaacc aggggtcccc cagcgtcacc    6180
ctgttgggga gagaagaaag ggggttcaga ggccggtacc tcccctacag cagcccttgg   6240
gtcattggcc cctctaggag tgaccctagt gacttcccct ggagccgcat tttcactatc     6300
tggaaaatgg gctcaatcaa aggtggcaga catttatgga cacccgctac gtggtcccgg    6360
agtgaacggt tacctcccac tgcagcctct gcctgctctg ccgccgaggc ccggggatgg    6420
gatgcggtgg gttgcccaat aaacggctgt ggagtggaaa ttcctccgga gccaaaaagg   6480
ctccctgctt gatccgctgg agaagcctgc accgagggt ggctcccgga tggtgggctt     6540
cgtggcagcg ggaacccgcc ctccccggcg gctgggcggg acctggtccc ctgggccggg    6600
gcggggctca ccgagcagct gtccacgccc ctgcgggaa gccggcacac agcatgcggc    6660
tgctgatctg cactgggtag aagcggcggc aggtctgctc gctgaggagg cgcacggccg    6720
ccttctgcag ctgccgcgcc atggagcctg cggcggcga gcgagacggg gcgggtgggg   6780
accgcgtccc ggccgccccc cgagtccccg caccaccgcg gtccccgggc gcgcctacct    6840
ccttcgtcgc accgagcccc agccggtgat gacgcagcgg tgccgtccgg gggtcgcggc    6900
gcggctaggg caggcagatg ggacgcacca ggcggctgcg acgaccgtac ccc           6953
```

<210> SEQ ID NO 67
<211> LENGTH: 3311
<212> TYPE: DNA
<213> ORGANISM: Homo sapiens

<400> SEQUENCE: 67

```
ggatccttcc accttgccta ccaaagtggg gatgaaagtt tgtctggggc attgcagttt        60
tagacaggaa gaccagggaa ggcctcactg agaaggtgac atttgagcca agacttaaaa      120
aggtacgaaa gtgagccatg tggaagtctt gggggaggag gtgaactagg cagaggcaca      180
gctgggcaaa gggcctgagg tgtgaccatg cctatggatt tgaggaactt caaagaggct      240
```

-continued

```
gtgtgctgca ggagagtgaa gggcagggag tggcaggaaa tgaaggcaga caggtagcag      300
tggggaggac gcagggtcc agctcatgta ggtcttgatt ggacacagtg agtttcagat       360
gacagcctcc tgtctcatgg ggtagcccca aagccacagg agtctggtga tttccctctt     420
ccccaccaga catctatgcc atcggggtgg gcaagctgga tgtggactgg agagaactga     480
atgagctagg gtccaagaag gatggtgaga ggcatgcctt cattctgcag gacacaaagg     540
ctctgcacca ggtctttgaa catatgctgg gtgagtgagc tttgccctcc ttggtgtggg     600
gaggatggtg aggagcccgc caaaggcccg ttttgggaac ctggacacag tgcccctcac     660
ttgcctcctt ccccatctga tcctcacacc cacagatgtc tccaagctca cagacaccat    720
ctgcggggtg gggaacatgt cagcaaacgc ctctgaccag gagaggacac cctggcatgt     780
cactattaag gtaccaggaa ggaggggcag ggcttggatt ccagaggtaa aagcggccat     840
gggccagaca tactgcaatc tctgaaaatc acctgttccc ctgcagccca gagccaaga     900 gacctgccgg ggggccctca tctccgacca atgggtcctg acagcagctc attgcttccg     960
cgatggcaac gaccactccc tgtggagggt caatgtgggt aaggcagggg atgcaccagc    1020
ctcctgatcc gtgaagccac agatcctacc acctcaccca gcctctgcc cctgcaggag    1080 ccctggtcta gcctaatcta gtgtatcatt ccaggagac cccaaatccc agtggggcaa     1140
agaattcctt attgagaagg cggtgatctc cccaggtttt gatgtctttg ccaaaaagaa    1200
ccagggaatc ctggagttct atggtgatga catagctctg ctgaagctgg cccagaaagt   1260
aaagatgtcc acccatgcca ggtgcctgga gtcttgatg ggagggtgcc ctgcaggaa     1320 gagtgctctg gagatccctg aagagacta ctggggacag gctggtgtga cccttgctct    1380
tctccccagg cccatctgcc ttccctgcac gatggaggcc aatctggctc tgcggagacc   1440
tcaaggcagc acctgtaggg accatggtga gtgctgggac ttatggtgct tgagagctgg   1500 ggccgggtt tgggggtgat aacaaggact aggctgcagt ccccaagcca ggaacctgga    1560
ttctgggtaa aaggaccagc accaacatcc ccttctcttg actatagaga atgaactgct    1620
gaacaaacag agtgttcctg ctcattttgt cgccttgaat gggagcaaac tgaacattaa    1680
ccttaagatg ggagtggagg tgagggtctc aggttgggga tgctgggatc cccctgtgac   1740
agctcccaga atgtctctct tccttctcca ggtctggctg ctttctctct ctgacgcggg   1800
tcacccctcc tcccaagcct cacaaacctg ctaggtgtcc ctgggtctgc ttattctttt   1860
tttgttgtta ttgagatgga gtcttgctct gtctcccagg ctggagtgca gtggcacgac   1920
ctcagctcac tgcaacttct gcctcctggg ttcaagcgat tctcctactt cagcctcccg   1980
agtagctgag attacaggtg cccaccacca caccagctaa ttttgtatt tttagtagag   2040 acgggacttc gccatgttgg ccaggatggt cttgaactcc tgacctcaag tgatctgcct   2100
gcctcaacct cccaaagtgc tgagattaca ggcgtgagcc actgcacccc acccgggtct   2160
gcttattcta ccccttctctc tggttccacc cctgctgcag tggacaagct gtgccgaggt   2220
tgtctcccaa gaaaaaacca tgttcccaa cttgacagat gtcagggagg tggtgacaga   2280
ccagttccta tgcagtggga cccaggagga tgagagtccc tgcaagggtg agtccctcac   2340
catgcctgga ttcccaaggg gaaggccacc tgtgtctctg tggccagcat gcatgccaga   2400
acaccagtcc actgccctag atgacactgt ctcctgtcac cctttgctgg caggagaatc   2460
tgggggagca gttttccttg agcggagatt caggttttt caggtgagaa ggtagaagct    2520
tgcaggaccc agggggttaca ggatctcagc cttgttgggg ggatgaggga ggcctttgag   2580
ggatctaggg aggttggggc ttacagttgg ggctgtggca gcctcccagc cagttctctc   2640
```

```
cttttctcca ggtgggtctg gtgagctggg gtctttacaa cccctgcctt ggctctgctg    2700
acaaaaactc ccgcaaaagg gcccctcgta gcaaggtccc gccgccacga gactttcaca    2760
tcaatctctt ccgcatgcag ccctggctga ggcagcacct gggggatgtc ctgaattttt    2820 taccccctcta gccatggcca ctgagccctc tgctgccctg ccagaatctg ccgcccctcc    2880
atcttctacc tctgaatggc cacccttaga ccctgtgatc catcctctct cctagctgag    2940
taaatccggg tctctaggat gccagaggca gcgcacacaa gctgggaaat cctcagggct    3000
cctaccagca ggactgcctc gctgccccac ctcccgctcc ttggcctgtc ccagattcc    3060 ttccctggtt gacttgactc atgcttgttt cactttcaca tggaatttcc cagttatgaa    3120
attaataaaa atcaatggtt tccacatctc tcagtgcctc tatctggagg ccaggtaggg    3180
ctggccttgg gggaggggga ggccagaatg actccaagag ctacaggaag gcaggtcaga    3240
gaccccactg gacaaacagt ggctggactc tgcaccataa cacacaatca acaggggagt    3300
gagctggatc c                                                        3311

<210> SEQ ID NO 68
<211> LENGTH: 3107
<212> TYPE: DNA
<213> ORGANISM: Homo sapiens

<400> SEQUENCE: 68
ctgcagtgaa cggtgatcac accactgcac accagcctgg ggacacagcc agactttgtc      60
acaaaaaagc aaaacaact ggccagtgta tgagggctc gtgttttttg tttgtctgtt      120
tgttgagaca gagtctcact ctgtcgccag actggaatgc agtggcacat tctcggccca     180
ctgcaatctc tgcctcctag gttcaagcaa ttatctgcct cagcctccca gtagctggg     240 attacaggcg cccgcaccac gcccggctaa tttttttgta ttttagtag gacggggtt     300 tcaccacctt ggccaggctg gtcttgaacc cctgacctca tgatccaccc gcctcggcct    360
cccaaagtgc tgggattaca ggcgtgagcc tccgcccgg caggggcgc gcgtttttaa     420 aacatgggag agggaattgt gcttcacaat caccatcagg tgtctcgata tcgggtgcca     480
cgccgtcccg cttctgaggc gcggcggccc actttggcag gccgaggcgg gtggattacc     540
tgaggtcagg agttcgagac cagcctgaca acatggtga acccccgtct ctactaaaaa     600
tacaaaaaat tagccggacg tggtggcgca tgcctgtaat cccagctact gggaggctg     660 aggcaggaga atcgcttgaa cccgggaggc ggaggttgcg atgagccgag atcgcgccat    720
tgcactccag cctgggaaac aagagcgaaa tccgtctcaa gaaaaaaaag gaaagacccc    780
ccctccttct cccgccggaa ataccctctt tcaggacggc gcgcctgtgc ggcgacgcgc    840
gctcagttac ttagcaacct cggcgctaag ccaccccagg tggagcccag caacaacaga    900
gccaccgcgt cccccaccaa tcagcgccga cctcgccttc gcaggcctaa ccaatcagtg    960
ccggcgctgc aaggaagttt ccagagcttt cgaggaaggt ttcttcaact caaattcatc   1020
cgcctgataa ttttcttata ttttcctaaa gaaggaagag aagcgcatag aggagaaggg   1080
aaataatttt ttaggagcct ttcttacggc tatgaggaat ttgggctca gttgaaaagc    1140 ctaaactgcc tctcgggagg ttgggcgcgg cgaactactt tcagcggcgc acggagacgg   1200
cgtctacgtg aggggtgata agtgacgcaa cactcgttgc ataaatttgc ctccgccagc   1260
ccggagcatt taggggcggt tggctttgtt gggtgagctt gtttgtgtcc ctgtgggtgg   1320
acgtggttgg tgattggcag gatcctggta tccgctaaca ggtactggcc cgcagccgta   1380
```

```
acgaccttgg gggggtgtga gagggggaa tgggtgaggt caagtggag gcttcttggg    1440 gttgggtggg ccgctgaggg gagggcgtgg gggaggggag ggcgaggtga cgcggcgctg    1500
ggcctttccg ggacagtggg ccttgttgac ctgaggggg cgaggcggt tggcgcgcgc    1560 gggttgacgg aaactaacgg acgcctaacc gatcggcgat tctgtcgagt ttacttcgcg    1620
gggaaggcgg aaaagaggta gtttgtgtgg tttctggaag cctttacttt ggaatcccag    1680
tgtgagaaag gtgccccttc ttgtgtttca atgggatttt tatttcgcga gtcttgtggg    1740
tttggttttg ttttcagttt gcctaacacc gtgcttaggt ttgaggcaga ttggagttcg    1800 gtcggggag tttgaatatc cggaacagtt agtggggaaa gctgtggacg cttggtaaga    1860
gagcgctctg gattttccgc tgttgacgtt gaaaccttga atgacgaatt tcgtattaag    1920
tgacttagcc ttgtaaaatt gaggggaggc ttgcggaata ttaacgtatt taaggcattt    1980
tgaaggaata gttgctaatt tgaagaata ttaggtgtaa aagcaagaaa tacaatgatc    2040
ctgaggtgac acgcttatgt tttactttta aactaggtca aaatgcagat cttcgtgaaa    2100 accccttaccg gcaagaccat cacccttgag gtggagccca gtgacaccat cgaaaatgtg    2160
aaggccaaga tccaggataa ggaaggcatt cccccgacc agcagaggct catctttgca    2220
ggcaagcagc tggaagatgg ccgtactctt tctgactaca acatccagaa ggagtcgacc    2280
ctgcacctgg tcctgcgtct gagaggtggt atgcagatct tcgtgaagac cctgaccggc    2340
aagaccatca ccctggaagt ggagcccagt gacaccatcg aaaatgtgaa ggccaagatc    2400
caggataaag aaggcatccc tcccgaccag cagaggctca tctttgcagg caagcagctg    2460
gaagatggcc gcactctttc tgactacaac atccagaagg agtcgaccct gcacctggtc    2520
ctgcgtctga gaggtggtat gcagatcttc gtgaagaccc tgaccggcaa gaccatcact    2580
ctggaagtgg agcccagtga caccatcgaa aatgtgaagg ccaagatcca agataaagaa    2640
ggcatccctc ccgaccagca gaggctcatc tttgcaggca agcagctgga agatggccgc    2700
actctttctg actacaacat ccagaaggag tcgaccctgc acctggtcct gcgcctgagg    2760
ggtggctgtt aattcttcag tcatggcatt cgcagtgccc agtgatggca ttactctgca    2820
ctatagccat ttgccccaac ttaagtttag aaattacaag tttcagtaat agctgaacct    2880
gttcaaaatg ttaataaagg tttcgttgca tggtagcata cttggtgttt tgtcatgaaa    2940
ttctctagtg atgtgtgggt acgcttaaaa ctggtgaaaa tgtttaggga tttaattttg    3000
agattggtaa tgtgctcaaa gttaagtcac ttgactttgg tatacacttg ggtgggctga    3060
ggggcaagag ccttctttgc tgtttaagtc attacaagtt aggatcc    3107

<210> SEQ ID NO 69
<211> LENGTH: 2878
<212> TYPE: DNA
<213> ORGANISM: Saccharomyces cerevisiae

<400> SEQUENCE: 69
tacatcccgt tcacatagct ccttcctggt acttgagtaa gtcttttaaa acaattcaac      60
atctactttg tatcaggcgc ttggatttac acttttggca tatttattcc tacgctgcat     120
ttgctattag ccgcggaaag gaagtacaat aacgtttac gtcgattcgt gtttgtatta     180
cccagcacct ttttcttctt gaagatgtat cgacccgtgc cccgctgta gtagcccgc      240 gcactttgtg tgtgcagcaa cttcaggctt gctccgtgaa ctcacaacgt cggccgtcgt     300
gcttgtcgcg tcgtcgcgaa gtatttaaac aaagcgggtt tttcttgtcc cttaattaag     360
cctactgggt cgctccttcc caaataattt gatttttct cccttgccac agtaaacaag      420
```

```
ctaaaaggcg gtcgaatctc aacggctctg ataaacgtac gtaatgaccg atatcacacc      480
cgtacagaac gatgtggatg tcaatggtaa taatgtcaat gacgacgttt ccagtaatct      540
aaagaggcct atagatcaag gggatccttc gaatggactc gcagaagaag aaaaccccgc      600
caataaccag ttgcatctca aaaaggctag actggatgga gatgctctaa catcatcgcc      660
tgctggactt gcagagaacg gtattgaagg cgccaccctg gcggctaacg gggaaaatgg      720
gtataacgcc accggaagtc gagaagacga acagcagggg ttgaagaagg aagaaggagg      780
acaaggtacc aaacaagagg atttagatga aaactcaaaa caagaacttc cgatggaggt      840
tccaaaggaa cctgcccctg ctcctcctcc agagcccgat atgaataatc tccctcagaa      900
tccaatacca aagcaccagc agaaacatgc attgcttgcg attaaagctg tcaaacgctt      960
gaaggatgcg agacccttc tacaacctgt tgacccagtg aaattggata ttccctttta     1020
ctttaactac ataaagaggc caatggactt gtctactata gagaggaagt tgaacgtagg     1080
cgcttatgaa gttccggagc aaatcacgga ggatttcaat ctcatggtta acaacagtat     1140
taaattcaac ggtccaaatg cgggcatatc acaaatggca agaaacatac aagcttcttt     1200
cgagaaacat atgctaaata tgcctgctaa ggatgctcca cctgtaatag ccaagggacg     1260
gcggtctagt gcccaagagg atgccccaat tgtaattaga cgagcccaaa ctcataatgg     1320
gaggccgaaa aggactatac atccgccgaa atcaaaggat atttatcctt atgaatcgaa     1380
gaaaccgaaa tccaaaagac tacaacaagc aatgaaattt tgtcagagtg tgctaaagga     1440
attgatggcc aagaagcacg cctcttataa ctacccattt ttggaaccag tagacccagt     1500
ttctatgaat ttgccgactt atttcgatta tgttaaagag ccaatggatt taggcacaat     1560
cgccaagaaa ttaaatgact ggcagtatca acaatggag gattttgaga gagacgtgag     1620
gttggtcttt aaaaactgct acacgttcaa tccggatggc acgatcgtta atatgatggg     1680
tcatcgtcta gaggaagttt tcaattccaa atgggcggat aggcctaatt tggatgacta     1740
cgattccgat gaagattcga ggacccaagg cgactacgac gattatgaat ctgagtattc     1800
agagtctgac atcgatgaaa ctataattac aaatccagcc atccagtatt ggaagaaca     1860 acttgctcgg atgaaagtgg agttgcaaca attaaaaaag caagaactgg aaaaaataag     1920
aaaagagagg cgcttagcac gtggatcaaa gaaacgcggc aaaagatcga agggaaggag     1980
tgggtctaag aacgcttctt cgaaaggaag gcgagataaa aagaataaat tgaaaacagt     2040
agtgacatat gatatgaaac gtatcattac agagaggatc aatgatttac caacttccaa     2100
attagaaaga gcaatcgaca taataaaaaa atccatgccc aatatttctg aagacgatga     2160
agtagaactt gacctcgaca ctttagataa tcacaccatc ttaacattgt acaacacttt     2220
ctttagacaa tatgaaagct catccggtgc ttctaacggt ttggacggta cttcaggtgt     2280
tacgcgagat gcttcgtcct tgtcgcctac aagtgcggga agcagaaaga gaagatctaa     2340
ggcattaagc caagaggagc agagtaggca gatagaaaag ataaaaaata aactagctat     2400
cttagacagt gcttcacctc tgagccaaaa cggctcccca ggccaaattc aaagcgctgc     2460
acacaacggg ttttcctcat cttcagatga cgatgttagc agcgaaagtg aagaagagtg     2520
actgaatttt gaatttgatt atcttcaacg actgagaaga atgagcacca ttttgatatt     2580
ttgattaatt aagtggtaat cttaagctca tatacaaaaa gggaaggaaa aaaaataaag     2640
atagaaaaga tcttaggaac ggatagaggt ttgaaaaagg aataacaggt aattttcat      2700 tttcatatcg gttgtaacat tataaagctc acaaatttaa aacaaaaaaa aacataaacc     2760
```

-continued

```
taacaaggtt aatcatttgc acatgatctc atcatataga tcaattcata atctatataa    2820
taatgaataa ttataataaa aatttcctct tgtctcagaa cgcccatcgg atggcata      2878
```

<210> SEQ ID NO 70
<211> LENGTH: 3379
<212> TYPE: DNA
<213> ORGANISM: Saccharomyces cerevisiae

<400> SEQUENCE: 70

```
taacgagcaa ttcagtactt cttccaataa tgcttaacat gattgcccaa gacaaatctt      60
caacaaccgc gtatcaaatt ctgtgtcgaa gaagaggtcc tccaattcag aattttcaaa     120
tttttccctt accggctgta acgtacaata agtagcatgc ataaaatata atttaatcaa     180
atacttttgg gcaattaaaa tttagttaa caatagttat gcaatgcgct ttatgttcat      240
atgataccgt ttataagcta ttgccatatc cttatcttat tgcttccagt agcctcgagt     300
cgaccactaa aaagatgtca cttaagacgg aaattatgta gctgcacttc tttttaaca     360 agttcggtcg gcccttcaag ttctccttc taaagcctca ttatttattg cgtagatgct     420
aaatgttatc gcggtttagc ttgcatgtta cgtttccgtt ttagaacctg gtcgagtagc     480
gaataatgtc ttcagttgat gtactgttaa cagtaggtaa gttggatgcc tcattggcgt     540
tactgactac tcaggatcat catgttattg agtttcctac agtattatta ccagaaaatg     600
ttaaagctgg atctatcata aaaatgcaag tttcacaaaa tttagaggag gaaaaaaaac     660
aaaggaatca ttttaagagt atacaagcca aaattttgga gaagtatggt acccataaac     720
cggagagccc agttttgaaa attgttaacg ttacgcaaac gagctgtgtt ctagcatggg     780
atccattgaa acttggctca gcaaaattga atcactgat ccttatagg aagggaatac      840 gttcaatggt aattccaaat ccattcaaag tgactaccac gaaaatatcc ggtctttccg     900
ttgatacgcc atacgaattt caattgaaac tgataaccac gtcaggaaca ttatggtctg     960
aaaaggttat attgcgtaca cataagatga ctgacatgtc tggtatcact gtatgtttgg    1020
gtccattgga tccattgaaa gaaatttcag acttacagat atcccaatgt ttgtctcaca    1080
tcggggcgag acctttacaa cgtcatgttg cgatagatac tacgcatttt gtctgtaacg    1140
atctagacaa tgaagaaagc aatgaagagc ttataagggc aaaacataac aacataccaa    1200
ttgtcagacc ggaatgggtg agagcttgtg aggttgagaa aagaatcgtt ggtgttagag    1260
gattttactt agatgcagat caaagtatac tgaaaaacta cacattccca ccagttaatg    1320
aggaagaact ttcgtactca aaggagaatg agccggtagc cgaagtagcg gatgaaaata    1380
agatgcccga ggacacaaca gatgtcgaac aggttgcatc acctaatgac aatgagagta    1440
atccttcaga agctaaggaa caaggagaaa agagtggaca tgaaactgcc ccagtaagtc    1500
ctgtagaaga tccattgcat gcttcgacgg ctttggagaa tgaaaccacc atcgaaaccg    1560
tcaacccctc cgtaagaagt ttgaaaagcg aacctgttgg tactcccaat atagaggaaa    1620
acaaagcgga ctcttccgca gaagccgtgg tagaagaacc gaatgaagct gtggctgaaa    1680
gttctccaaa tgaagaagca acgggacaga aaagtgagga taccgataca cattctaacg    1740
aacaagctga taatggattt gtacagactg aagaagtagc tgaaaacaac ataaccacag    1800
aaagtgcagg ggaaaataac gaacctgcag atgatgcagc aatggaattt ggacgtccag    1860
aagctgaaat tgaaactcca gaagtaaatg agtctataga agatgccaat gaacctgcgg    1920
aggattccaa tgaacctgtg gaggattcca acaaacctgt gaaggattcc aacaaacctg    1980
tggaggattc caacaaacct gtggaggatt ccaacaaacc tgtggaggat tccaacaaac    2040
```

```
ctgtggagga tgccaatgaa cctgtggaag ataccagtga acctgtggag gatgccggtg      2100
aacccgtaca agaaaccaac gagtttacta ccgacattgc ctctccaaga catcaagaag      2160
aagatataga acttgaagcc gaacctaaag atgctaccga aagtgttgca gtcgagccat      2220
ccaatgaaga tgtaaaacca gaagaaaaag gttcagaggc agaagacgat atcaacaacg      2280
tttccaagga ggctgcctct ggtgagagta ctacccacca aaaaactgag gcctctgctt      2340
ctcttgaaag cagtgccgtc acggaagaac aagagacaac ggaagccgaa gtaaatacag      2400
atgacgtttt gtccactaaa gaagctaaaa aaatactgg caacagcaac agtaataaga      2460
agaagaataa gaagaataag aagaaaggga aaagaaatg attaatggat gccttcaatg       2520
agttccacga cgcacgttta ttttttcgac tgagaatccc tcagcaaata taatctattt      2580
tttatatatc tgtgtatatg taagcatgta taactagtta caaatatgat aactgctttg      2640
gcgatcactt cattttcttg agaggggtac tcagtagccg ccaagcacga aatgtccgtt      2700
attaaaaatt ggggagtgaa tcttaaaagc ccgaaaagga aattcaaaat ctgtctattt      2760
ataggccgtc gcgctctacg aaaacgcgaa attattcaaa cggaaaacgg aaaaaaatct      2820
aaaaaaagaa attaattgag agatctcacg gaaatgccgc gaggaatgtt tctcgaggct      2880
gagcggcgtg gtctgtgcaa aaaaatggca atttttttgt aggagtttgc attgggccat      2940
tcagaaggag caccgttaga tgggatggta aatgaatttg ctgtttcaga tttgaatcaa      3000
tctttacccg ttattttttgc cgttttgctt tcataatctg caaattaaca aagtcataaa      3060
gaacataaag acatcacccc agtttttaca ctctttttc ctgtgtttgg tttagcacaa       3120
ctttccaata accaagttgg tttcagatca tccccatatt attttctagt ttcatttact      3180
taccaaactc accattcaag gctttcaaat taagttacga gtacagtgga ccattttttt      3240
ctgattcttc atattttccg ttataagtct tataaggaag gtatacattt atattgcgaa      3300
tttgaaaaat aatttaaagc tgactttgcg ttttaggtag gctagaaaag aatacaacta      3360
tccctaaaca cattctaga                                                  3379
```

<210> SEQ ID NO 71
<211> LENGTH: 3233
<212> TYPE: DNA
<213> ORGANISM: Saccharomyces cerevisiae

<400> SEQUENCE: 71

```
ttgctacaaa aatgaaacct cttattatag taatcatagg agtaaagaaa atgttcttta        60
tcgcctgaaa catcgttacc ttcctcatct tgatgctgaa agtaaattga tggagtcaag       120
cggttcacca atagcgggat ttcatcgcct gagtgatatg ttgtgggaga taggcctggc       180
aaggaaaatc ctttagttaa agttgcatag caataaatca gcaaccaaac acctcgtttc      240
attaccgatt attaattatc aatatgtgta ctaatataat tgtcaaaatt tatgatgtaa      300
atttagggtt cccaacatat tttactcaac tgtaaacaag tcataatttc ctcggacaaa      360
attaggcaaa ataacagaaa aaccaatgga tgggatgggt aggaaaatga gtaagtaacc      420
caaacaaacg gtacctcttt attcagtcgg ctttacagat actgaggtaa cttataatgg      480
ttttttctta tgagcactat atgaatctcc ttttccattt ggataacagt aaagaaacgg      540
tgcctccaga gattgcaaaa agaataattt caaatgctat agctcctgta ataacagtta      600
cttcaactcc tctcttcgac aaacatattc aagaaacgta caagtagat tctctctata       660 tgctgctgcg attctttggc ggttgtgtct ctgatagaga tcaagccaat gaagcgaagg      720
```

```
ttggacagca tgagcatgag gtttgtgatg caagtgactc gacggattca attcccaaaa      780
ataaaaattt ggaagtgccc aatttatcaa agaaaggtag tcgcagtagg tcgaatagtc      840
ttttccagag ggattcaacg caatctcaat atatcaggtt tacaaggcca ttaggtgact      900
tgatcgaaac aagagatgca aatgatatgt tattcaatta ccattcttta gaggtattct      960
tagataatta tttgaaattg gttgcagcaa atactgatga aatggttcct cataatcttc     1020
ttaagaaatc catttatcat agtttctttt cactagcaat ttcatccaca aataacttat     1080
cgccctatga aacttttaat caccctattc tttccttgat tgctttagat atatcaaatg     1140
gcgaagttta tgaggatgca agagatcttt tagtcaattt caagaatctt aatcataata     1200
ctgaaaactt tcctatcttc atgaatacaa atgaaatgct tccagttttc ttactctgct     1260
acaatgacga ttcccaagaa gaattcgaaa atgccaggc gttacgtaag aaactaaga      1320 agcagttgtt tgttgagagt atcttactag cactctggaa ggattctttt atttacgacg     1380
aaaattcagt catacagtta caccaaccag taatgtcatc gcttgaagaa attctcttct     1440
tccttcaagc tccaactcaa acaacactct ctctggcttt gataaactcg atctatgata     1500
tgcttgatta tttggtttat gatttaatga taccattcat gaaagaaaaa gtgtcattct     1560
gggaagagac aatttacag ccaagaaagt cgctatttaa tggtgcaaag ttttcaaaa      1620 aatttatgaa taaaaatcct gtcaatggta atcaccaaca taattctcta acgagagaca     1680
gccagggaaa tgaatacttc gcatcgtcat cttctgagtt tttgatgaga aagttagcag     1740
attggtctat gatgctatcc gacttcaaaa ctgcttattc cacatacgaa tcgcttatgg     1800
atgacctaga tgcatttcca agtacctggc catcatgcat cgaatggtgc gcggtatcac     1860
tattgatggg tgcgcagagc atagtcaccg tgaaaatgat caaaaacgat ataaatcctc     1920
ttatcgaaag ggcattagcc acatacgaaa actgctcacg aatacaacgt ggtaaaggca     1980
aagaatcaaa ctctttggat gttacagagc cagtgcgttc gtatgagaca cgttgtatga     2040
ttttggcatc tgaattgttt ttatctttaa gcaatacgtg gacatctacc ccatacgcta     2100
tccaatattt agaaacaatt ctagacgagt gcaagttggg accttgttca cagataatgg     2160
tttgggaaag gcttagtgac tgctataatt tgagagttga ccctagaatc aaacatagag     2220
ttggagcaat gaagaaggac gctaaagaca ccgaagatct ccgaggtgag cataagtata     2280
gcacagatca tttcacagac gaggacatat tatcggaagg gttaacaaga agacgcaagg     2340 cagcttttt taggttaata gcagctaaga agtgggcaga gcaaaaacaa tggagacagg     2400
tttcttggtg cttaaaagat attgaaagta cctattcaga gatcaaattt ttgcatggta     2460
acggtttaat tttaagcaaa ctaaaaaatc aactcaattt aaaggacgtg gattctgcac     2520
cacggccctc cgaaaagaat cttacaagaa caagtgttag ctttattgga tgactttatg     2580
gaaaattcat gttttgagta taaattatac gtacgaatct tatagatata tattttctt      2640 ttaaaactcc atttcagctc ataagccgat acaaacacct tctatatatt atttctctaa     2700
cagctatgtt aacatgattg cctttgttta tctactaaag gacccttcta ctttatctac     2760
catacgccta tattttctct gtgtttcaat catatcgaga aaaatttggt acttcgtgtc     2820
taaaagaatt ctatctggat gagttttctc atttggattg acaattcttg cattacccgt     2880
tagctcttgc ataactttcc atagaaaact tgtcccgtta tatcttccct ctcctaggct     2940
ctcctgtccc acggtcaatg aagcatcctt actactttcc tcagaggttt tgtcaagtgg     3000
ttgttgtgtg caaatcggaa gagaatagtt atttattttg gcaggcgcac ttggagttga     3060
aagttgtaga ttatgtgggg atacaaagcc atttgtcgag tttcgatctt ccattgataa     3120
```

```
ctttttgtatc gacgaatatg aatcgttaaa acgttccgtc tttgtctgag aagatttttg    3180
gcctttgaga gttctttttt ccctggtata atcaaaatct tcacttgctg cag            3233

<210> SEQ ID NO 72
<211> LENGTH: 1775
<212> TYPE: DNA
<213> ORGANISM: Saccharomyces cerevisiae

<400> SEQUENCE: 72
cgtcaattca ttgcttgaga tattaacgcg ttaggttgtg ttcttcaatg atgggcaatg      60
caatttggcg ttaacgcctt ggaagcaata aggtaacagc gaaatttatg acatattatt     120
tcgaaccttt tacaaactag tagatttagt gatttattac ctattggcat tcatttgtgt     180
tctatatgtg gatgaggata gccgcctttc ttctcatcgg aggccatatc atctttcgac     240 aatcctttt aaatactatt tccatccgtg cctctaatag atttgtgtag ttgtctgggt     300
gcaatctttc catttttgct gaacttttt ttttttttca tgttttcag attctgaagt     360 accgcaatag gatatggcgg ataatcccta atgatccgcc tcatactagc cattacccat     420
ctatcccagg cattatgggt atgcaactca taatctcaaa tacacaaata agagcaacct     480
tatatatcac tttttcccgt tcagcaagag gtaaagccac caaaggttca aaatgcaaat     540
gtatgttacg gcgaatacag aatactatgt tcgaaataat atgaggatta tacgatagca     600
aaaaagccat aaacgaaaga cataaatgga aatgattga caagctcaca atttattaaa     660
caagtagcaa ttgagaaaaa ctattacctg cggcaagctt ctgagtttac attaaatctg     720
tagagcaaat tgaaaatgtc gcatatgtgc tgaagggttt gtttgttcca tcttattttg     780
cataacatag ttatatttac ttggtcgcat aaaaaatatt ttttactaac gtgaagtttc     840 ttctttatg atgtacgcac gcacgtctgt cttactccat aaatgaactt attccaattt     900
tgtacagctt cgttaagact ttgactggta agaccatcac tttggaagtt gaatcttctg     960
acaccattga caatgtcaag tccaagatcc aagacaagga aggtatccca cctgaccaac    1020
aaagattgat ctttgctggt aagcaattgg aagacggtag aactctatct gactacaaca    1080
tccaaaagga atccactta catttggtct tgagattaag aggtggtatc attgaaccat    1140
ctttgaaagc cttggcttcc aaatacaact gtgacaaatc tgtttgtcgt aaatgttacg    1200
ccagattacc accaagagct accaactgta gaaagagaaa gtgtggtcac accaaccaat    1260
tgcgtccaaa gaagaagttg aaataatcga tttattacga tctccacaaa tccaaagttt    1320
gtatacatca cgattttttt actacatata tatttccttt tctattctat ttgtaaatgg    1380
gaggaaatct taatatggac ctctcttcac aaattgttct ataatacaat atatatcaag    1440 ataataac aagtcatttg agataatggt atgcaaatac gcgaaataag agtaaacgga    1500
tacagtgagc ctgaagagga caagctgctt ccatgttgta gtgtttagat atatgagctt    1560
aaaatttaga tttactgaat attatacaat agtaattata cataaagaaa ttccatttta    1620
tctgttcgat agcaatggaa gaggagagag ttctgtgaaa caaataacag cagcacagaa    1680
aactcccgtc aacgtaatat ggttaaaaaa aaaaaaaaa aaaggacag taaagttaaa    1740 ttaaaacgca ctaaataatt tggtggtgga tcctt                                1775

<210> SEQ ID NO 73
<211> LENGTH: 967
<212> TYPE: DNA
<213> ORGANISM: Saccharomyces cerevisiae
```

-continued

```
<400> SEQUENCE: 73
gatcaacaga gattgatttt tgccggtaag caactagaag atggtagaac cttgtctgac      60
tacaacatcc aaaaggaatc tactcttcac ttggtgttga gactgagagg tggtatgcaa     120
attttcgtca aaactctaac agggaagact ataaccctag aggttgaatc ttccgacact     180
attgacaacg tcaaaagtaa aattcaagat aaagaaggta ccctccgga tcaacagaga      240 ttgattttg ctggtaagca actagaagat ggtagaacct tgtctgacta caacatccaa      300
aaggaatcta ctcttcactt ggtgttgaga ctgagaggtg gtatgcaaat tttcgtcaaa     360
actctaacag ggaagactat aaccctgag gttgaatctt ccgacactat tgacaacgtt      420
aagtcaaaaa ttcaagacaa ggaaggtatt cctccagacc aacaagatt gatctttgcc      480 ggtaaccaac tagaagatgg tagaacgctg tcggactaca atattcaaaa ggagtccact     540
cttcacctcg tcttgaggtt gagggtggt aactgatcac tcctcgcaat attttcatta     600
tgtcaatata tatatattta ctctcctttt ttggttttt ttttttttt gataaatact       660 ccatagaaca ctaaataaat tgttcaactg tgttattgtc tttattcatg ttggttttca    720
agagcttgga ttttgaatcg tcttatacta tgacgttcac tattttcgcg aacccgggta     780
ataccattag ctattttgat agaaagggat tttattaggg aatataacca caatttaaag    840
tgtcctatca tgtttcaatc tccagtaaac gcacataagc cgaccaattg agtcaacctt     900
ttaactctat ttaatttgat acggatagaa tattgtgact accaaaaggg aaaaggcaga    960
aaaaagg                                                               967

<210> SEQ ID NO 74
<211> LENGTH: 2010
<212> TYPE: DNA
<213> ORGANISM: Saccharomyces cerevisiae

<400> SEQUENCE: 74
aaaaaagagt tactagccgt atatggatgt ttgaagatac atggaaaccg tctctggtgt      60
cgtgtatata agaaacttct agttttattc agacgcactc attatctttg ctacataaca    120
tttctctctg atttgactgc gcatcttacc cctcccccat gcatgtggag tcataggagt    180 aatttttaaag gtagaatttc atattaaata tcgctgcttg attattttgt agcaaatcaa    240
aagagtgttt caagtaagta aaaacatttg agcctcccca tttgttgaaa ggagagaaat    300
taaacttggt tggggttaat tatttgatgg gtatattaat ttgcaaccgc aaggtatcga    360
taataaatat tctacaaaac ctttatcaat agtggtgaag tctttagtgc gatctacctg    420
gggttaatga acgagaagtt cttgagatat cttttcctgtt tacctccgtg catcctgtaa    480
ggaattgggt ttatcattta tcatttattt tagtacaaac ttttttttt ggcccgggcg      540 cacttttca gcggtggga actcatcaaa atgaaaaact agatacttt agacttatta       600 aatggtttaa atatttgag atgttcgtta tcagaaac ttccttactt ctatctttta       660
ttccaataca aagaagtcac aagattactt ggtaagaaag aagcagttaa ttttttaattt  720 tgccgacaag ccaagatgca aattttcgtc aagactttaa ccggtaagac tattaccctg    780
gaagttgaat cttctgacac tattgacaat gtcaagtcca agatccaaga caaggaaggt    840
attccacctg accaacaaag attgatcttt gctggtaagc aattggaaga tggtagaact    900
ttgtccgact acaacatcca aaaggaatct actctacact tggtcttgag attgagaggt    960
ggtggtaaga agaaaagaa gaaggtctac accacccccaa agaagatcaa gcacaagcac   1020
aagaaggtca agttggctgt cttgtcctac tacaaggtcg atgctgaagg taaggttacc   1080
```

```
aaattgagaa gagaatgtag caacccaact tgtggtgctg gtgttttctt ggctaaccac    1140
aaggacagat tgtactgtgg taagtgtcat tccgtctaca aggttaacgc ttaagtaaag    1200 tattttaaa acttatatat tttaattgat cgttaaattt tgaaaaaggc ttttaatatt    1260
gtcattattt acttttctat ttacaacaaa agaacaaatg aatagataga cagtagagga    1320
atataagtag tatgcagtgc catgcgggat caaggaattt gtatctctaa ttttcgtggt    1380
tgtatgcgtc tctaaacaag tcaatatttt gctgtaagat ggttctgccg ctcctttcag    1440
ttcctttaag aagcgtacct gcagatattt taacatcctc catggtttca ttgactttac    1500
tgacaagttg attgctcaag tcatcaacat gttttccca attttcacta aatacttgca    1560
aaacagcatc gaatcccatt ttacccttt tagcgttctc gcaaaacctt tgaactgacc    1620
aatcttccat cttattacac agctttctaa tggatccata tgctgtaatt tgggcttcct    1680
gctggaaaag tgttttatta gccgagtcat cgggatgcgg gctatatgtt acagtttcgt    1740
agacttttaa tagattgcac atcgttaaat tacagcttct catggtcaag ctctttttat    1800
ttaagtctac cacagaaact tctctgacat gactcatatt ggtccctcct agcatcatca    1860
tgatccattt gggaacacct tgttttacag taatcaaccg ttcagtaact aagaccttac    1920
cttgatcctt caattctctt cttaaaacgt ccactgcgat gacatgtgta gatatttcat    1980
ttgggtattt tttccagtta gcggcggtta                                     2010

<210> SEQ ID NO 75
<211> LENGTH: 6224
<212> TYPE: DNA
<213> ORGANISM: Saccharomyces cerevisiae

<400> SEQUENCE: 75
gaattccctg atcaactttc aaggaaaaac taaaactact gtattataag aggttttttc      60
acttccagat taattttgaa atacgatatc ctcaagttta tctaccagaa tatttgacta     120
agaaatcaaa ctctgttaat aataatataa ttataaaaac ctcaactaga aactccaaaa     180
aaaaaaattt accatttttt actttctatc cttgttaacc aaatttcaaa aaatttttac     240
cttttctttt tccagaagag ggaccaatca taaagatagt aataacactt taccccaaaa     300
tataaatcag acatggtagg acaacagtat tctagtgctc cactccgtac agtaaaagag     360
gtccaattcg gtcttttctc acctgaagaa gttagagcaa tcagtgtggc caaaattagg     420
tttccagaga caatggatga aacccagacg agagcgaaaa ttggtggtct aaacgaccct     480
aggttaggct ctattgatcg taatctgaag tgtcaaactt gtcaagaggg tatgaacgaa     540
tgtcctggtc attttggtca catagattta gcaaaacctg tatttcatgt tggttttatt     600
gccaaaatta agaaagtatg tgagtgtgtc tgtatgcact gtggtaagct attactggat     660
gaacataatg aattaatgag acaagctcta gcaatcaaag acagtaaaaa aaggtttgct     720
gcaatttgga ctttatgtaa aacaaaaatg gtctgcgaaa cagatgtccc ttctgaagat     780
gaccctactc agctcgtatc aaggggaggt tgtggtaata cacagcctac aattcgtaag     840
gatgggttga aattagttgg tagttggaaa aaagatagag ccacggggga tgcggatgaa     900
ccagaactaa gagttttaag tacggaggaa atcttgaata tttttaagca tatctcagta     960
aaagacttca ctagtttggg tttcaacgaa gttttttctc gtccagaatg gatgattta    1020 acatgccttc ctgtcccacc accaccggtg cgtccatcca tttccttcaa tgaatctcaa    1080
agaggtgagg atgatttaac ctttaaactt gctgatattt taaaagctaa tattagtttg    1140
```

```
gaaacactag agcataacgg tgctccacat catgctattg aagaagcaga gagtttatta    1200
caatttcatg ttgccactta tatggataat gatattgctg gtcaaccaca agctcttcaa    1260
aagtccggcc gtcccgttaa atctattcgt gctcgtttga agggtaaaga gggtcgtatc    1320
agaggtaatt taatgggtaa gcgtgtggat ttttcggcaa gaactgttat ttctggtgat    1380
cctaatttgg aattagacca agtcggtgtt ccaaaatcta ttgccaagac tttaacatac    1440
ccagaagtgg tcacaccata aacatagat cgtctgacgc aacttgttag gaatggacca    1500
aatgaacacc ccggtgccaa atacgtcatt cgtgatagcg gagaccgtat agatttaaga    1560
tacagtaaaa gggcaggtga tattcaatta cagtatgggt ggaaagttga acgtcatatt    1620
atggacaatg atccagtttt attcaaccgt caaccttcgt tgcacaaaat gtccatgatg    1680
gcccacagag taaaagttat tccatattct acatttagat tgaatttgtc cgttacatct    1740
ccatacaatg ccgatttcga cggtgacgaa atgaatcttc acgttcctca gtctgaggaa    1800
acaagggcgg aactttctca attatgtgct gttcctctac aaattgtttc accacaatct    1860
aacaaaccttt gtatgggtat tgttcaagat actttgtgtg gtattcgtaa actgacatta    1920
agagatacat ttatagaact tgatcaagtt ttgaatatgc tttattgggt tccagattgg    1980
gatggtgtta ttccgacacc tgcaattatc aagcccaaac ctttgtggtc cggtaaacaa    2040
atcttgtctg tggctatccc aaacggtatt catttacaac gttttgatga gggcactact    2100
ctgctttctc caaaggataa tggtatgctt attattgacg gtcaaatcat ttttggtgta    2160
gtagagaaaa aaaccgttgg ttcctccaat ggtggtttaa ttcatgttgt tacaagagaa    2220
aagggacctc aagtttgtgc taagttgttt ggtaacatac agaaagttgt taacttttgg    2280
ttactacata atgggttttc aacaggtatt ggtgatacca ttgcggacgg cccaacaatg    2340
agggaaatta cagagacaat tgcagaggct aaaaagaaag ttttggatgt tacgaaagaa    2400
gcccaggcaa acttattgac tgctaaacat ggtatgactc tccgtgagtc ttttgaggat    2460
aacgttgttc ggttcctaaa tgaagcaaga gataaggcag gtcgtttagc tgaagtcaat    2520
ttgaaagatt tgaacaatgt gaaacaaatg gttatggcag gttccaaggg ttcatttatt    2580
aatatcgcgc aaatgtcagc ttgtgtagga cagcaatctg ttgaaggtaa acgtattgct    2640
tttgggttcg ttgatcgtac cttacctcat ttctctaaag atgattactc cccagagtct    2700
aaaggtttg ttgagaactc atatttgaga ggtttgaccc cacaagaatt ttttttccat    2760
gcaatgggtg gtcgtgaagg tcttatcgat accgccgtca aaacagccga aacaggttat    2820
attcaacgtc gtttagtgaa agctctagaa gatatcatgt tcattacgaa taacaccaca    2880
agaaactcat tgggtaacgt tattcagttt atttatggtg aagatggtat ggatgctgcg    2940
catattgaaa agcaatcgct agatactatt ggtggctccg atgcagcttt tgaaaagaga    3000
tacagagttg atttattgaa tacagaccat acccttgatc cctcactatt ggaatccgga    3060
tctgagatac ttggcgattt gaaacttcaa gttctcctgg atgaagaata caaacaatta    3120
gtgaaagatc gtaaattttt gagggaagtt tttgttgatg gtgaagcaaa ctggccatta    3180
ccagtcaaca taagacgtat tattcaaaat gctcaacaaa cttttccacat agatcatacg    3240
aaaccatctg atttaacaat caaagacatc gttcttggtg taaaggattt gcaagaaaac    3300
ttattagtgt tgcgtggtaa gaatgaaatt atacaaaatg cccagcgaga tgcagttaca    3360
ttgttctgct gtttattacg ttcccgtttg gccacacgta gagttctgca agagtacaga    3420
ctaacaaaaac aggcattcga ttgggtatta agtaatatcg aggcacaatt cctccgttct    3480
gttgttcacc ctggtgaaat ggttggtgtt ctagcagccc aatccattgg tgaaccagcc    3540
```

```
acacaaatga cccttaacac cttccatttt gctggtgttg cttccaaaaa agttacttct    3600
ggtgtccccc gtttaaagga aattttgaat gtggccaaaa acatgaaaac gccttccttg    3660
actgtatact tagagcctgg tcatgctgcc gatcaagaac aagcgaagtt gatcagatct    3720
gctatcgagc ataccacttt aaagagtgtc actattgctt cagaaattta ctatgatcct    3780
gatccacgtt ccacagttat tccagaagat gaagaaatta ccaacttca tttctcatta    3840 ttggatgaag aagctgaaca atcttttgac caacaatcac cttggttatt acgtctggaa    3900
ctggatcgtg cagcaatgaa tgataaagac ttaacaatgg gtcaggttgg tgaaagaatc    3960
aagcaaacat tcaaaaatga tttgtttgtt atctggtctg aagacaacga tgagaagttg    4020
atcatccgtt gtcgtgttgt tcgtccaaag tcactagatg ctgagactga agcagaagaa    4080
gatcatatgt tgaagaaaat tgagaacaca atgttagaga atattacatt acgtggtgta    4140
gagaacatcg agcgtgttgt catgatgaaa tatgaccgta aagtaccaag tccaactggt    4200
gaatacgtta aggaacctga atgggtgttg gaaacagatg gtgttaactt atctgaagtt    4260
atgactgttc ctggtatcga cccaaccaga atctatacca actccttcat tgatataatg    4320
gaagttctag gtattgaagc tggtcgtgca gccttgtata aagaagttta caatgttatt    4380
gcttctgatg gttcgtatgt taactaccgt catatggctt tgttagtcga tgttatgaca    4440
acccaaggtg gcttaacttc tgttactcgt catggtttca acagatcaaa tacaggtgcc    4500
ttaatgagat gttcatttga agaaactgtc gaaattttgt ttgaagctgg tgcttcagcc    4560
gaattagatg attgtcgtgg tgtttcggaa aatgtcattc ttggtcaaat ggctccaatt    4620
ggtaccggtg catttgatgt gatgatcgat gaggagtcac tggtaaaata catgccagaa    4680
caaaaaataa ctgagattga agacggacaa gatggtggcg tcacaccata cagtaacgaa    4740
agtggtttgg tcaatgcaga tcttgacgtt aaagatgagc taatgttttc acctctggtt    4800
gattcgggtt caaatgacgc tatggctgga ggatttacag cgtacggtgg tgttgattat    4860
ggtgaagcca cgtctccatt tgctgcttat ggtgaagcac ctacatctcc cggatttgga    4920
gtctcctcac caggcttttc tccaacttcc ccaacatact ctcctacctc tccagcgtac    4980
tcaccaacat caccatcgta ctcgccaaca tcaccatcgt attcaccaac gtcaccatca    5040
tattcgccaa cgtcaccatc atattcgcca acgtcgccat cgtattctcc aacgtcacca    5100
tcgtattcgc caatgtcgcc ttcctactct cccacgtcgc caagctacag ccctacgtcg    5160
ccaagctaca gccctacgtc tccttcttat tctcctacat ctccatcata ctctcctacg    5220
tcaccaagtt acagcccaac gtcaccaagt tacagcccaa cgtctccagc ctattcccca    5280
acatcaccaa gttatagtcc tacatcgcct tcatactctc caacgtcacc atcctattcc    5340
ccaacatcac cttcttactc tcccacctct ccaaactata gccctacttc accttcttac    5400
tccccaacat ctccaggcta cagcccagga tctcctgcat attctccaaa gcaagacgaa    5460
caaaagcata atgaaaatga aaattccaga tgatatagta tatcatcctt acgtatttga    5520
cgttattaca ttatatatag tttctcaaat aatatttcta gtttattttt gtatcataat    5580
aaaaacgtat accaaatata ccattatttt tcataacatt atggtaggga tagggaatca    5640
agtaactaat ttatatccgc agagcattgg gaaaaccaac ggcgctagta aatgcattta    5700
aattacgtcc gtccaacttc taagcttcaa tggtagactc ttaactctga ccttttttagc    5760 aattaagctc ttgaagatat caaaagtgtt accgtccggc tgtaaattat aaacgttttcc    5820 tgtaaattga gtggaatacc gcttaccatt cttttgcaat cagtaaaccg tagtcttccg    5880
```

-continued

```
tgataccagt aatcatggct tgcgtatttc cgtgatctgg taatgttact atttggttac    5940
tatgtaacac aactcataat aacttggcaa tatttccgca gctccgtagt taataaactg    6000
ttttaatatg acctcaaggt tattcatata gagtgcctgc agttttctg cctttattgc     6060 tggcaataaa tcaaggtgta attgttggcg ttcttcattc aggatatcaa tccaagtttg    6120
taatgaagtt gtaggaccat cactagtcaa atttatacca cagccaagta gcaaacaata    6180
tttattgttt atgaagtggg tattaactaa taaaccagag atct                     6224
```

<210> SEQ ID NO 76
<211> LENGTH: 3969
<212> TYPE: DNA
<213> ORGANISM: Saccharomyces cerevisiae

<400> SEQUENCE: 76

```
caacttacaa tcattgttcg ccccttccat acttactgcc actcgcaaaa gggcccaacc      60
agggcaatta cgtatcaaaa aatcatgaca ggctgggtaa taaatattcg tgaagaaaga    120
agaaattaaa aaaagaaacg aagaagcaaa aaaagaaaa gactccgttt aatcactttc     180
aaccgcggtt tatccggccc cacccatgca taacccctaaa ttattagatc acttagcacg   240
tgaaaaagaa acgttttttaa tgttttttttt ttttttcttt ttctttttttt gcgttggtga  300 aaattttttc gcttcctcga gtataattat ctcatctcat ctttcatata agataagaag    360
ttttataaaa accttttgca tcaaaatttt gttgaataac tcttttttctt acgctctctt    420 tctttcctta attgttttct aaagaaccgt gtattttttct agttcgaatc catcgataac    480
attaaaagat gtctgattcc cagcaatcca ttaaggttct agaagaacta ttccagaagt    540
tatctgttgc cactgctgac aacagacacg aaatcgcttc tgaagtcgct tctttcttga    600
atggtaacat cattgaacat gatgttccag aacacttctt cggtgaattg gccaagggta    660
tcaaggacaa gaagaccgct gctaacgcca tgcaagctgt tgctcacatt gctaaccaat    720
ctaacttgtc tccatctgtt gaaccataca tcgtccaatt ggttccagct atctgtacca    780
acgcaggtaa caaggacaaa gaaattcaat ctgttgcttc cgaaactttg atttccatcg    840
ttaacgctgt taacccagtt gccatcaaag ctttgttgcc acatttgact aacgctattg    900
tagaaactaa caaatggcaa gaaaagattg ctattttggc agctttctct gctatggtcg    960
atgctgctaa ggatcaagtt gccctaagaa tgccagaatt gattccagtc ttgtctgaaa   1020
ccatgtggga caccaagaag gaagtcaagg ctgctgctac tgccgccatg accaaggcta   1080
ccgaaactgt tgacaacaag gatattgaac gtttcattcc aagtttgatt caatgtattg   1140
ctgacccaac tgaagttcca gaaaccgttc atttgctagg tgctactact ttcgttgctg   1200
aagttactcc agctactttg tccatcatgg tcccattgtt gtccagaggt ttgaacgaaa   1260
gagaaaccgg tatcaagcgt aagtctgctg ttattattga caacatgtgt aagttggtcg   1320
aagacccaca agttattgct cctttcttgg gtaaattgtt gccaggtttg aagagtaact   1380
ttgctaccat tgctgaccca gaagccagag aagttacttt gagagctttg aagactttga   1440
gaagagttgg taacgttggt gaagacgatg ctattccaga actttctcac gctggtgacg   1500
tttctactac tttgcaagtc gttaacgaat gttgaagga cgaaaccgtt gctccaagat   1560
ttaagattgt cgtcgagtac attgccgcca tggtgctga tttgatcgat gaagaatca   1620 ttgaccaaca agcttggttc acccacatca ccccatacat gactatcttc ttgcacgaaa   1680
agaaggccaa ggcatcttg gacgaattca gaaagagagc tgtcgacaac attccagttg   1740
gtccaaactt cgacgacgaa gaagacgaag gtgaagactt atgtaactgt gaattttctt   1800
```

```
tggcttatgg tgctaaaatc ttgttgaaca agacccaatt aagattgaag agagccagaa    1860
gatatggtat ctgtggtcca aacggttgtg gtaagtccac tttaatgaga gctattgcca    1920
acggtcaagt tgatggtttc ccaacccaag aagaatgtag aaccgtctac gtcgaacacg    1980
acattgatgg tactcactct gacacttccg tcttggattt cgttttcgaa tctggtgttg    2040
gtactaaaga agctatcaag gacaaattga ttgaattcgg tttcaccgat gaaatgattg    2100
ctatgccaat ctctgcttta tctggtggtt ggaagatgaa gttggctcta gctagagctg    2160
tgttgagaaa tgctgatatc ttgttgttag atgaaccaac taaccatttg gataccgtca    2220
acgttgcttg gttagttaac tacttgaaca cctgtggtat cacttctatc actatttctc    2280
acgactccgt tttcttagat aacgtctgtg aatatattat taactacgaa ggtttgaagt    2340
tgagaaagta caagggtaac tttaccgaat tcgttaagaa gtgtccagct gctaaggctt    2400
acgaagaatt atccaacact gatttggaat tcaagttccc agaaccaggt tacttggaag    2460
gtgttaagac taagcaaaag gctattgtca aggttaccaa catggaattc caatatccag    2520
gtacctctaa gccacaaatc actgacatta acttccaatg ttctttgtct tccagaattg    2580
ctgtcattgg tccaaatggt gctggtaagt ctactttgat taacgtcttg actggtgaac    2640
tattaccaac ctctggtgaa gtctacaccc acgaaaattg tcgtatcgct tacattaagc    2700
aacacgcttt tgctcatatc gaatctcatt tggacaagac tccatctgaa tatatccaat    2760
ggagattcca aaccggtgaa gatagagaaa ccatggacag agctaacaga caaatcaacg    2820
aaaacgatgc tgaagctatg aacaagatct tcaagattga aggtacccct agaagaattg    2880
ccggtatcca ctccagaaga aagttcaaga acacttacga aatgaatgt tctttcttat    2940 tgggtgaaaa cattggtatg aaatctgaaa gatgggttcc aatgatgtcc gtcgacaacg    3000
cttggattcc aagaggtgaa ttggttgaat ctcactctaa gatggttgct gaagttgata    3060
tgaaggaagc tttggcttct ggtcaattcc gtccattaac cagaaaagaa attgaagaac    3120
attgttccat gttgggtttg gacccagaaa ttgtttctca ctccagaatt agaggtttgt    3180
ctggtggtca aaaggttaag ttggtcttag ctgccggtac atggcaaaga cctcacttga    3240
ttgtcttaga tgaacctacc aactatctgg acagagattc ttgggtgct ttgtctaagg    3300 ctttgaagga atttgaaggt ggtgttatta tcattactca ctctgctgaa ttcacaaaga    3360
acttgactga agaagtctgg gccgtcaagg acggtagaat gactccatct ggtcacaact    3420 gggtagtgg tcaaggtgct ggtccaagaa tcgaaagaa ggaagacgaa gaagataaat    3480
tcgatgctat gggtaacaag attgccggtg gtaagaagaa gaagaagttg tcttctgcgg    3540
aattgagaaa gaagaagaag gaagaatga agaagaagaa ggaattgggt gatgcttacg    3600
tttcttctga cgaagaattc taatcttttt gatcactgct ttcacagttt tctttaagat    3660
ttttattgat caataattta tgtatatttt aatttctatg ttttgtaat attgtttatt    3720 ttggtaaaat atagacgcaa cttccttatt ataagaaag gcattattta aagaaaaag    3780 cgttccatta gtcagacatc ttttttttt tcatacattc ttaagcctca ggcaaattga    3840
gcattgcctc atacccttt cggtaagagg gtaacgaaaa tatttttg gaagaataaa    3900 aataggtgac ggatcataga ctaggaagct ttaaaacatg attgagcgta atattatatt    3960
ccttctaga                                                             3969

<210> SEQ ID NO 77
<211> LENGTH: 3593
<212> TYPE: DNA
```

<213> ORGANISM: Artificial Sequence
<220> FEATURE:
<223> OTHER INFORMATION: Expression vector pPICZalpha

<400> SEQUENCE: 77

| | | | | | |
|---|---|---|---|---|---|
| agatctaaca | tccaaagacg | aaaggttgaa | tgaaaccttt | tgccatccg | acatccacag | 60 |
| gtccattctc | acacataagt | gccaaacgca | acaggagggg | atacactagc | agcagaccgt | 120 |
| tgcaaacgca | ggacctccac | tcctcttctc | ctcaacaccc | acttttgcca | tcgaaaaacc | 180 |
| agcccagtta | ttgggcttga | ttggagctcg | ctcattccaa | ttccttctat | taggctacta | 240 |
| acaccatgac | tttattagcc | tgtctatcct | ggcccccctg | gcgaggttca | tgtttgttta | 300 |
| tttccgaatg | caacaagctc | cgcattacac | ccgaacatca | ctccagatga | gggctttctg | 360 |
| agtgtggggt | caaatagttt | catgttcccc | aaatggccca | aaactgacag | tttaaacgct | 420 |
| gtcttggaac | ctaatatgac | aaaagcgtga | tctcatccaa | gatgaactaa | gtttggttcg | 480 |
| ttgaaatgct | aacggccagt | tggtcaaaaa | gaaacttcca | aaagtcggca | taccgtttgt | 540 |
| cttgtttggt | attgattgac | gaatgctcaa | aaataatctc | attaatgctt | agcgcagtct | 600 |
| ctctatcgct | tctgaacccc | ggtgcacctg | tgccgaaacg | caaatgggga | acacccgct | 660 |
| ttttggatga | ttatgcattg | tctccacatt | gtatgcttcc | aagattctgg | tgggaatact | 720 |
| gctgatagcc | taacgttcat | gatcaaaatt | taactgttct | aaccctact | tgacagcaat | 780 |
| atataaacag | aaggaagctg | ccctgtctta | acctttttt | tttatcatca | ttattagctt | 840 |
| actttcataa | ttgcgactgg | ttccaattga | caagcttttg | attttaacga | cttttaacga | 900 |
| caacttgaga | agatcaaaaa | acaactaatt | attcgaaacg | atgagatttc | cttcaatttt | 960 |
| tactgctgtt | ttattcgcag | catcctccgc | attagctgct | ccagtcaaca | ctacaacaga | 1020 |
| agatgaaacg | gcacaaattc | cggctgaagc | tgtcatcggt | tactcagatt | tagaagggga | 1080 |
| tttcgatgtt | gctgttttgc | cattttccaa | cagcacaaat | aacgggttat | tgtttataaa | 1140 |
| tactactatt | gccagcattg | ctgctaaaga | agaagggta | tctctcgaga | aaagagaggc | 1200 |
| tgaagctgaa | ttcacgtggc | ccagccggcc | gtctcggatc | ggtacctcga | gccgcggcgg | 1260 |
| ccgccagctt | tctagaacaa | aaactcatct | cagaagagga | tctgaatagc | gccgtcgacc | 1320 |
| atcatcatca | tcatcattga | gtttgtagcc | ttagacatga | ctgttcctca | gttcaagttg | 1380 |
| ggcacttacg | agaagaccgg | tcttgctaga | ttctaatcaa | gaggatgtca | gaatgccatt | 1440 |
| tgcctgagag | atgcaggctt | cattttgat | actttttat | ttgtaaccta | tatagtatag | 1500 |
| gattttttt | gtcattttgt | ttcttctcgt | acgagcttgc | tcctgatcag | cctatctcgc | 1560 |
| agctgatgaa | tatcttgtgg | taggggtttg | ggaaaatcat | tcgagtttga | tgttttctt | 1620 |
| ggtatttccc | actcctcttc | agagtacaga | agattaagtg | agaccttcgt | ttgtgcggat | 1680 |
| cccccacaca | ccatagcttc | aaaatgtttc | tactcctttt | ttactcttcc | agattttctc | 1740 |
| ggactccgcg | catcgccgta | ccacttcaaa | acacccaagc | acagcatact | aaattttccc | 1800 |
| tctttcttcc | tctagggtgt | cgttaattac | ccgtactaaa | ggtttggaaa | agaaaaaaga | 1860 |
| gaccgcctcg | tttctttttc | ttcgtcgaaa | aaggcaataa | aaattttat | cacgtttctt | 1920 |
| tttcttgaaa | ttttttttt | tagttttttt | ctctttcagt | gacctccatt | gatatttaag | 1980 |
| ttaataaacg | gtcttcaatt | tctcaagttt | cagtttcatt | tttcttgttc | tattacaact | 2040 |
| ttttttactt | cttgttcatt | agaaagaaag | catagcaatc | taatctaagg | ggcggtgttg | 2100 |
| acaattaatc | atcggcatag | tatatcggca | tagtataata | cgacaaggtg | aggaactaaa | 2160 |
| ccatggccaa | gttgaccagt | gccgttccgg | tgctcaccgc | gcgcgacgtc | gccggagcgg | 2220 |

-continued

```
tcgagttctg gaccgaccgg ctcgggttct cccgggactt cgtggaggac gacttcgccg   2280
gtgtggtccg ggacgacgtg accctgttca tcagcgcggt ccaggaccag gtggtgccgg   2340
acaacaccct ggcctgggtg tgggtgcgcg gcctggacga gctgtacgcc gagtggtcgg   2400
aggtcgtgtc cacgaacttc cgggacgcct ccgggccggc catgaccgag atcggcgagc   2460
agccgtgggg gcgggagttc gccctgcgcg accggccgg caactgcgtg cacttcgtgg   2520
ccgaggagca ggactgacac gtccgacggc ggcccacggg tcccaggcct cggagatccg   2580 tcccccttt cctttgtcga tatcatgtaa ttagttatgt cacgcttaca ttcacgccct   2640
ccccccacat ccgctctaac cgaaaaggaa ggagttagac aacctgaagt ctaggtccct   2700 atttatttt ttatagttat gttagtatta agaacgttat ttatatttca aattttctt   2760 ttttttctgt acagacgcgt gtacgcatgt aacattatac tgaaaacctt gcttgagaag   2820
gttttgggac gctcgaaggc tttaatttgc aagctggaga ccaacatgtg agcaaaaggc   2880
cagcaaaagg ccaggaaccg taaaaaggcc gcgttgctgg cgttttccca taggctccgc   2940
ccccctgacg agcatcacaa aaatcgacgc tcaagtcaga ggtggcgaaa cccgacagga   3000
ctataaagat accaggcgtt tccccctgga agctccctcg tgcgctctcc tgttccgacc   3060
ctgccgctta ccggatacct gtccgccttt ctcccttcgg gaagcgtggc gctttctcaa   3120
tgctcacgct gtaggtatct cagttcggtg taggtcgttc gctccaagct gggctgtgtg   3180
cacgaacccc ccgttcagcc cgaccgctgc gccttatccg gtaactatcg tcttgagtcc   3240
aacccggtaa gacacgactt atcgccactg gcagcagcca ctggtaacag gattagcaga   3300
gcgaggtatg taggcggtgc tacagagttc ttgaagtggt ggcctaacta cggctacact   3360
agaaggacag tatttggtat ctgcgctctg ctgaagccag ttaccttcgg aaaaagagtt   3420
ggtagctctt gatccggcaa acaaaccacc gctggtagcg tggtttttt tgtttgcaag   3480 cagcagatta cgcgcagaaa aaaaggatct caagaagatc ctttgatctt ttctacgggg   3540
tctgacgctc agtggaacga aaactcacgt taagggattt tggtcatgag atc          3593
```

<210> SEQ ID NO 78
<211> LENGTH: 3731
<212> TYPE: DNA
<213> ORGANISM: Aspergillus nidulans

<400> SEQUENCE: 78

```
tctagatgtt gttgcaatgc tagggaaaag tcaccggtcg ctggtatgat aagaagcgcg     60
agagcggtcc aatcagcatt atattgctag ggagcgcgca ggagtgaggc ttgcatttgc    120
agagagcgaa agcgatagtc ggccatggtc ctctgcttcg aagatcgatt taaaatcaac    180
gatatggaca tccaggtttc tttgtatctg ccagtagat gaatcgcgtt caagctttca    240
aggaacgtca aaagaaccca cccagctgca actggaagga tggatggtgt ttgcaagcat    300
ggataaagaa gtcacgggtt ctgtcagagc gcgtcgagtc gcgactgaat gcagttgttg    360
gccactcacg ctgaagtcga ggcccacacg gtttgctgct gctctttcct attggacaaa    420
tttgccacca cagcgcccat aaattttccc tagagttacg ctagcggctt gccgtccatg    480
ggtctgagac ttgggcttag cccgcctttc cgcctcccca aaacatataa agcccgtcac    540 ctcccccgacc ctgcgtttta gaaatttatg tcggtcggct cttggcgctt gtcctcattc    600
cgctcccctc ccctcacccg actctctctc cacacacaaa gtccttgagg tctgcagatt    660
ctcgctcttg cgtagtctgc taaattcagg tgccaaaaaa ataagttgct gagacaaaag    720
```

```
ttgcagcctc aggcacgcat cagcatctta tcttcgccgt tcacttcaaa cacaaatcac    780
accaagatag aagagcttac ccgaggatac tggaagcaag aagaatctga gcttgtcatc    840
cgaagtgttt cctctactta tccactccct ttattacaca tcgctgctcg cttgcaattc    900
attatcgcga caaaactgtc atttcaatta atagaaaaca cttcattgtg atctttcttc    960
tgcccatcct cacaaccctt cacatatctc ccctctattg ggcattgcgt ttctcgtcaa   1020
ttgccctgcg cctgttttgc tactgcgaaa cggctcatcc ttgaaggcag tctactaggg   1080
gatacattca gttgtccatc tccacgaggt tgttgttca tcccgccctg tcgcccaatc    1140
gcatatgcct cccccataat ttcccatctt tccatatttg cgggaactaa ctcgctgcag   1200
tctgccagtt ttcactcaac tggtcacaca cttgagcaaa gtttgacaga cctgacaatg   1260
gactcgctca ctactcatcc tgccactgcc aacaggctc gtgccttcac ttctccctcg    1320
tcgctgtctt tccctggcgg cactgccttc cctggtggtg ctgacctgac accgccttcc   1380
gataaggatg cgaatatggc cactaatggt cagagcgcga atgaaatgt gaatggccag    1440 cagcagggag caaatgccgc taacggcaat ggggtgatgc ccgctactcc agctgcgacc   1500
cctggtgcca gcgctccagg gagtggtatc gtgcctacct tgcagtgagt atactctgtt   1560
gtcatctttc tggtccacca gaatactgaa caaagactac tcttgaagaa acattgtcgc   1620
tacagtcaac cttgattgtc gtcttgatct caagactatt gcgctgcacg ccagaaatgc   1680
ggaatacaac cctaaggtat tattttccac acctccctga gtggattaaa tcagggtaca   1740
gtgtggctga actggttttc ctctagcgtt tcgcggccgt tatcatgcgt attcgggaac   1800
ccaagacgac tgcgttgatc ttcgcctctg gcaagatggt ggttactggt gccaagtcgg   1860
aagacgattc caagttggct tcgaggaagt acgctcgtat catccagaag ttgggcttca   1920
atgccaagtt cacagatttc aaaatccaga acattgtggg gtcctgcgat atcaaatttc   1980
caattcgttt ggaaggtctg gcgagtcgtc accacaactt cagttcctac gaaccggagc   2040
tgttcccagg tcttatttac cgtatgatga agccaaagat cgtcctcttg atcttcgtca   2100
gcggaaaaat tgtcctgacc ggagccaaag tccgtgaaga gatctatcag gctttcgaac   2160
tcatctaccc tgtgctctct ggtaagcttc ccacgttcga tatccgaaca cccgctaatt   2220
ttggtacaga tttccgcaag gtctaaagag tagcaattct gatgaggggc tgagatatct   2280
cagcactttg tcatactcac ttcaaacccc tgtattatca aaaagtttct cgatgccggg   2340
gcggctaagg ctcaagtcta gtcagccgtg gtatcttctg aactgcatca cgagttttat   2400
gcgagcatta gtacggcgtt ctagcgattc gggtttgttt ggtttttttt tctaaggcaa   2460
ttttcaacac gattcacaaa ttagacagtc gcacaccgca ggttgaaaag ggggcggtac   2520
tgcgcgctgg tcggcttgtt gcctccttct aattccccgt tgtcttcca gtctattgac    2580 accgagggct tctcgaactg ctctatgcag tctcttgggt tactcgtctt ttttttcccg   2640
tgggcactgg gctccctgtt ttagatcgtc ctacttaatt gatgcctgat gacgggtttg   2700
taagcctgat ccagtagcat tacttaacat ataaataaa agtggatga gatctttctt    2760 tcgccgttta ggtcttaaaa gccagtttgc gtcttaaagc cagtttgcga atataaatgt   2820
tcgtataagg atgaatcgta ttcaaagaat taaattgtca gaaaaactac tgatgctcgc   2880
ataagacatg tgatgcagtc gaagatacgc atgcatatac atatatacac tagctaacat   2940
ccacccaata tatatatccc tctccgtttta tctatttcac acacatacca aaagctggtt  3000
ttatccgtca gacctacaac gcactctccc gcttcgcttt ctgccccttc gccaactcat   3060
ccaaaagcag cagccgctta tcccctgaac gacttccatc ctctgttccg tcaaagtggg   3120
```

```
cctcgtccac agcctccggc cagtcccaga gcgcgcgcag ttcgggtgcg agcttaccct      3180
ccagcgcatc gaccacctt tcgccgataa gtgggaagaa tttgtatgcg tggccgctgc      3240
caccagttgc aaggacgagg tgtgggtgcg atggatggtg ggtgattatg aagtcgcctc      3300
tgggactgtt tgggcatagt tagtatcgaa tggtcatgag caataaaggg tttacgacga      3360
catacgtatc tgtgtaccag cagatccggg tattgaggaa aggacggtcc gcgaaggagg      3420
ggaggagctg cttcagggct gtgcggaagg ccgtatcccc ctccagcggg atgggacgc       3480 ccttctccgg caagctgacg tgcattgttt ctcctgttgg tgtcgcgccg ggcacgggaa      3540
ctgccttggg gttgtggtag ccgtacggtg tcgggcgatc ttgaggatgt tgttgcgcgg      3600
cggaatgatg aagatacccg ttgcgaaatt gaggatcgtg ggcatgtgtt cgaggcggcg      3660
ttgctcctcg tctgagatgc gcatgtaggc gattgcttgg ccggttgaga cagcgcgacc      3720
ccgaagtcga c                                                          3731

<210> SEQ ID NO 79
<211> LENGTH: 2367
<212> TYPE: DNA
<213> ORGANISM: Aspergillus nidulans

<400> SEQUENCE: 79
ctcgaggttt tgatgtaaaa cgagcagcag atttgttggc cttcagcagg ggaagaaatt        60
tgccagaaaa atgatggttg ccccgcctcc ggctgggcgg gttgagtttt gtttgatttg       120
tttacaccac tacggtccgg ttactgataa ggaacccgga gatcgggccc agcggcttcc       180
ccgccaacaa gcgccggctt ccaagcaaca aagcatcaag ccattcgaga tacatctcac       240
ctccaatata cctacctccc tgaagacctt atggctccgc gttatatccc ttagatgtcc       300
tgattcttga ttattgcctt tcacacccttt cacgccaatt tctttccctt tctttcagct      360
gtgctattga taagataaac aagaatggcc ttcttcttca atcggggtcg atcccgccaa       420
ccatccgacg ttgtgagatc aatcaaggac ctgctgctga gactccgtga gccttcgacc       480
gcttctaagg tctgtccagt ctcttaagac tttctccacc gaccgatcgc ttgctaagcc       540
tctatcaggt tgaggatgaa ttagccaagc agctatcaca gatgaagttg atggtgcagg       600
ggactcaagg ttcgtacagc tcaaaggaaa ctaaatatgg cgtggtctaa cttactgatc       660
tgtgttttgg cagaacttga agcttctact gatcaggttc atgccctggt ccaagctatg       720
ctccacgagg atctgcttta cgaactcgcg gtggctcttc acaaccttcc cttcgaagca       780
agaaaagata cgcaaaccat attctctcac atactccgct ttaagcctcc tcacggaaac       840
tcgccagacc ctcccgtcat ctcttacatc gttcacaatc gtcctgaaat tatcattgag       900
ctatgtaggg gctacgagca cagccaaagt gccatgccat gcggcactat cttgagggag       960
gcattgaagt tcgacgtaat cgccgctatc attctttatg atcagtcaaa agagggggag      1020
ccagctatca gactgaccga ggtccagccc aacgttcctc agcgcggaac aggtgttttc      1080
tggaggttct tccattggat tgaccgaggt accttttgagc tcagcgcaga tgcattcaca      1140
acttttaggg caagtgcaca agaaaatcat ttctaagaaa ctatcctaac acgaaactgt      1200
ttcctcagga aatcttgacg cgccacaaat cccttgttac aggatatcta gcgacaaact      1260
tcgattactt tttcgcgcag tttaacactt tcctcgttca gtctgagtca tatgtcacta      1320
agcgacagag catcaaactc ttaggcgaga tttactcga tcgcgcaaac tacagtgtga       1380
tgatgcgata cgtcgagagc ggagaaaacc tcaagctttg catgaagctc ctgcgtgatg      1440
```

```
atcgcaagat ggttcaatat gagggatttc atgttttcaa ggtatgtgaa ggacgcaacc    1500
tctatgaccg cgtaggatgc gtcgtgctga caaagaatgt ggttaggtat ttgtcgccaa    1560
tccggacaag tcagtggcag tccagcgaat tctgatcaac aaccgggatc gcttgctaag    1620
attcctaccg aaattcctgg aggaccgcac agacgacgac cagttcacgg acgagaagag    1680
tttcctagtc cgacagattg aacttttacc caaggaaccc attgaaccat cacgttctgc    1740
gcgtgaaccg tctcgttcga ctgccaacac cacgactgtt gcgtagacat gagcggggct    1800
acttacagct ggccgcagta tctacatgac acatcatcgg tgttgttgtt gttgttgttg    1860
ttgttgcatg gtcatctggg atcgcccttt cgtcgcctgt gtctcgtgtc cagaccccgc    1920
gcgtccttgg ctgtagtctc tgtacgtatg gttttgcatt tacggccagc tggtatctgg    1980 cttttttggag ttacttttttg ggatttggaa agaactacac agcttgttgc ctggagcgat    2040
gccttggaca caaacagga aatcgacgg aaggatgca ataatggacg ggaagtttag    2100
agtccttgca ttggaggcgg gcataggcag ccctggaata cagaaccctg tagagttaag    2160
gagtgtaaac acccgacaca gtatatacca ggccccttg tctcagggca cgagccaggg    2220
gcctatagag cgataaaacc atgcgactat tgataataat gataaccagc agcgcatagc    2280
ccagtacgag gccttgacgt caaggtcagt ttctgcagaa caatcgcatt atcgaatcca    2340
tggaatgcac tgggcctggt gggatcc                                        2367
```

<210> SEQ ID NO 80
<211> LENGTH: 2686
<212> TYPE: DNA
<213> ORGANISM: Aspergillus nidulans

<400> SEQUENCE: 80

```
aacctccagc ccctttccag tccttctgtt cagttcgagc ggctgtcgag ctgctgctga      60
ctactccgcc taccgctaca acctccaacc aaccaccgac caccaacaaa ccctcgactc     120 tctcccttc tctcctccac ttctcaacat ccaactcccc attctcgctc tgttcatcat     180
ctctcctcct cccttcctta cctgtcaacc tctcatttct tttctctctt gttcttcgta     240
gttcgattct aatccacccc taaacaccat ggaaggtaag gttctgcca cgcaacgcct     300 tgcttccctc gcttgcttcc ttcccctccc tccacatcct tcagctgtca actttgcgct     360
aatttgttct tctttggctg cctacagagg aagttgctgc tctcgttatc gacaatgggt     420
atgtcttgac tgtgtttgat ggcactgcga tgccagttca cttccgtgct tgtccctgaa     480
cactcgcctg gtctcgccgc tgtcgcaacg acctacccgt ccttggtatc ttggttgggc     540
attggcgttc gcctatggca agcagctatt cagaacgatt agcacggctg ttctgcgtcg     600
agaatacatg aatacatgga ttagttgata tgctgactcg gggttcccta gttcgggtat     660
gtgcaaggcc ggtttcgccg gtgacgatgc ccccgtgcc gtcttccgta agtcaccctt     720 tcctcccta tatacaaccc cttccttccc ccgtgaacct gtcaccccctg tcatcgaacc     780 tactcgataa aatgtgttca ccgcgctctt ggcacgacga tggtctcaag ggcggtgaac     840
atatcactct atcatgcgat tacatgtcaa gtgtgagacc ggctgctaac tatgctgcac     900
agcctccatt gtcggtcgtc cccgtcacca tgggtaaata tcccttaact gtatctccat     960
caacagagat gtggccgctg acgtccgaat tagtatcatg atcggtatgg gtcagaagga    1020
ctcctacgtc ggtgatgagg cacagtccaa gcgtggtatc ctcacactca gatacccat    1080 tgagcacggt gttgtcacga actgggatga catggagaag atttggcacc acacattcta    1140
caacgagctt cgtgtcgctc ctgaggagca ccccgtcctc ttgaccgaag ccccatcaa    1200
```

```
tcccaagtcc aaccgtgaga agatgactca gatcgtcttc gagactttca acgtccccgc    1260
cttctacgtc tctattcagg ccgttctctc cctgtatgct tccggtcgta ccaccggtat    1320
cgtccttgac tctggtgatg gtgttaccca cgtcgtcccc atctacgagg gtttcgctct    1380
tccccacgcc atctcccgtg tcgacatggc tggtcgtgac ctgacggact acctgatgaa    1440
gatcttggcc gagcgcggat acaccttctc cactaccgct gagcgtgaaa ttgtccgtga    1500
catcaaggag aagctctgct acgtcgccct tgacttcgag caggagatcc agaccgcttc    1560
tcagagctcc agcctcgaga agtcctacga actgcctgat ggtcaggtta tcaccatcgg    1620
caacgagcgc ttccgtgctc ctaaggctct cttccagccc agcgttcttg gtctggaaag    1680
cggtggtatc cacgtcacca ctttcaactc tatcataaag tgtgatgtcg acgtccgtaa    1740
ggatctgtac ggcaacatcg ttatggtatg tatcactctt agcctcgctc tactgcactg    1800
ggcggcacta acgaatcgat agtctggtgg taccaccatg taccctggta tctccgaccg    1860
tatgcagaag gaaatcaccg cccttgcgcc ctcatccatg aaggtcaaga tcattgctcc    1920
tcctgagcgc aaatactccg tctggatcgg tggttccatc ttggcttctc tgtccacctt    1980
ccaacagatg tggatctcca gcaggagta cgatgagagc ggtccttcga tcgtccaccg    2040
caagtgcttc taaggtatga gtcgcaaaat tgttttttat ttttggtctt gagtctaata    2100
tgctcgcagc tcttgagttg tatatggtcg ttggtcgcgt attttctgtt gtattaaaag    2160
atcaaacgag atcaagggat ggctcgcggg ctgtctctcg cactaggagg aagaatgcct    2220 gaaaaggaa ctttgatttt agctgtggaa tagagatggc ttgtttgagg acgcttgtcg    2280
cttggcgcag ggacttgaat ggcagcttgt ggaaaccgaa ggcgagaaaa gtcgacggat    2340
actgtacgtg gttctattgc cagtgcggtg gaagcttggt tgtgatatag ttcaatcctt    2400
ctttgaatct gtttgtttca tatttggatt ctctgcttgc gcattctcat cttcgagaag    2460
cgactgcagg gattgttggt tctgtggagc tgatgagcgc gccttgacca cccttgttct    2520
tgttttgctc ttttgttctc atttaacccg tttctccctt ccaacccttt gaccttgcaa    2580
cattgtctcc cagcgcgttg ccaaagcgaa cttgatatca gtatagtatg accaagtagt    2640
ctaccaaaat aaattttagt acagtattgc tagtatacag ataatt                   2686
```

<210> SEQ ID NO 81
<211> LENGTH: 4046
<212> TYPE: DNA
<213> ORGANISM: Saccharomyces cerevisiae

<400> SEQUENCE: 81

```
cctctagagt cgagtatttt tggtgtaggt cccatttttct tcaaaggtcc tgtttagact    60
atccgcagga aagaaattag aatgaccggc ttgaatggag atgatcctga tgactactat    120
ctgaacctta atcaagatga agagtctcta cttaggtcaa gacacagtgt cggctcagga    180
gcacctcata gacaaggctc tttagtgcgg cccgaaagaa gccgactgaa caatcctgat    240
aatccacttt ttattatgcg cagaaaacgc aggagcagat gaatcacctg gatgtttttac    300 catcaagtac cggtgtaaac ccaaatgcaa ctcgtcggag tggctccctg cgctccaaag    360
gctcagtgag aagcaaattt agtggccgcg aaacggatag ctatcttta caagatatga    420 atactactga caagaaggct tccgttaaaa taagtgatga aggtgttgcg gaagacgaat    480
ttgataaaga tggtgatgtg gacaatttcg aagaaagctc cacgcagccc ataaataagt    540
ctatcaaacc attaagaaag gaaacgaatg atacattgtc attttggcag atgtactgtt    600
```

```
atttcattac gttttgggca cctgctccaa ttcttgcttt ctgcgggatg ccaaagaagg    660
aaagacaaat ggcgtggaga gaaaaggttg ctttaatttc tgtcatcttg tacattggtg    720
cgattgtggc tttcctgact tttggtttca ctaaaaccgt tgtagtagt tcgaaactac     780
gtttgaaaaa caacgaagta tcaacagaat ttgtcgtaat aacggtaag gcttatgaat     840
tggatacttc ctcgcgttcc ggtatacaag acgttgaagt agattcagac acctttatg     900
ggccctggtc agatgctggt aaagatgctt cgttcttgtt tcaaaatgtg aatggtaact    960
gtcataacct tataactcca aagagtaatt cttccattcc ccatgacgat gataataatt   1020
tagcatggta ttttccttgt aagttaaaga atcaagatgg ctcttcgaag ccaaacttca   1080
cagttgaaaa ttacgcagga tggaactgtc atacgtctaa agaagatagg gacgcatttt   1140
acggtttaaa gtcgaaagct gatgtttact tcacttggga tggtataaag aactcttcta   1200
gaaacttgat tgtttataat ggcgacgttt ggatttaga tcttcttgat tggttggaaa    1260
aggatgacgt tgactatccc gttgtattcg atgacttgaa gacttcaaat ttacaaggtt   1320
atgatctttc gttggttttg tcaaatgggc atgaagaaa aattgcgaga tgtttgagcg    1380
aaattattaa agttggtgaa gtagactcca aaaccgtcgg ttgtattgcc tctgatgtcg   1440
ttttgtatgt ttctctggta tttattcttt cagtggtgat aattaaattc ataattgcct   1500
gctacttccg ttggactgta gctaggaaac aaggtgcata tatcgtggac aataaaacaa   1560
tggataaaca cacaaacgat atcgaggatt ggtctaataa tattcaaaca aaagctcctc   1620
taaaggaagt agatcctcat ttgaggccaa agaaatactc aaaaaagtcg ttgggacaca   1680
agcgtgcttc aacctttgac ttgctgaaaa acacagctc caaaatgttt caatttaacg    1740
aatctgtgat agatctagac acctccatga gcagttcact acaatcttct ggttcataca   1800
gaggaatgac aacaatgacc actcaaaatg cttggaaact ctcgaatgaa acaaagctg    1860
tacattcccg taatccatct actttgttgc ctacatcctc gatgtttgg aataaagcga    1920
cttcctctcc tgtaccagga tcatcgctga ttcagagtct tgattcgacg attatacatc   1980
ccgatatcgt tcaacaacca ccactggatt ttatgccata cgggttccca ttgattcata   2040
ctatctgttt tgttacttgt tattctgagg atgaagaggg tttaagaacc actttagact   2100
ctctttctac cacagattat ccaaattccc ataaactact gatggttgtt tgtgatggtt   2160
taattaaggg ctcgggcaac gataagacta ctccagagat agcgttagga atgatggacg   2220
actttgtcac cccacctgat gaagttaaac cttactccta tgtggcagtg gcatcaggct   2280
ctaaaagaca caatatggcc aagatatatg cgggtttta caaatatgac gattctacaa    2340
ttccaccaga aaatcaacaa cgtgtcccaa tcattacaat tgtgaagtgc ggtactcctg   2400
cagagcaggg ggccgccaaa cccggtaaca gaggtaagcg tgattctcaa attattctga   2460
tgtcctttt agaaaaaata acatttgatg aaagaatgac tcaattggaa tttcagcttt    2520
taaaaatat ttggcagatt acggggctaa tggcagactt ctacgaaacg gtacttatgg    2580
ttgatgctga tactaaagtc tttcccgatg ctttaactca tatggtcgct gaaatggtta   2640
aagatccttt gattatgggt ctttgtggtg agaccaagat cgctaataag gcacaatctt   2700
gggtaactgc aattcaagtg tttgagtact atatttcgca tcatcaggct aaagcttttg   2760
aatctgtctt cggttcggta acttgtttgc cgggatgttt tcaatgtat cgtataaaat    2820
ctcctaaagg ttcagatggt tattgggtac ctgtattggc aaatccagat attgttgaaa   2880
gatattcgga taatgttaca aacactttgc ataagaagaa cttattatta cttggtgaag   2940
atagatttt atcttcatta atgttaaaga ctttccctaa gagaaagcaa gtatttgttc    3000
```

```
caaaagctgc ttgtaaaact attgccoctg ataaattcaa agtcttactt tcccagcgtc    3060
gaagatggat taattctacg gtacataacc tttttgaatt agttctaatc agagacttat    3120
gtggcacttt ctgtttttcc atgcaatttg tgattggtat tgaattgatt ggtactatgg    3180
tactgccgtt agccatttgc tttactattt atgtcattat ttttgccatt gtatcaaaac    3240
ctacacccgt aatcacttta gttttactgg caattattct tggtctgccc ggcttaattg    3300
ttgttataac tgctacgaga tggtcgtacc tatggtggat gtgcgtatat atttgtgctt    3360
tgcctatttg gaatttcgta ctaccttcat atgcgtactg gaaatttgat gacttctcat    3420
ggggtgatac gagaactatt gcgggaggta ataaaaaggc acaagacgag aatgaaggtg    3480
aatttgatca ctcaaagatt aaaatgagga catggaggga atttgaaagg gaagatattc    3540
tcaatcggaa ggaggaaagt gactccttcg ttgcatagac agtatgaaaa tatttttact    3600
gtgatactta caagttgata tatggttgtg tgtaacttat ttatttgaga ggtattttaa    3660
cacaccttag aactaaaact taataaataa atatttctct atctttaaag gcacatatta    3720
cgtggctaag gcaattacag ctgatatact gtaaaactca tgtcgccact aaattcttct    3780
aacacgcgtt ctgtctcttt ccaagggact ccgaatatgc cactatttat ctgtggcatt    3840
tccaatttat attccoctat tgggtatttg atgtggccgt ttaaatagtc accgattgaa    3900
tcttcacttg ttcgagtttt gtcttttgct tctctaaagg tcttcaattt atctaaagca    3960
agttttgtat aattcaaaat actttgcttt tctccatgac ttgaacctcc aaatgatgat    4020
gtaaacaagc aacaaatcag cagatc                                         4046
```